(12) United States Patent
Smith et al.

(10) Patent No.: US 7,429,660 B2
(45) Date of Patent: Sep. 30, 2008

(54) ATM INHIBITORS

(75) Inventors: Graeme Cameron Murray Smith, Cambridge (GB); Niall Morrison Barr Martin, Cambridge (GB); Xiao-Ling Fan Cockcroft, Horsham (GB); Ian Timothy Williams Matthews, Horsham (GB); Keith Allan Menear, Horsham (GB); Laurent Jean Martin Rigoreau, Horsham (GB); Marc Geoffrey Hummersone, Horsham (GB); Roger John Griffin, Morpeth (GB)

(73) Assignee: Kudos Pharmaceuticals Limited, Cambridge (GB)

( * ) Notice: Subject to any disclaimer, the term of this patent is extended or adjusted under 35 U.S.C. 154(b) by 450 days.

(21) Appl. No.: 10/918,180

(22) Filed: Aug. 13, 2004

(65) Prior Publication Data

US 2005/0054657 A1    Mar. 10, 2005

Related U.S. Application Data

(63) Continuation of application No. 60/494,776, filed on Aug. 13, 2003.

(51) Int. Cl.
A61K 413/00 (2006.01)

(52) U.S. Cl. .................. 544/114; 544/145; 544/147

(58) Field of Classification Search .............. 544/114, 544/145, 147; 514/231.5
See application file for complete search history.

(56) References Cited

U.S. PATENT DOCUMENTS

| 4,954,518 | A | 9/1990 | Takano et al. |
| 5,252,735 | A | 10/1993 | Morris |
| 5,284,856 | A | 2/1994 | Naik et al. |
| 5,302,613 | A | 4/1994 | Morris |
| 5,703,075 | A | 12/1997 | Gammill et al. |
| 5,733,920 | A | 3/1998 | Mansuri et al. |
| 5,922,755 | A | 7/1999 | Tanaka et al. |
| 6,348,311 | B1 | 2/2002 | Kastan et al. |
| 6,387,640 | B1 | 5/2002 | Kastan et al. |
| 7,049,313 | B2 * | 5/2006 | Smith et al. ............. 514/231.5 |
| 2004/0002492 | A1 | 1/2004 | Murray Smith et al. |
| 2004/0023968 | A1 | 2/2004 | Martin et al. |
| 2004/0192687 | A1 | 9/2004 | Martin et al. |
| 2006/0106025 | A1 | 5/2006 | Smith et al. |
| 2006/0178361 | A1 | 8/2006 | Hummersone et al. |

FOREIGN PATENT DOCUMENTS

| EP | 0610519 A1 | 8/1994 |
| EP | 0635268 A1 | 1/1995 |
| EP | 0640339 A1 | 3/1995 |
| EP | 0641566 A1 | 3/1995 |
| EP | 0648492 A2 | 4/1995 |
| EP | 0658343 A1 | 6/1995 |
| GB | 1303724 | 1/1973 |
| GB | 2302021 A | 1/1997 |
| JP | 03215-423 | 1/1990 |
| WO | WO 90/06921 | 6/1990 |
| WO | WO 91/19707 | 12/1991 |
| WO | WO 92/00290 | 1/1992 |
| WO | WO 95/29673 | 11/1995 |
| WO | WO 96/01108 | 1/1996 |
| WO | WO 97/15658 | 5/1997 |
| WO | WO 97/18323 | 5/1997 |
| WO | WO 98/55602 | 12/1998 |
| WO | WO 98/56391 | 12/1998 |
| WO | WO 99/47494 | 9/1999 |
| WO | WO 01/53266 A1 | 7/2001 |
| WO | WO 02/20500 A2 | 3/2002 |
| WO | WO 02/056912 A2 | 7/2002 |
| WO | WO 03/024949 A1 | 3/2003 |
| WO | WO 03/093261 | 4/2003 |
| WO | WO 03/034997 A2 | 5/2003 |
| WO | WO 03/035618 A2 | 5/2003 |
| WO | WO 03/070726 | 8/2003 |
| WO | 2006032869 | 3/2006 |

OTHER PUBLICATIONS

Ismail, I.H. et al., "SU11752 inhibits the DNA-dependent protein kinase and DNA double-strand break repair resulting in ionizing radiation sensitization," Oncogene (2004) 23:873-883.
Kashishian, A. et al., "DNA-dependent protein kinase inhibitors as drug candidates for the treatment of cancer," Mol. Cancer Ther. (2003) 2:1257-1264.

(Continued)

Primary Examiner—Rei-Tsang Shiao
(74) Attorney, Agent, or Firm—Michael Best & Friedrich LLP

(57) ABSTRACT

A compound of formula I:

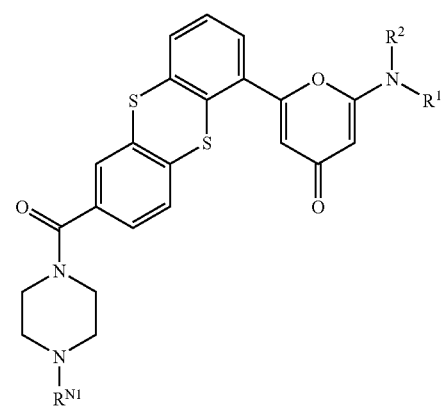

and isomers, salts, solvates, chemically protected forms, and prodrugs thereof, wherein: $R^1$ and $R^2$ together form, along with the nitrogen atom to which they are attached, an optionally substituted heterocyclic ring having from 4 to 8 ring atoms; and $R^{N1}$ is selected from hydrogen, an optionally substituted $C_{1-7}$ alkyl group, an optionally substituted $C_{3-20}$ heterocyclyl group, an optionally substituted $C_{5-20}$ aryl group, an acyl group, an ester group and an amido group, and its use as a pharmaceutical.

12 Claims, No Drawings

OTHER PUBLICATIONS

Lau et al., "Suppression of HIV-I infection by a small molecule inhibitor of the ATM kinase," Nature Cell Biology (2002) 7:493-500.

Muller, C. et al., "DNA-dependent protein kinase activity correlates with clinical and in vitro sensitivity of chronic lymphocytic leukemia lymphocytes to nitrogen mustards," Blood (1998) 92:2213-2219.

Sirzen, F. et al., "DNA-dependent protein kinase content and activity in lung carcinoma cell lines: Correlation with intrinsic radiosensitivity," Eur. J. Cancer (1999) 35:111-116.

Abraham, Robert T., "Cell cycle checkpoint signaling through the ATM and ATR kinases," Genes & Dev., 15: 2177-2196 (2001).

Archer, S. et al., "Ring-Hydroxylated Analogues of Lucanthone as Antitumor Agents," J. Med. Chem., 25, 220-227 (1982).

Banin, S., et al., "Enhanced Phosphorylation of p53 by ATM in Response to DNA Damage," Science, 281:1674-1677 (1998).

Bantick, J.R., et al., "Synthesis of 2-aminochromones," J. Heterocyclic Chem., 1981, vol. 18, pp. 679-684.

Berge, Stephen M., et al., "Review article," J. Pharm. Sci., 66:1, pp. 1-19 (1977).

Bettoni, et al., "Synthesis and absolute configuration of substituted morpholines," Tetrahedron, 1980, vol. 36, pp. 409-415.

Boyd, J., et al., "The chemistry of the 'insoluble red' woods," J. Chem. Soc., 1948, pp. 174-176.

Brown, P.O., "Integration of retroviral DNA," Curr. Top Microbiol. Immunol., 157:19-48 (1990).

Buon, C., et al., "Synthesis of 3-substituted and 2,3-disubstituted-4H-1,4- Benzoxazines," Tetrahedron, 2000, vol. 56, pp. 605-614.

Chiosis G, et al. "LY294002-geldanamycin heterodiamers as selective inhibitors of the PI3K and PI3k-related family", Bioorganic & Medicinal Chemistry Letters, vol. 11, No. 7, Apr. 9, 2001 pp. 909-913, XP004232522.

Daniel, R., et al., "A role for DNA-PK in retroviral DNA integration," Science, 1999, vol. 284, pp. 644-647.

Daniel, Rene, et al., "Wortmannin Potentiates Integrase-Mediated Killing of Lymphocytes and Reduces the Efficiency of Stable Transduction by Retroviruses," Mol. Cell Biol., 21(4): 1164-1172 (2001).

Datta, A., et al., "Reformatsky reaction on aroylketene S, N-acetals: a facile route to 4-amino-6-aryl-2H-pyran-2-ones," Synthesis, 1988, vol. 3, pp. 248-250.

Di Braccio, M., et al., "1,2-fused pyrimidines VII," Eur. J. Med., Chem., 1995, vol. 30, No. 1, pp. 27-38.

Di Braccio, M., et al., "Pyran derivatives XIX. (Dialkylamino) substituted 1-benzopyranones and naphthopyranoes with platelet antiaggregating activity," Farmaco, 1995, vol. 50, No. 10, pp. 703-711.

Durocher, Daniel, and Jackson, Stephen P., "DNA-PK, ATM and ATR as sensors of DNA damage: variations on a theme?," Curr. Opin. Cell Biol., 13:225-231 (2001).

Ermili, A., et al., "Chemical and pharamacological research on pyran derivatives," Enclosed: Chemical Abstracts, 1977, vol. 87, No. 15, p. 588 (XP-002218602). 117750g.

Gell, D., et al., "Mapping of protein-protein interactions within the DNA-dependent protein kinase complex," Nucleic Acid Res., 1999, vol. 27, No. 17, pp. 3494-3502.

Giroux, A., et al., "One Pot Biaryl Synthesis via in situ Boronate Formation," Tet. Lett., 38:22, 3841-3844 (1997).

Goytisolo, et al., "The absence of DNA-dependent protein kinase catalytic subunit in mice results in anaphase bridges and in increased telomeric fusions with normal telomere length and G-strand overhang," Mol. Cell. Biol., 2001, vol. 21, No. 11, pp. 3642-3651.

Green, T. and Wuts, P., ed., "Protective Groups in Organic Synthesis," Wiley (1999) (book not provided).

Griffin, et al., "Selective Benzopyranone and Pyrimido [2,1-a]isoquinolin-4-one Inhibitors of DNA-Dependent Protein Kinase: Synthesis, Structure—Activity Studies, and Radiosensitization of a Humn Tumor Cell Line in Vitro", J. Med. Chem., 2005, 48, 569-585.

Hartley, K. O., et al., "DNA-dependent protein kinase catalytic subunit: a relative of phosphatidylinositol 3-kinase and the ataxia telengiectasia gene product," Cell, 1995, vol. 82, pp. 849-856.

Haselhorst, Dörte, et al., "Development of cell lines stably expressing human immunodeficiency virus type 1 proteins for studies in encapsidation and gene transfer," J. Gen. Virol., 79: 231-237 (1998).

Herzog, Karl-Heinz et al., "Requirement for Atm in Ionizing Radiation-Induced Cell Death in the Developing Central Nervous System," Science, 280: 1089-1091 (1998).

Hickson, Ian, et al, Identification and Characterization of a Novel and Specific Inhibitor of the Ataxia-Telangiectasia Mutated Kinase, ATM, Cancer Research 64, Dec. 15, 2004, 9152-9159.

Hollick, J J, et al., "2,6-Disubstituted pyran-4-one and thiopyran-4-one inhibitors of DNA-dependent protein kinase" Bioorganic and Medicinal Chemistry Letters, vol. 13, No. 18, Sep. 15, 2003 pp. 3083-3086, XP002303369.

Ishiyama, T. et al., "Synthesis of Arylboronates via the Palladium(0)-catalyzed Cross-Coupling Reaction of Tetra(alkoxo) diborons with Aryl Triflates," Tett. Lett., 38:19, 3447-3450 (1997).

Izzard, R.A., et al., "Competitive & noncompetitive inhibition of the DNA-dependent protein kinase," Cancer Research, 1999, vol. 59, No. 11, pp. 2581-2586.

Jackson, S. P., "DNA damage detection by DNA dependent protein kinase and related enzymes," Cancer Surv., 1996, vol. 28, pp. 261-279.

Jung, J. C., et al., "Simple and cost effective synthesis of 4-hydroxycoumarin," Synth. Commun., 1999, vol. 29, No. 20, pp. 3587-3595.

Keith, Curtis, T. and Schreiber, Stuart L., "PIK-Related Kinases: DNA Repair, Recombination, and Cell Cycle Checkpoints," Science, 270: 50-51 (1995).

Knight, A.R., et al., "Isolation and characterization of 4-chloro-3,4'; 3',4"-tercoumarin," Can. J. Chem., 1968, vol. 46, pp. 2495-2499.

Kubik, et al., "Fine tuning of the cation affinity of artificial receptors based on cyclic peptides by intramolecular conformational control," Eur. J. Org. Chem., 2001, pp. 311-312.

Lavin, Martin F. and Shiloh, Yosef, "The genetic defect in ataxia-telangiectasia," Annu. Rev. Immunol., 15:177-202 (1997).

Leahy, et al., "Identification of a highly potent and selective DNA-dependent protein kinase (DNA-PK) inhibitor (NU7441) by screening of chromenone librariest", Bioorganic & Medicinal Chemistry Letters 14 (2004) 6083-6087.

Metcalfe, Judith A. et al., "Accelerated telomere shortening in ataxia telangiectasia," Nature Genetics, 13: 350-353 (1996).

Mlotkowska, B.L. et al., "Two-Dimensional NMR Studies of 2-Substituted Thioxanthene Sulfoxides," J. Heterocyclic Chem., 28: 731-736 (Apr.-May 1991).

Morris, J., et al., "Reaction of phosgeniminium salts with enolates derived from Lewis acid complexes of 2'-hydroxypropiophenones and related β-Diketones," J. Org. Chem., 1996, vol. 61, No. 9, pp. 3218-3220.

Morris, J., et al., "Synthesis of 2-amino-6-phenyl-4H-pyran-4-ones," Synthesis, 1994, pp. 43-46.

Morris, J., et al., "Synthesis and biological evaluation of antiplatelet 2-aminochromones," J. Med. Chem., 1993, vol. 36, No. 14, pp. 2026-2032.

Naldini, Luigi et al., "In Vivo Gene Delivery and Stable Transduction of Nondividing Cells by a Lentiviral Vector," Science, 272: 263-267 (1996).

Oh, C., et al., "Nucleophilic vinylic substitution of halocoumarins and halo-1,4-napthoquinones with morpholine," J. Heterocyclic Chem., 1994, vol. 31, pp. 841-843.

Remington's Pharmaceutical Sciences, 18th ed., Mack Pub. Co., Easton, PA (1990) (book not provided).

Roma, G., et al., "Synthesis, antiplatelet activity and comparative molecular field analysis of substituted 2-amino-4H pyrido[1,2-a]pyrimidin-4-ones, their congeners and isosteric analogues," Bioorganic & Medicinal Chemistry, 2000, vol. 8, pp. 751-768.

Roma, G., et al., "Pyran derivatives XX. 2-aminochromone benzo-fused derivatives with antiproliferative properties," Il Farmaco, 1998, vol. 53, pp. 494-503.

Rosenzweig, K.E., et al., "Radiosensitization of human tumor cells by the phosphatidylinositol 3-kinase inhibitors Wortmannin and LY294002 correlates with inhibition of DNA-dependent protein kinase and prolonged G2-M delay," Clin. Cancer Res., 1999, vol. 3, 1149-1156.

Sarkaria, Jann N. et al., "Inhibition of ATM and ATR Kinase Activities by the Radiosensitizing Agent, Caffeine," Cancer Res., 59: 4375-4382 (1999).

Savitsky, Kinneret et al., "A Single Ataxia Telangiectasia Gene with a Product Similar to PI-3 Kinase," *Science*, 268:1749-1753 (1995).

Schroth, W., et al., "2,4,6-Tris (dialkylamino) pyrylium salts and related systems, synthesis and reaction behavior," *Tetrahedron Letters*, 1988, vol. 29, No. 37, pp. 4695-4698.

Schroth, W. et al., "2,4,6-Tris(dialkylamino) pyrylium salts and related systems, synthesis and reaction behavior," Chemical Abstracts, 110:135031.

Shiloh, Yosef, "ATM and ATR: networking cellular responses to DNA damage," *Curr. Opin. Genet. Dev.*, 11:71-77 (2001).

Skehan, P., et al., "New colorimetric cytotoxicity assay for anticancer-drug screening," *J. Natl. Cancer Inst.*, 1990, vol. 82, No. 13, pp. 1107-1112.

Smith, G. C. M., et al., "The DNA-dependent protein kinase," *Genes & Dev.*, 1999, vol. 13, pp. 916-934.

Snyder, et al., "Structure and reactions of malonyl-α-aminopyridine. I," *J. Am. Soc.*, 1952, vol. 74, pp, 4910-4914.

Ten Hoeve, et al., "Direct substitution of aromatic ethers by lithium amides. A new aromatic amination reaction," *J. Org. Chem.*, 1993, vol. 58, pp. 5101-5106.

Toker, Alex and Cantley, Lewis C., "Signalling through the lipid products of phosphoinositide-3-OH kinase," *Nature*, 387:673-676 (1997).

Veuger, S. J., et al., "Radiosensitization and DNA repair inhibition by the combined use of novel inhibitors of DNA-dependent protein kinase and poly (ADP-ribose) polymerase-1," *Cancer Research*, 2003, vol. 63, pp. 6008-6015.

Vlahos, C. J., et al., "A specific inhibitor of phosphatidylinositol 3-kinase, 2-(4- morpholinyl)-8-phenyl-4H-1-benzopyran-4-one (LY294002)," *J. Biol. Chem.*, 1994, vol. 269, No. 7, pp. 5241-5248.

Willmore, et al., "A novel DNA-dependent protein kinase inhibitor, NU7026, potentiates the cytotoxicity of topoisomerase II posions used in the treatment of leukemia", Blood, Jun. 15, 2004, vol. 103, No. 12, 4659-4665.

Wymann, M. T., et al., "Wortmannin inactivates phosphoinositide-3-kinase by covalent modification of Lys-802, a residue involved in the phosphate transfer reaction," *Mol. Cell Biol.*, 1996, vol. 16, No. 4, pp. 1722-1733.

Zakian, Virginia A., "ATM-Related Genes: What Do They Tell Us About Functions of the Human Gene?" *Cell*, 82:685-687 (1995).

\* cited by examiner

ATM INHIBITORS

CROSS-REFERENCE TO RELATED APPLICATIONS

This application claims the benefit of U.S. provisional patent application number 60/494,776 filed on Aug. 13, 2003, which is herein incorporated by reference.

The present invention relates to compounds which act as ATM inhibitors, their use and synthesis.

Human DNA is constantly under attack from reactive oxygen intermediates principally from by-products of oxidative metabolism. Reactive oxygen species are capable of producing DNA single-strand breaks and, where two of these are generated in close proximity, DNA double strand breaks (DSBs). In addition, single- and double-strand breaks can be induced when a DNA replication fork encounters a damaged template, and are generated by exogenous agents such as ionising radiation (IR) and certain anti-cancer drugs (e.g. bleomycin, etoposide, camptothecin). DSBs also occur as intermediates in site-specific V(D)J recombination, a process that is critical for the generation of a functional vertebrate immune system. If DNA DSBs are left unrepaired or are repaired inaccurately, mutations and/or chromosomal aberrations are induced, which in turn may lead to cell death. To combat the serious threats posed by DNA DSBs, eukaryotic cells have evolved several mechanisms to mediate their repair. Critical to the process of DNA repair is the slowing down of cellular proliferation to allow time for the cell to repair the damage. A key protein in the detection of DNA DSBs and in the signalling of this information to the cell cycle machinery is the kinase ATM (ataxia telangiectasia mutated) (Durocher and Jackson (2001) DNA-PK, ATM and ATR as sensors of DNA damage: variations on a theme? *Curr Opin Cell Biol.*, 13:225-31, Abraham (2001) Cell cycle checkpoint signaling through the ATM and ATR kinases. *Genes Dev.*, 15; 2177-96).

The ATM protein is an ~350 kDa polypeptide that is a member of the phosphatidylinositol (PI) 3-kinase family of proteins by virtue of a putative kinase domain in its carboxyl-terminal region (Savitsky et al (1995) A single ataxia telangiectasia gene with a product similar to PI-3 kinase. *Science*, 268:1749-53). Classical PI 3-kinases, such as PI 3-kinase itself, are involved in signal transduction and phosphorylate inositol lipids that act as intracellular second messengers (reviewed in Toker and Cantley (1997) Signalling through the lipid products of phosphoinositide-3-OH kinase, *Nature*, 387: 673-6). However, ATM bears most sequence similarity with a subset of the PI 3-kinase family that comprises proteins which, like ATM, are involved in cell cycle control and/or in the detection and signalling of DNA damage (Keith and Schreiber (1995) PIK-related kinases: DNA repair, recombination, and cell cycle checkpoints, *Science*, 270; 50-1, Zakian (1995) ATM-related genes: what do they tell us about functions of the human gene? *Cell*, 82; 685-7). Notably there is no evidence to date that any members of this subset of the PI 3-kinase family are able to phosphorylate lipids. However, all members of this family have been shown to possess serine/threonine kinase activity. ATM phosphorylates key proteins involved in a variety of cell-cycle checkpoint signalling pathways that are initiated in response to DNA DSBs production (see below). These downstream effector proteins include p53, Chk2, NBS1/nibrin, BRCA1 and Rad 17 (Abraham, 2001)

ATM is the product of the gene mutated in ataxia-telangiectasia (A-T) (Savitsky et al (1995)). A-T is a human autosomal recessive disorder present at an incidence of around 1 in 100,000 in the population. A-T is characterised by a number of debilitating symptoms, including progressive cerebellar degeneration, occulocutaneous telangiectasia, growth retardation, immune deficiencies, cancer predisposition and certain characteristics of premature ageing (Lavin and Shiloh (1997), The genetic defect in ataxia-telangiectasia. *Annu. Rev. Immunol.*, 15:177-202; Shiloh (2001), ATM and ATR: networking cellular responses to DNA damage, *Curr. Opin. Genet. Dev.*, 11:71-7). At the cellular level, A-T is characterised by a high degree of chromosomal instability, radio-resistant DNA synthesis, and hypersensitivity to ionizing radiation (IR) and radiomimetic drugs. In addition, A-T cells are defective in the radiation induced $G_1$-S, S, and $G_2$-M cell cycle checkpoints that are thought to arrest the cell cycle in response to DNA damage in order to allow repair of the genome prior to DNA replication or mitosis (Lavin and Shiloh, 1997). This may in part reflect the fact that A-T cells exhibit deficient or severely delayed induction of p53 in response to IR. Indeed, p53-mediated downstream events are also defective in A-T cells following IR exposure. ATM therefore acts upstream of p53 in an IR-induced DNA damage signalling pathway. A-T cells have also been shown to accumulate DNA double-strand breaks (dsbs) after ionizing radiation, suggesting a defect in dsb repair.

It is clear that ATM is a key regulator of the cellular response to DNA DSBs. Therefore the inhibition of this kinase through small molecules will sensitise cells to both ionising radiation and to chemotherapeutics that induce DNA DSBs either directly or indirectly. ATM inhibitors may thus be used as adjuncts in cancer radiotherapy and chemotherapy. To date the only reported inhibitors of ATM (caffeine and wortmannin; Sarkaria, et al., (1999) Inhibition of ATM and ATR kinase activities by the radiosensitizing agent, caffeine. *Cancer Res.*, 59:4375-82; Banin, et al., (1998) Enhanced phosphorylation of p53 by ATM in response to DNA damage. *Science*, 281:1674-1677) do cause radiosensitisation but it is unclear whether this mechanism of action is mediated through ATM inhibition as these small molecules are very non-specific in action as kinase inhibitors.

ATM function in response to ionising radiation induced DNA damage has been shown to be tissue specific. For example, while fibroblasts derived from Atm null mice are radiosensitive Atm null neurons are radioresistant through a lack of IR induced apoptosis (Herzog et al., (1998) Requirement for Atm in ionizing radiation-induced cell death in the developing central nervous system. *Science*, 280: 1089-91). Therefore, inhibitors of ATM have the potential to be radioprotective in specific cellular contexts.

ATM inhibitors may also prove useful in the treatment of retroviral mediated diseases. It has been demonstrated that ATM function is required to allow stable retroviral DNA transduction under certain conditions (Daniel et al. (2001) Wortmannin potentiates integrase-mediated killing of lymphocytes and reduces the efficiency of stable transduction by retroviruses. *Mol. Cell Biol.*, 21: 1164-72). Therefore ATM inhibitors have the potential to block retroviral DNA integration.

ATM is known to play a crucial role in controlling the length of telomeric chromosomal ends (Metcalfe et al. (1996) Accelerated telomere shortening in ataxia telangiectasia. *Nat Genet.*, 13:350-3). Telomeric ends in most normal cell types shorten at each cell division. Cells with excessively shortened telomeres are unable to divide. Inhibitors of ATM may therefore, have utility in preventing cancer progression by limiting the growth potential of cancerous or pre-cancerous cells. Furthermore, ATM does not appear to be part of the telomerase enzyme itself (Metcalfe et al. (1996)) Therefore it is likely that ATM inhibitors will work synergistically with anti-telomerase drugs.

Cells derived from A-T patients or from mice null for ATM grow slower in culture than genetically matched ATM positive cells. Therefore an ATM inhibitor may have growth inhibitory/anti-proliferative properties in its own right. Therefore an ATM inhibitor may be used as a cytostatic agent in the treatment of cancer.

A-T patients display immuno-deficiencies, demonstrating that ATM is required for generation of a fully functional immune system. Inhibitors of ATM may, therefore, be used in modulating the immune system.

In summary ATM inhibitors have the potential to sensitise tumour cells to ionising radiation or DNA DSB inducing chemotherapeutics, to modulate telomere length control mechanisms, to block retroviral integration, modulate the immune system and to protect certain cell types from DNA damage induced apoptosis.

Some of the present inventors have previsouly described a broad class of compounds which exhibit inhibition of ATM. These are described in an International Patent application (PCT/GB03/001817, filed 29 Apr. 2003) and a U.S. patent application Ser. No. (10/426147, filed 29 Apr. 2003).

The present inventors have now discovered within that broad class of compounds, further specific classes compounds which exhibit inhibition of ATM. Accordingly, the first aspect of the invention provides a compound of formula I:

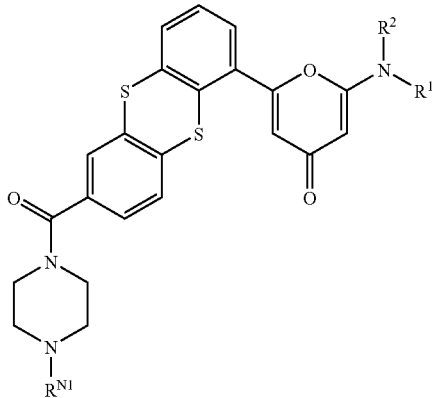

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms; and $R^{N1}$ is selected from hydrogen, an optionally substituted $C_{1-7}$ alkyl group, an optionally substituted $C_{3-20}$ heterocyclyl group, an optionally substituted $C_{5-20}$ aryl group, an acyl group, an ester group and an amido group.

The second aspect of the invention provides a compound of formula II:

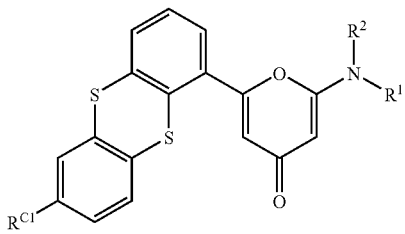

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms;

$R^{C1}$ is —$NR^3R^4$, where $R^3$ and $R^4$ are independently selected from from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms, or $R^{C1}$ is of formula IIa:

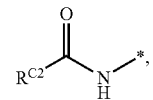

wherein $R^{C2}$ is selected from an optionally substituted $C_{1-7}$ alkyl group, an optionally substituted $C_{3-20}$ heterocyclyl group, an optionally substituted $C_{5-20}$ aryl group, an ester group, an ether group and an amino group.

A third aspect of the invention provides a compound of formula III:

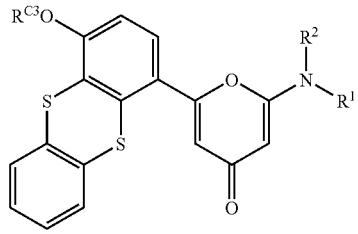

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms;

$R^{C3}$ is of formula:

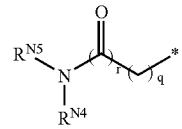

wherein r is 0 or 1, and q can be 1 or 2 when r is 0 and q is 1 when r is 1, and wherein $R^{N4}$ and $R^{N5}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms.

A fourth aspect of the invention provides a compound of formula IV:

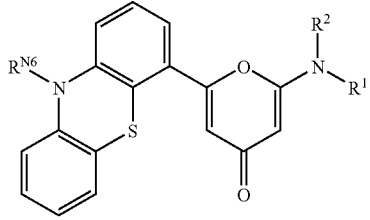

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms;

$R^{N6}$ is of formula:

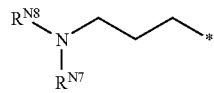

wherein $R^{N7}$ and $R^{N8}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms.

A fifth aspect of the invention provides a compound of formula V:

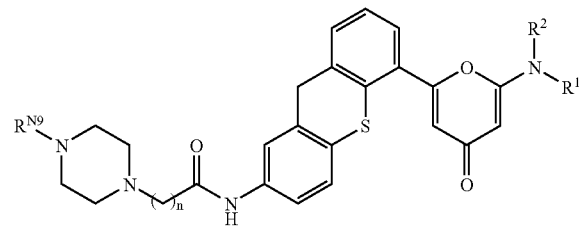

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms;

n is 1 or 2; and $R^{N9}$ is selected from hydrogen, an optionally substituted $C_{1-7}$ alkyl group, an optionally substituted $C_{3-20}$ heterocyclyl group, an optionally substituted $C_{5-20}$ aryl group, an acyl group, an ester group or an amido group;

with the proviso that $R^{N9}$ is not an unsubstituted methyl group.

A sixth aspect of the present invention provides a compound of formula VI:

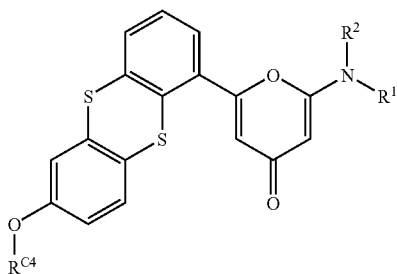

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms; and $R^{C4}$ is of formula:

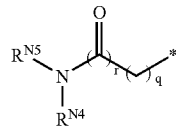

wherein r is 0 or 1, and q can be 1 or 2 when r is 0 and q is 1 when r is 1, and wherein $R^{N4}$ and $R^{N5}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms.

A seventh aspect of the present invention provides a compound of formula VII:

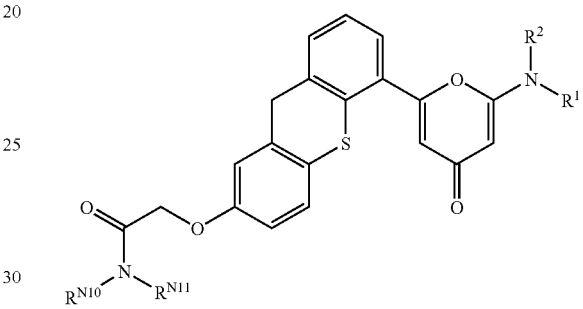

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms; and $R^{N10}$ and $R^{N11}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms.

An eight aspect of the present invention provides a compound of formula VIII:

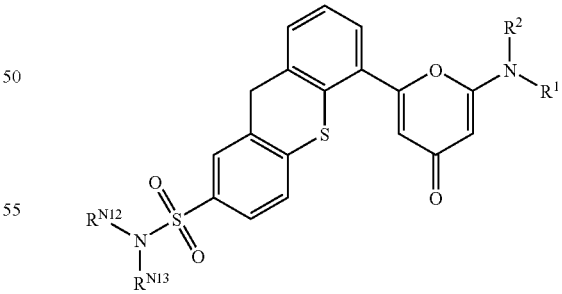

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms; and $R^{N12}$ and $R^{N13}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms.

A ninth aspect of the present invention provides a compound of formula IX:

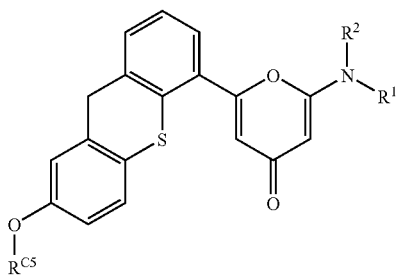

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms; and
$R^{C5}$ is of formula:

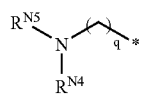

wherein q is 1 or 2, and
wherein $R^{N4}$ and $R^{N5}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms.

A tenth aspect of the invention provides a composition comprising a compound of any one of the first to ninth aspects and a pharmaceutically acceptable carrier or diluent.

An eleventh aspect of the invention provides the use of a compound of any one of the first to ninth aspects in a method of therapy.

A twelfth aspect of the invention provides the use of a compound of any one of the first to ninth aspects in the preparation of a medicament for inhibiting the activity of ATM.

A thirteenth aspect of the invention provides for the use of a compound as defined in one of the first to ninth aspects of the invention in the preparation of a medicament for use as an adjunct in cancer therapy or for potentiating tumour cells for treatment with ionising radiation or chemotherapeutic agents.

A fourteenth aspect of the invention provides for the use of a compound as defined in any one of the first to ninth aspects of the invention in the preparation of a medicament for the treatment of retroviral mediated diseases or disease ameliorated by the inhibition of ATM, which include acquired immunodeficiency syndrome.

A further aspect of the invention provides an active compound as described herein for use in a method of treatment of the human or animal body, preferably in the form of a pharmaceutical composition.

Another aspect of the invention provides a method of inhibiting ATM in vitro or in vivo, comprising contacting a cell with an effective amount of an active compound as described herein.

Definitions $C_{1-7}$ alkyl: The term "$C_{1-7}$ alkyl", as used herein, pertains to a monovalent moiety obtained by removing a hydrogen atom from a $C_{1-7}$ hydrocarbon compound having from 1 to 7 carbon atoms, which may be aliphatic or alicyclic, or a combination thereof, and which may be saturated, partially unsaturated, or fully unsaturated.

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic $C_{1-7}$ alkyl groups (also referred to as "$C_{3-7}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of unsaturated $C_{1-7}$ alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon-carbon double bonds (also referred to as "$C_{3-7}$ cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$ heterocyclyl: The term "$C_{3-20}$ heterocyclyl", as used herein, pertains to a monovalent moiety obtained by removing a hydrogen atom from a ring atom of a $C_{3-20}$ heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, pyrrolidines (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine.

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, pyran ($C_6$), and oxepin. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulphur ring atom include, but are not limited to, those derived from thiirane, thietane, thiolane (tetrahydrothiophene), thiane (tetrahydrothiopyran), and thiepane.

Examples of $C_{3-20}$ heterocyclyl groups having two oxygen ring atoms include, but are not limited to, those derived from dioxolane, dioxane, and dioxepane.

Examples of $C_{3-20}$ heterocyclyl groups having two nitrogen ring atoms include, but are not limited to, those derived from imidazolidine, pyrazolidine (diazolidine), imidazoline, pyrazoline (dihydropyrazole), and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroisoxazole, morpholine, tetrahydrooxazine, dihydrooxazine, and oxazine.

Examples of $C_{3-20}$ heterocyclyl groups having one oxygen ring atom and one sulphur ring atom include, but are not limited to, those derived from oxathiolane and oxathiane (thioxane).

Examples of $C_{3-20}$ heterocyclyl groups having one nitrogen ring atom and one sulphur ring atom include, but are not limited to, those derived from thiazoline, thiazolidine, and thiomorpholine.

Other examples of $C_{3-20}$ heterocyclyl groups include, but are not limited to, oxadiazine and oxathiazine.

Examples of heterocyclyl groups which additionally bear one or more oxo (=O) groups, include, but are not limited to, those derived from:

$C_5$ heterocyclics, such as furanone, pyrone, pyrrolidone (pyrrolidinone), pyrazolone (pyrazolinone), imidazolidone, thiazolone, and isothiazolone;

$C_6$ heterocyclics, such as piperidinone (piperidone), piperidinedione, piperazinone, piperazinedione, pyridazinone, and pyrimidinone (e.g., cytosine, thymine, uracil), and barbituric acid;

fused heterocyclics, such as oxindole, purinone (e.g., guanine), benzoxazolinone, benzopyrone (e.g., coumarin);

cyclic anhydrides (—C(=O)—O—C(=O)— in a ring), including but not limited to maleic anhydride, succinic anhydride, and glutaric anhydride;

cyclic carbonates (—O—C(=O)—O— in a ring), such as ethylene carbonate and 1,2-propylene carbonate;

imides (—C(=O)—NR—C(=O)— in a ring), including but not limited to, succinimide, maleimide, phthalimide, and glutarimide;

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam, γ-butyrolactam (2-pyrrolidone), δ-valerolactam, and ε-caprolactam;

cyclic carbamates (—O—C(=O)—NR— in a ring), such as 2-oxazolidone;

cyclic ureas (—NR—C(=O)—NR— in a ring), such as 2-imidazolidone and pyrimidine-2,4-dione (e.g., thymine, uracil).

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g. fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups", in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), naphthacene ($C_{18}$), and pyrene ($C_{16}$).

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulphur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

Examples of $C_{5-20}$ heteroaryl groups which comprise fused rings, include, but are not limited to, $C_9$ heterocyclic groups derived from benzofuran, isobenzofuran, indole, isoindole, purine (e.g., adenine, guanine), benzothiophene, benzimidazole; $C_{10}$ heterocyclic groups derived from quinoline, isoquinoline, benzodiazine, pyridopyridine, quinoxaline; $C_{13}$ heterocyclic groups derived from carbazole, dibenzothiophene, dibenzofuran; $C_{14}$ heterocyclic groups derived from acridine, xanthene, phenoxathiin, phenazine, phenoxazine, phenothiazine.

The above $C_{1-7}$ alkyl, $C_{3-20}$ heterocyclyl, and $C_{5-20}$ aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OCH$_3$ (methoxy), —OCH$_2$CH$_3$ (ethoxy) and —OC(CH$_3$)$_3$ (tert-butoxy)

$C_{1-2}$ alkdioxylene: The term "$C_{1-2}$ alkdioxylene," as used herein, pertains to a bidentate moiety obtained by removing two hydrogen atoms from each of two different alcohol groups of a $C_{1-2}$ hydrocarbon diol compound having from 1 or 2 carbon atoms, i.e. CH$_2$(OH)$_2$ and HO—CH$_2$—CH$_2$—OH, to form —O—CH$_2$—O— and —O—CH$_2$—CH$_2$—O—. This bidentate moiety may be the substituent group of a single atom or of two adjacent atoms.

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl and phthalimidyl:

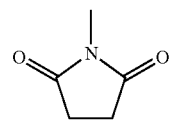 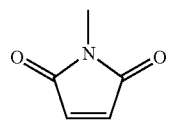 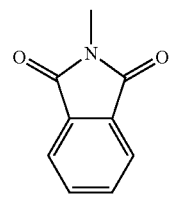

succinimidyl     maleimidyl     phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Tetrazolyl: a five membered aromatic ring having four nitrogen atoms and one carbon atom,

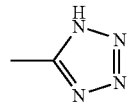

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, hydrogen, a $C_{1-7}$ alkyl group, a $C_{3-20}$ heterocyclyl group, or a $C_{5-20}$ aryl group, preferably H or a $C_{1-7}$ alkyl group.

Amidine: —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. An example of an amidine group is —C(=NH)NH$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$, —S(=O)$_2$C$_4$F$_9$ (nonaflyl), —S(=O)$_2$CH$_2$CF$_3$ (tresyl), —S(=O)$_2$Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH and —S(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$. A special class of sulfonamino groups are those derived from sultams —in these groups one of R$^1$ and R is a C$_{5-20}$ aryl group, preferably phenyl, whilst the other of R$^1$ and R is a bidentate group which links to the C$_{5-20}$ aryl group, such as a bidentate group derived from a C$_{1-7}$ alkyl group. Examples of such groups include, but are not limited to:

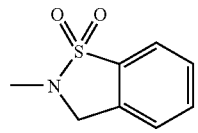

2,3-dihydro-tenzo[d] isothiazole-1,1-dioxide-2-yl

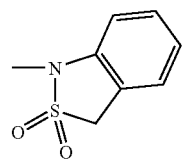

1,3-dihydro-benzo[c]isothiazole-2,2-dioxide-1-yl

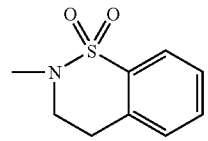

3,4-dihydro-2H-benzo[e][1,2]thiazine-1,1-dioxide-2-yl

Phosphoramidite: —OP (OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

In many cases, substituents may themselves be substituted. For example, a Cl$_7$ alkoxy group may be substituted with, for example, a C$_{1-7}$ alkyl (also referred to as a C$_{1-7}$ alkyl-C$_{1-7}$ alkoxy group), for example, cyclohexylmethoxy, a C$_{3-20}$ heterocyclyl group (also referred to as a C$_{5-20}$ aryl-C$_{1-7}$ alkoxy group), for example phthalimidoethoxy, or a C$_{5-20}$ aryl group (also referred to as a C$_{5-20}$aryl-C$_{1-7}$alkoxy group), for example, benzyloxy.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

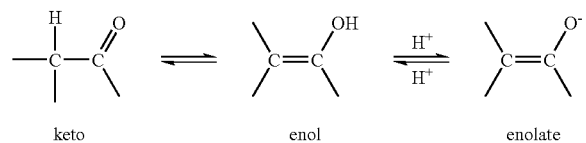

keto            enol            enolate

Note that specifically included in the term "isomer" are compounds with one or more isotopic substitutions. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts", *J. Pharm. Sci.*, Vol . 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH₃, —OAc).

For example, an aldehyde or ketone group may be protected as an acetal or ketal, respectively, in which the carbonyl group (>C=O) is converted to a diether (>C(OR)₂), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH₃); a benzyloxy amide (—NHCO—OCH₂C₆H₅, —NH-Cbz); as a t-butoxy amide (—NHCO—OC(CH₃)₃, —NH-Boc); a 2-biphenyl-2-propoxy amide (—NHCO—OC(CH₃)₂C₆H₄C₆H₅, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an $C_{1-7}$ alkyl ester (e.g. a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH₂NHC(=O)CH₃).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$ alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Further Preferences

The following preferences may be different for different aspects of the present invention, and may be combined together.

In formulae I, II, III, IV, V, VI, VII, VIII and IX, $R^1$ and $R^2$ form, along with the nitrogen atom to which they are attached, a heterocyclic ring having from 4 to 8 atoms. This may form part of a $C_{4-20}$ heterocyclyl group defined above (except with a minimum of 4 ring atoms), which must contain at least one nitrogen ring atom. It is preferred that $R^1$ and $R^2$ form, along with the nitrogen atom to which they are attached, a heterocyclic ring having 5, 6 or 7 atoms, more preferably 6 ring atoms.

Single rings having one nitrogen atom include azetidine, azetidine, pyrrolidine (tetrahydropyrrole), pyrroline (e.g., 3-pyrroline, 2,5-dihydropyrroe), 2H-pyrrole or 3H-pyrrole (isopyrrole, isoazole), piperidine, dihydropyridine, tetrahydropyridine, and azepine; two nitrogen atoms include imidazolidine, pyrazolidine (diazolidine), imidazoline, pyrazoline (dihydropyrazole), and piperazine; one nitrogen and one oxygen include tetrahydrooxazole, dihydrooxazole, tetrahydroisoxazole, dihydroisoxazole, morpholine, tetrahydrooxazine, dihydrooxazine, and oxazine; one nitrogen and one sulphur include thiazoline, thiazolidine, and thiomorpholine.

Preferred rings are those containing one heteroatom in addition to the nitrogen, and in particular, the preferred heteroatoms are oxygen and sulphur. Thus preferred groups include morpholino, thiomorpholino, thiazolinyl. Preferred groups without a further heteroatom include pyrrolidino.

The most preferred groups are morpholino and thiomorpholino.

As mentioned above, these heterocyclic groups may themselves be substituted; a preferred class of substituent is a $C_{1-7}$ alkyl group. When the heterocyclic group is morpholino, the substituent group or groups are preferably methyl or ethyl, and more preferably methyl. A sole methyl substituent is most preferably in the 2 position.

As well as the single ring groups listed above, rings with bridges or cross-links are also envisaged. Examples of these types of ring where the group contains a nitrogen and an oxygen atom are:

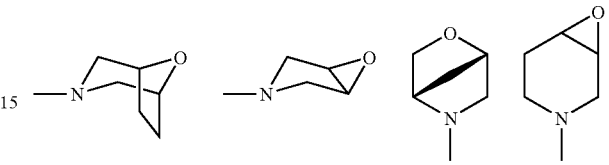

These are named 8-oxa-3-aza-bicyclo[3.2.1]oct-3-yl, 6-oxa-3-aza-bicyclo[3.1.0]hex-3-yl, 2-oxa-5-aza-bicyclo [2.2.1]hept-5-yl, and 7-oxa-3-aza-bicyclo[4.1.0]hept-3-yl, respectively.

First Aspect

Preferably $R^{N1}$ is selected from hydrogen, an optionally substituted $C_{1-7}$ alkyl group, an optionally substituted $C_{5-20}$ aryl group, an acyl group and an ester group.

If $R^{N1}$ is an optionally substituted $C_{1-7}$ alkyl group, it is preferably an optionally substituted $C_{1-4}$ alkyl group, and more preferably an optionally substituted $C_{1-2}$ alkyl group. The optional substituents are preferably selected from hydroxyl, $C_{1-7}$ alkoxy (e.g. methoxy, ethoxy), acyl and amido.

If $R^{N1}$ is an optionally substituted $C_{5-7}$ aryl group, it is preferably an optionally substituted carboaryl or heteroaryl (containing 1 or 2 nitrogen ring atoms) group and more preferably an optionally substituted phenyl, pyridyl or pyrimidyl group. It is further preferred that the $C_{5-7}$ aryl group is unsubstituted.

If $R^{N1}$ is an acyl group, then the acyl substituent is preferably a $C_{1-7}$ alkyl group (more preferably $C_{1-4}$ alkyl, e.g. methyl) or a $C_{5-7}$ aryl group (more preferably $C_{5-6}$ aryl, e.g. furanyl, thiophenyl, phenyl, pyridyl).

If $R^{N1}$ is an ester group, the ester substituents is preferably a $C_{1-7}$ alkyl group (more preferably $C_{1-4}$ alkyl, e.g. methyl, t-butyl).

Particularly preferred $R^{N1}$ groups include, but are not limited to, 2-fluoro phenyl and furan-2-yl.

Second Aspect $R^{C1}$ is preferably of formula IIa.

If $R^{C1}$ is —NR$^3$R$^4$, then R$^3$ and R$^4$ are preferably selected from optionally substituted $C_{1-7}$ alkyl groups and more preferably optionally substituted $C_{1-4}$ alkyl groups. It is most preferred that one, or both, of R$^3$ and R$^4$ is hydrogen.

$R^{C2}$ is preferably selected from an optionally substituted $C_{1-7}$ alkyl group, an optionally substituted $C_{3-20}$ heterocyclyl group, an optionally substituted $C_{5-20}$ aryl group and an ester group, and is more preferably selected from an optionally substituted $C_{1-7}$ alkyl group and an optionally substituted $C_{3-20}$ heterocyclyl group.

If $R^{C2}$ is an ester group, the ester substituent is preferably a $C_{1-7}$ alkyl group (more preferably a $C_{1-4}$ alkyl group, e.g. methyl).

If $R^{C2}$ is an optionally substituted $C_{3-20}$ heterocyclyl group, it is preferably an optionally substituted $C_{5-7}$ heterocylyl group, and more preferably contains at least one nitrogen ring atom (e.g. 4-piperidyl).

If $R^{C2}$ is an optionally substituted $C_{5-20}$ aryl group, then it is preferably an optionally substituted $C_{5-6}$ aryl group. More preferably, it is selected from optionally substituted phenyl or a $C_{5-6}$ heteroaryl group containing one or two heteroatoms selected from nitrogen, oxygen and sulphur (e.g. pyridyl, thiazolyl, furanyl, thiophenyl, isoxazolyl, 1,2-diazolyl).

If $R^{C2}$ is an optionally substituted $C_{1-7}$ alkyl group, it is preferably an optionally substituted $C_{1-4}$ alkyl group (e.g. methyl, ethyl, propyl, cyclopropyl, cyclobutyl). Preferable optional substituents include, but are not limited to, amino, thioether, ester, $C_{5-20}$ aryl, $C_{3-20}$ heterocyclyl, acyloxy, ether and alkoxy.

In one embodiment, $R^{C2}$ is of formula IIb:

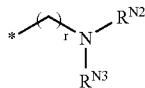

wherein r is from 1 to 3 (more preferably 1 or 2); and $R^{N2}$ and $R^{N3}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms.

More preferably $R^{N2}$ and $R^{N3}$ are independently selected from hydrogen, optionally substituted $C_{1-7}$ alkyl groups or together form, along with the nitrogen atom to which they are attached, an optionally substituted heterocyclic ring having from 4 to 8 ring atoms.

If one of $R^{N2}$ and $R^{N3}$ is an optionally substituted $C_{1-7}$ alkyl group, the other is preferably H. The optionally substituted $C_{1-7}$ alkyl group, is preferably an optionally substituted $C_{1-4}$ alkyl group (e.g. methyl, ethyl, n-propyl, n-butyl). The optional substituents are preferably selected from hydroxy, $NH_2$, $C_{3-20}$ heterocylyl (more preferably $C_{5-7}$ heterocylyl) and $C_{5-20}$ aryl (more preferably $C_{5-7}$ aryl)

If $R^{N2}$ and $R^{N3}$ together form, along with the nitrogen atom to which they are attached, an optionally substituted heterocyclic ring having from 4 to 8 ring atoms, this ring preferably has 6 or 7 ring atoms, and is more preferably selected from piperidine, piperazine, homopiperazine and morpholino. Where the heterocyclic ring is piperazine or homopiperazine, the other nitrogen ring atom may be susbstituted by, for example, an optionally substituted $C_{1-7}$ alkyl group, an optionally substituted $C_{3-20}$ heterocyclyl group, an optionally substituted $C_{5-20}$ aryl group, an acyl group, an ester group or an amido group. Of these possible substituents, the optionally substituted $C_{1-7}$ alkyl group (e.g. methyl), the optionally substituted $C_{5-20}$ aryl group (e.g. phenyl) and the acyl group are more preferred.

Third Aspect $R^{C3}$ may be of formula:

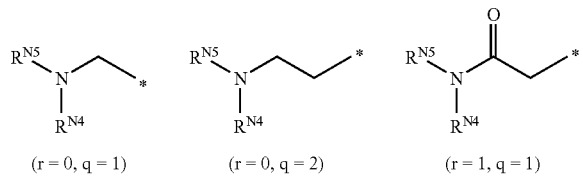

It is preferred that r=0.

More preferably $R^{N4}$ and $R^{N5}$ are independently selected from hydrogen, optionally substituted $C_{1-7}$ alkyl groups, or together form, along with the nitrogen atom to which they are attached, an optionally substituted heterocyclic ring having from 4 to 8 ring atoms.

If one of $R^{N4}$ and $R^{N5}$ is an optionally substituted $C_{1-7}$ alkyl group, the other is preferably H. The optionally substituted $C_{1-7}$ alkyl group, is preferably an optionally substituted $C_{1-4}$ alkyl group (e.g. methyl, ethyl, n-propyl, n-butyl). The optional substituents are preferably selected from hydroxy, amino, cyano, $C_{3-20}$ heterocylyl (more preferably $C_{5-7}$ heterocylyl) and $C_{5-20}$ aryl (more preferably $C_{5-7}$ aryl).

In one embodiment, one of $R^{N4}$ and $R^{N5}$ is of formula IIb:

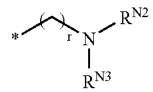

as defined above.

If $R^{N4}$ and $R^{N5}$ together form, along with the nitrogen atom to which they are attached, an optionally substituted heterocyclic ring having from 4 to 8 ring atoms, this ring preferably has 6 or 7 ring atoms, and is more preferably selected from piperidine, homopiperidine, piperazine, homopiperazine and morpholino. Where the heterocyclic ring is piperazine or homopiperazine, the other nitrogen ring atom may be susbstituted by, for example, an optionally substituted $C_{1-7}$ alkyl group, an optionally substituted $C_{3-20}$ heterocyclyl group, an optionally substituted $C_{5-20}$ aryl group, an acyl group, an ester group or an amido group. Of these possible substituents, the optionally substituted $C_{1-7}$ alkyl group (e.g. methyl), the optionally substituted $C_{5-20}$ aryl group (e.g. phenyl) and the acyl group are more preferred.

Fourth Aspect $R^{N7}$ and $R^{N8}$ are preferably independently selected from hydrogen, optionally substituted $C_{1-7}$ alkyl groups and optionally substituted $C_{3-20}$ heterocyclyl groups, or together form, along with the nitrogen atom to which they are attached, an optionally substituted heterocyclic ring having from 4 to 8 ring atoms.

More preferably $R^{N7}$ and $R^{N8}$ are independently selected from hydrogen, optionally substituted $C_{1-7}$ alkyl groups or together form, along with the nitrogen atom to which they are attached, an optionally substituted heterocyclic ring having from 4 to 8 ring atoms.

If one of $R^{N7}$ and $R^{N8}$ is an optionally substituted $C_{1-7}$ alkyl group, the other is preferably H. The optionally substituted $C_{1-7}$ alkyl group, is preferably an optionally substituted $C_{1-4}$ alkyl group (e.g. methyl, ethyl, n-propyl, n-butyl). The optional substituents are preferably selected from hydroxy, halo, amino, $C_{4-7}$ cycloalkyl, $C_{3-20}$ heterocylyl (more preferably $C_{5-7}$ heterocylyl) and $C_{5-20}$ aryl (more preferably $C_{5-7}$ aryl).

In one embodiment, one of $R^{N7}$ and $R^{N8}$ is of formula IIb:

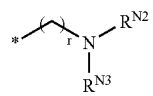

as defined above.

If $R^{N7}$ and $R^{N8}$ together form, along with the nitrogen atom to which they are attached, an optionally substituted heterocyclic ring having from 4 to 8 ring atoms, this ring preferably has 5 to 7 ring atoms, and is more preferably selected from pyrrole, piperidine, piperazine, homopiperazine and morpholino. Where the heterocyclic ring is piperazine or homopiperazine, the other nitrogen ring atom may be susbstituted by, for example, an optionally substituted $C_{1-7}$ alkyl group, an optionally substituted $C_{3-20}$ heterocyclyl group, an optionally substituted $C_{5-20}$ aryl group, an acyl group, an ester group or an amido group. Of these possible substituents, the optionally substituted $C_{1-7}$ alkyl group (e.g. methyl), the optionally substituted $C_{5-20}$ aryl group (e.g. phenyl) and the acyl group are more preferred. Where the heterocyclic ring does not include a further nitrogen ring atom, the ring may be further substituted by one or more substituent groups, for example, but not limited to, $C_{1-7}$ alkyl, amido, hydroxy and ester.

Fifth Aspect $R^{N9}$ is preferably selected from hydrogen, an optionally substituted $C_{1-7}$ alkyl group, an optionally substituted $C_{3-20}$ heterocyclyl group, an optionally substituted $C_{5-20}$ aryl group, or an acyl group; with the proviso that $R^{N9}$ is not an unsubstituted methyl group.

If $R^{N9}$ is an optionally substituted $C_{1-7}$ alkyl group, it is preferably an optionally substituted $C_{1-4}$ alkyl group, and more preferably an optionally substituted $C_{1-2}$ alkyl group. The optional substituents are preferably selected from hydroxyl, $C_{1-7}$ alkoxy (e.g. methoxy, ethoxy), acyl and amido.

If $R^{N9}$ is an optionally substituted $C_{5-7}$ aryl group, it is preferably an optionally substituted carboaryl or heteroaryl (containing 1 or 2 nitrogen ring atoms) group and more preferably an optionally substituted phenyl, pyridyl or pyrimidyl group. It is further preferred that the $C_{5-7}$ aryl group is unsubstituted.

If $R^{N9}$ is an acyl group, then the acyl substituent is preferably a $C_{1-7}$ alkyl group (more preferably $C_{1-4}$ alkyl, e.g. methyl) or a $C_{5-7}$ aryl group (more preferably $C_{5-6}$ aryl, e.g. furanyl, thiophenyl, phenyl, pyridyl).

Particularly preferred $R^{N9}$ groups include, but are not limited to, 4-fluoro phenyl, ethyl and 2-(2'-hydroxy-ethoxy)-ethyl.

Sixth Aspect $R^{C4}$ may be of formula:

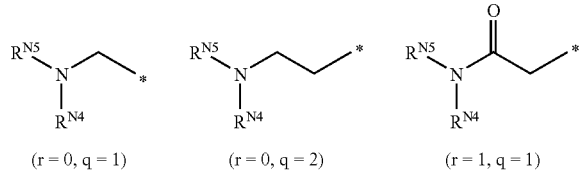

(r = 0, q = 1)     (r = 0, q = 2)     (r = 1, q = 1)

It is preferred that r=0.

More preferably $R^{N4}$ and $R^{N5}$ are independently selected from hydrogen, optionally substituted $C_{1-7}$ alkyl groups, or together form, along with the nitrogen atom to which they are attached, an optionally substituted heterocyclic ring having from 4 to 8 ring atoms.

If one of $R^{N4}$ and $R^{N5}$ is an optionally substituted $C_{1-7}$ alkyl group, the other is preferably H. The optionally substituted $C_{1-7}$ alkyl group, is preferably an optionally substituted $C_{1-4}$ alkyl group (e.g. methyl, ethyl, n-propyl, n-butyl). The optional substituents are preferably selected from hydroxy, halo, $C_{1-7}$ alkoxy (e.g. methoxy), thiol, $C_{1-7}$ thioether (e.g. —SMe), amino, ester (preferably $C_{1-7}$ alkyl ester, e.g. —C(=O)OMe), cyano, $C_{3-20}$ heterocylyl (more preferably $C_{5-7}$ heterocylyl) and $C_{5-20}$ aryl (more preferably $C_{5-7}$ aryl).

In one embodiment, one of $R^{N4}$ and $R^{N5}$ is of formula IIb:

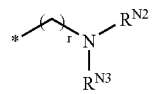

as defined above.

If $R^{N4}$ and $R^{N5}$ together form, along with the nitrogen atom to which they are attached, an optionally substituted heterocyclic ring having from 4 to 8 ring atoms, this ring preferably has 6 or 7 ring atoms, and is more preferably selected from piperidine, homopiperidine, piperazine, homopiperazine and morpholino. Where the heterocyclic ring is piperazine or homopiperazine, the other nitrogen ring atom may be susbstituted by, for example, an optionally substituted $C_{1-7}$ alkyl group, an optionally substituted $C_{3-20}$ heterocyclyl group, an optionally substituted $C_{5-20}$ aryl group, an acyl group, an ester group or an amido group. Of these possible substituents, the optionally substituted $C_{1-7}$ alkyl group (e.g. methyl), the optionally substituted $C_{5-20}$ aryl group (e.g. phenyl) and the acyl group are more preferred.

Seventh Aspect

Preferably $R^{N10}$ and $R^{N11}$ are independently selected from hydrogen, optionally substituted $C_{1-7}$ alkyl groups or together form, along with the nitrogen atom to which they are attached, an optionally substituted heterocyclic ring having from 4 to 8 ring atoms.

If one of $R^{N10}$ and $R^{N11}$ is an optionally substituted $C_{1-7}$ alkyl group, the other is preferably H. The optionally substituted $C_{1-7}$ alkyl group, is preferably an optionally substituted $C_{1-4}$ alkyl group (e.g. methyl, ethyl, n-propyl, n-butyl). The optional substituents are preferably selected from hydroxy, halo, cyano, $NH_2$, $C_{1-7}$ alkoxy (e.g. methoxy), $C_{1-7}$ thioether (e.g. —SMe), $C_{3-20}$ heterocylyl (more preferably $C_{5-7}$ heterocylyl) and $C_{5-20}$ aryl (more preferably $C_{5-7}$ aryl)

If $R^{N10}$ and $R^{N11}$ together form, along with the nitrogen atom to which they are attached, an optionally substituted heterocyclic ring having from 4 to 8 ring atoms, this ring preferably has 6 or 7 ring atoms, and is more preferably selected from piperidine, homopiperadine, piperazine, homopiperazine, morpholino and thiomorpholino. These groups may be optionally substituted, for example by an optionally substituted $C_{1-7}$ alkyl or amido groups.

Where the heterocyclic ring is piperazine or homopiperazine, the other nitrogen ring atom may be susbstituted by, for example, an optionally substituted $C_{1-7}$ alkyl group, an optionally substituted $C_{3-20}$ heterocyclyl group, an optionally substituted $C_{5-20}$ aryl group, an acyl group, an ester group or an amido group. Of these possible substituents, the optionally substituted $C_{1-7}$ alkyl group (e.g. methyl), the optionally substituted $C_{5-20}$ aryl group (e.g. phenyl) and the acyl group are more preferred.

Eighth Aspect

Preferably $R^{N12}$ and $R^{N13}$ are independently selected from hydrogen, optionally substituted $C_{1-7}$ alkyl groups or together form, along with the nitrogen atom to which they are attached, an optionally substituted heterocyclic ring having from 4 to 8 ring atoms.

If one of $R^{N12}$ and $R^{N13}$ is an optionally substituted $C_{1-7}$ alkyl group, the other is preferably H. The optionally substituted $C_{1-7}$ alkyl group, is preferably an optionally substituted $C_{1-4}$ alkyl group (e.g. methyl, ethyl, n-propyl, n-butyl). The optional substituents are preferably selected from hydroxy, halo, cyano, $NH_2$, $C_{1-7}$ alkoxy (e.g. methoxy), $C_{1-7}$ thioether (e.g. —SMe), $C_{3-20}$ heterocylyl (more preferably $C_{5-7}$ heterocylyl) and $C_{5-20}$ aryl (more preferably $C_{5-7}$ aryl)

If $R^{N12}$ and $R^{N13}$ together form, along with the nitrogen atom to which they are attached, an optionally substituted heterocyclic ring having from 4 to 8 ring atoms, this ring preferably has 6 or 7 ring atoms, and is more preferably selected from piperidine, homopiperadine, piperazine, homopiperazine, morpholino and thiomorpholino. These groups may be optionally substituted, for example by an optionally substituted $C_{1-7}$ alkyl or amido groups. Where the heterocyclic ring is piperazine or homopiperazine, the other nitrogen ring atom may be susbstituted by, for example, an optionally substituted $C_{1-7}$ alkyl group, an optionally substituted $C_{3-20}$ heterocyclyl group, an optionally substituted $C_{5-20}$ aryl group, an acyl group, an ester group or an amido group. Of these possible substituents, the optionally substituted $C_{1-7}$ alkyl group (e.g. methyl), the optionally substituted $C_{5-20}$ aryl group (e.g. phenyl) and the acyl group are more preferred.

Ninth Aspect $R^{C5}$ may be of formula:

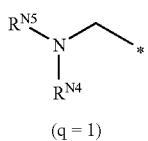
(q = 1)

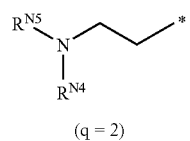
(q = 2)

It is preferred that q=2.

More preferably $R^{N4}$ and $R^{N5}$ are independently selected from hydrogen, optionally substituted $C_{1-7}$ alkyl groups.

If one of $R^{N4}$ and $R^{N5}$ is an optionally substituted $C_{1-7}$ alkyl group, the other is preferably H. The optionally substituted $C_{1-7}$ alkyl group, is preferably an optionally substituted $C_{1-4}$ alkyl group (e.g. methyl, ethyl, n-propyl, n-butyl). The optional substituents are preferably selected from hydroxy, amino, cyano, $C_{3-20}$ heterocylyl (more preferably $C_{5-7}$ heterocylyl) and $C_{5-20}$ aryl (more preferably $C_{5-7}$ aryl).

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), acetyl (Ac), 1,3-bis(diphenylphosphino) propane (dppf).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis Routes

Compounds of the present invention may be synthesised by the coupling of a 2-chloro-6-amino-pyran-4-one to an appropriate arylboronic acid or arylboronate ester using a palladium catalysed coupling reaction, e.g. Suzuki coupling.

Synthesis of 2-chloro-6-amino-pyran-4-ones

These may be synthesised by the following route:

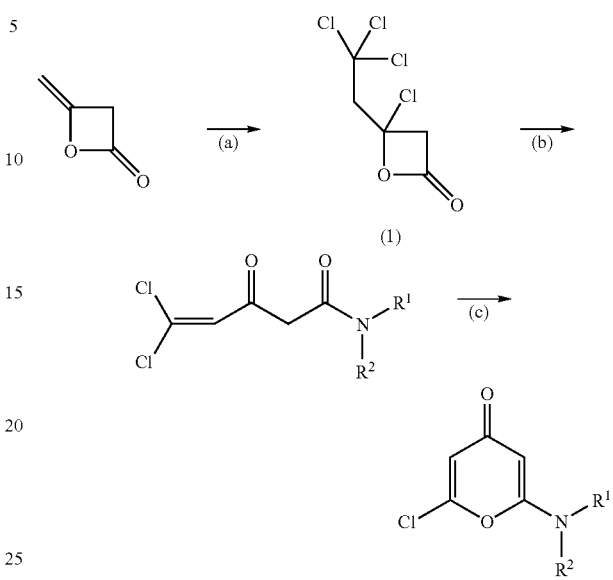

In step (a) CCl$_4$ is added across the carbon-carbon double bond of diketene by free-radical addition to yield 4-chloro-4 (2,2,2,-trichloro-ethyl)-oxetan-2-one (1). Suitable initiators include peroxide, such as BCHPO ((bis-4-t-butylcyclohexyl) peroxydicarbonate).

In step (b), the amine R$^1$R$^2$NH opens the lactone ring by nucleophilic attack at the carbonyl centre. The oxy anion generated then displaces the chlorine atom on the a-carbon to give rise to a β-keto-amide intermediate. Further elimination of HCl finally give the 5,5-dichloro-1-amino-pent-4-ene-1,3-dione. Suitable conditions for this step include inorganic base such as sodium hydrogen carbonate and solvent such as dry dichloromethane.

In step (c), ring closure takes place by displacement of one of the 5-chloro groups by the oxygen of the amide moiety to form the pyran-4-one ring, which reaction is catalysed by a Lewis acid, such as perchloric acid.

Arylboronic Acids and Arylboronate Esters

The appropriate arylboronic acids and arylboronate esters may be synthesised by using one of the routes described in the examples below. General synthesis steps are shown below.

Synthesis of Aryl Boronate Esters

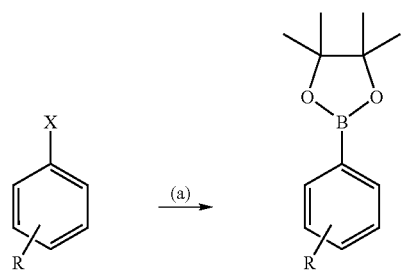

X = TfO, Br, I
(a): PdCl2dppf, dppf, Pinacol diborane, KOAc
where R is the remainder of the group Aryl boronate esters may be formed by Pd(0)-catalysed cross coupling reaction of the appropriate aryl triflate or aryl halide with tetra(alkoxy)diboron, e.g. pinacol diboron. Suitable conditions include the use of a catalyst, such as PdCl₂dppf, extra ligands, such as dppf, potassium acetate as a base, in a solvent such as dioxane, DMF or DMSO.

Examples of this method are to be found in T Ishiyama, et al., *Tet. Lett.*, vol. 38, no. 19, 3447-3450, 1997 and A Giroux, et al., *Tet. Lett.*, vol. 38, no. 22, 3841-3844, 1997.

Synthesis of Aryl Boronic Acids

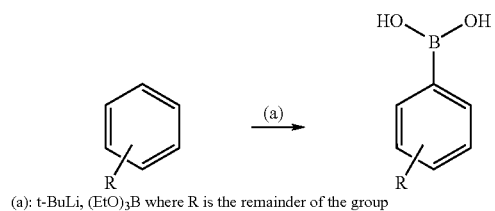

(a): t-BuLi, (EtO)₃B where R is the remainder of the group

Boronic acids may be generated via lithiation of the aromatic ring by tert-butyl lithium followed by the reaction of the anion formed with alkyl borate such as triethyl borate to give the desired aryl boronic acid.

Palladium Catalysed Coupling

The coupling of the arylboronic acid or arylboronate ester to the 2-chloro-6-amino-pyran-4-one can be carried out using the normal conditions, e.g. a palladium catalyst (Pd(PPh₃)₄, Pd(dppf)Cl₂) and base (Na₂CO₃, NaOCH₂CH₃, TlOH, N(CH₂CH₃)₃, K₃PO₄)

Use of Compounds of the Invention

The present invention provides active compounds, specifically, active 2-aryl-6-amino-pyran-4-ones.

The term "active", as used herein, pertains to compounds which are capable of inhibiting ATM activity, and specifically includes both compounds with intrinsic activity (drugs) as well as prodrugs of such compounds, which prodrugs may themselves exhibit little or no intrinsic activity.

One assay which may be used in order to assess the ATM inhibition offered by a particular compound is described in the examples below.

The present invention further provides a method of inhibiting ATM in a cell, comprising contacting said cell with an effective amount of an active compound, preferably in the form of a pharmaceutically acceptable composition. Such a method may be practised in vitro or in vivo.

For example, a sample of cells (e.g. from a tumour) may be grown in vitro and an active compound brought into contact with said cells in conjunction with agents that have a known curative effect, and the enhancement of the curative effect of the compound on those cells observed.

The present invention further provides active compounds which inhibit ATM activity as well as methods of inhibiting ATM activity comprising contacting a cell with an effective amount of an active compound, whether in vitro or in vivo.

The invention further provides active compounds for use in a method of treatment of the human or animal body. Such a method may comprise administering to such a subject a therapeutically-effective amount of an active compound, preferably in the form of a pharmaceutical composition.

The term "treatment" as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage form comprising an active compound, which is effective for producing some desired therapeutic effect, commensurate with a reasonable benefit/risk ratio.

The term "adjunct" as used herein relates to the use of active compounds in conjunction with known therapeutic means. Such means include cytotoxic regimens of drugs and/or ionising radiation as used in the treatment of different cancer types. In particular, the active compounds are known to potentiate the actions of a number of cancer chemotherapy treatments, which include, but are not limited to, the topoisomerase class of poisons and any chemotherapeutic that will induce a DNA double strand break used in treating cancer. Topoisomerase I inhibitors that may be used in combination with compounds of the invention include the camptothecin compounds, e.g. topotecan (Hycamtin), irinotecan (CPT11—Camptosar), rubitecan and exatecan. Dual Topoisomerase I and II inhibitors that may be used in combination with compounds of the invention include benzophenainse, XR 11576/MLN 576 and benzopyridoindoles. Topoisomerase II inhibitors that may be used in combination with compounds of the invention include the intercalators and DNA binders Doxorubicin, Danorubicin, and other rubicins, the acridines (Amsacrine, m-AMSA), plus Mitoxantrone and AQ4. Non-intercalators which are topoisomerase II inhibitors include Etopside and Teniposide (epipodophyllotoxins).

The present inventors have previously found that ATM inhibitory compounds of similar structure to those of the present invention can efficiently repress retroviral vector transduction in one-step, cell based integration assays (termed LUCIA) and inhibit HIV-1 infection in 4-day replication assays at sub-micromolar concentrations. Further, in contrast to the observations of Daniel et al., where it was concluded that the effect of ATM on retroviral integration would only be seen in a DNA-PK-deficient background, this effect works in the presence of functional DNA-PK activity.

Initial linkage of linear retroviral DNA with host cell chromosomal DNA is catalysed by viral integrase (IN) and results in short staggered DNA strand breaks in the host cell DNA at the site of attachment (Brown, P. O. (1990) Integration of retroviral DNA. *Curr Top Microbiol Immunol*, 157, 19-48). These gapped DNA intermediates are shown to be sensed as sites of DNA damage by the host cell and repaired by the ATM pathway to complete the process of integration and allow productive infection to occur. Compounds of the invention would be able to prevent the repair of gapped DNA intermediates by the ATM pathway and thus prevent complete integration of retroviral DNA into the host genome.

As described above, the invention provides a compound as defined in the first to ninth aspects of the invention for use in the treatment of retroviral infection and the use of such a compound in the manufacture of a medicament for use in the treatment of retroviral infection.

Also provided by the invention is a method of treatment of a retroviral infection comprising administering a compound as defined in the first to ninth aspects of the invention to an individual in need thereof.

Retroviral mediated diseases which may be treated as described above include HIV infection and acquired immunodeficiency syndrome (AIDS) and Human T-cell Leukaemia virus (HTLV) infection and its associated diseases adult T-cell leukaemia/lymphoma (ATLL) and tropical spastic paraparesis/HTLV-1 associated myelopathy (TSP/HAM).

Compounds of the invention may be used in combination with other retroviral therapies to suppress virus replication, for example in a 'highly active anti-retroviral therapy' or HAART treatment.

The invention provides a pharmaceutical composition comprising a compound as described herein and one or more other anti-retroviral agents.

The invention also provides a composition comprising a compound as defined in the first to ninth aspects of the invention and one or more other anti-retroviral agents for treatment of a retroviral infection and the use of such a composition in the manufacture of a medicament for use in the treatment of a retroviral infection.

Suitable anti-retroviral agents which inhibit retroviral replication, for example retroviral protease inhibitors (PI) such as Sequinavir, Indinavir, Ritonavir and Nelfinavir, nucleoside retroviral reverse transcriptase inhibitors such as 3'-azido-3'deoxythymidine (AZT; Zidovudine), 2',3'-Dideoxycytosine (ddC; Zalcitabine), 2',3'-Dideoxyinosine (ddI; Didanosine)and 3TC; (Lamivudine), and non-nucleoside retroviral reverse transcriptase inhibitors such as Nevirapine, Delavirdine and Efavirenz.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18to edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low.

Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

A) Chemical Examples

General Experimental Methods

Thin layer chromatography was carried out using Merck Kieselgel 60 $F_{254}$ glass backed plates. The plates were visualized by the use of a UV lamp (254 nm). Silica gel 60 (particle sizes 40-63μ) supplied by E. M. Merck was employed for flash chromatography. $^1$H NMR spectra were recorded at 300 MHz on a Bruker DPX-300 instrument. Chemical shifts were referenced to tetramethylsilane.

Purification and Identification of Libraries Samples

The samples were purified on Gilson LC units. Mobile phase A—0.1% aqueous TFA, Mobile phase B—Acetonitrile, Flow rate 6 ml/min. Gradient—typically starting at 90% A/10% B for one minute, rising to 97% B after 15 minutes, holding there for 2 minutes, then back to the starting conditions. Column: Jones Chromatography Genesis 4μ C18 column, 10 mm×250 mm. Peak acquisition based on UV detection at 254 nm.

Mass Specs were recorded on a Finnegan LCQ instrument in positive ion mode.

Mobile phase A—0.1% aqueous formic acid, Mobile phase B—Acetonitrile, Flow rate 2 ml/min., Gradient—starting at 95% A/5% B for one minute, rising to 98% B after 5 minutes, holding there for 3 minutes, then back to the starting conditions. Column—Phenomenex 5μ Luna C18 column, 4.6 mm×50 mm UV detection at 254 nm, PDA detection scanning from 210 to 600 nm.

Mass Spectra of Other Compounds

Mass spectra of non-library compounds and building blocks were recorded on a Micromass ZQ instrument (single quadrupole, operating in electrospray ionisation mode), using a Waters 600 HPLC Pump and 2700 Autosampler.

Mobile Phase A: 0.1% Formic acid in water, Mobile phase B: 0.1% Formic acid in acetonitrile, Flow rate: 2.0 ml/min., Gradient: 5% B to 95% B over 3 mins, hold 3 mins. Column: Varies, but always C18 50 mm×4.6 mm (Currently Genesis C18 4μ. Jones Chromatography). PDA detection: Waters 996, scan range 210-400 nm.

Synthesis of 2-Chloro-6-morpholin-4-yl-pyran-4-one (3)

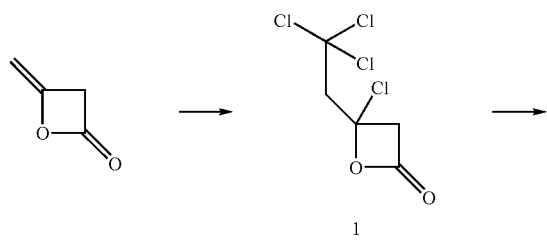

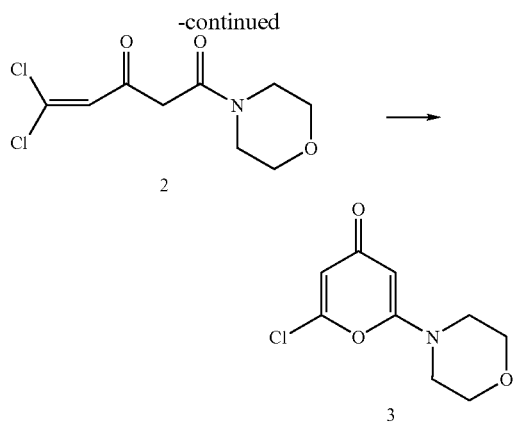

4-Chloro-4-(2,2,2-trichloro-ethyl)-oxetan-2-one (1)

A solution of BCHPO (bis-4-t-butylcyclohexyl)peroxydicarbonate (11.8 g) and diketene (83.5 ml) in $CCl_4$ (300 ml) was added dropwise over 120 minutes to a refluxing solution of CCl4, and was stirred for a further 1 hour. The resulting pale yellow solution was cooled and azeotroped with DCM. The resulting residue was stirred with hexane (3×150 ml) for 10 minutes and the liquor was decanted off through a celite pad. The filtered liquors were combined and concentrated in vacuo to give 1 as a pale yellow oil (125.0 g, 52.9%).

5,5-Dichloro-1-morpholin-4-yl-pent-4-ene-1,3-dione (2)

Two separate solutions of 1 (62.5 g, 0.26 mmol) and morpholine (24.0 g, 0.28 mol) in DCM (120 ml) were added simultaneously to a mixture of $NaHCO_3$ (44.0 g, 0.52 mol) in dry DCM (300 ml). The reaction was maintained at 15° C. over 140 minutes with stirring. The reaction was filtered, washed with DCM (3×100 ml) and the combined organic layers were concentrated in vacuo to a slurry which was then passed through a short silica pad, and further washed with DCM (4×100 ml). The combined organic layers were concentrated in vacuo, suspended in hexane (400 ml) and stirred for 1 hour, filtered and dried to give a cream solid. The solid was suspended in TBME (100 ml), stirred for 15 minutes, filtered, washed with TBME and dried to give 2 as a white powder (47.8 g, 72%). m/z (LC-MS, ESP): 252 ($M^+$+1).

2-Chloro-6-morpholin-4-yl-pyran-4-one (3)

To a suspension of 2 (11.3 g, 44.9 mmol) in dioxane was added perchloric acid (11.4 ml, 0.14 mol) and the reaction was heated at 90° C. under $N_2$ for 1 hour. The reaction was cooled, neutralised with 2M NaOH (75 ml) and filtered. The aqueous layer was extracted with DCM (4×30 ml) and the organic layers were combined and dried over $MgSO_4$. The organic layer was further treated with charcoal and filtered through celite. The dark yellow filtrate was evaporated in vacuo, and the resulting solid was triturated with hexane (50 ml) and dried to give 3 (7.3 g, 75%) as a light yellow powder. m/z (LC-MS, ESP): 216 ($M^+$+1). $^1$H-NMR (300 MHz, DMSO-$d_6$): 3.3 (t, 4H), 3.65 (t, 4H), 5.4 (d, 1H), 6.25 (d, 1H).

Example 1

6-(6-Morpholin-4-yl-4-oxo-4H-pyran-2-yl)-thian-threne-2-carboxylic acid amide Derivatives

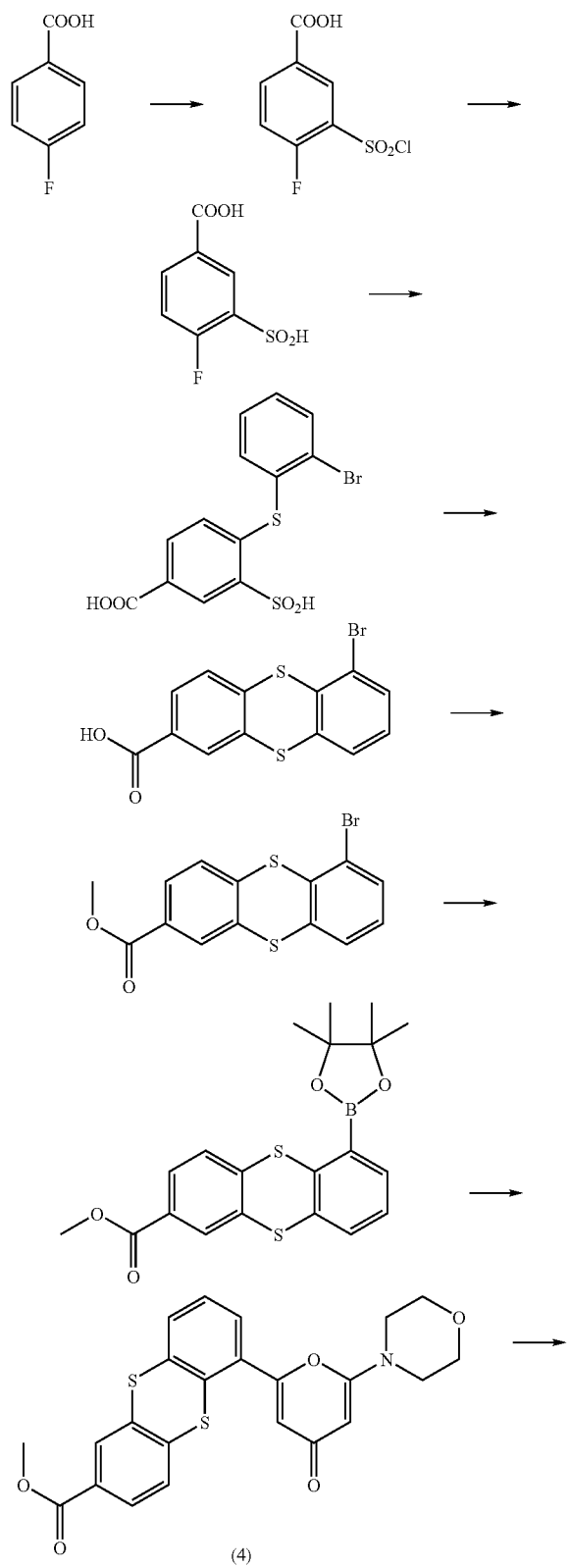

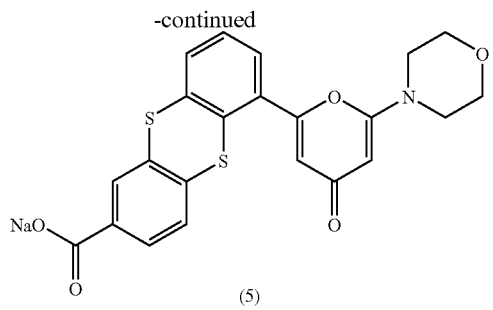

3-Chlorosulfonyl-4-fluoro-benzoic acid

Chlorosulphonic acid (100 ml, 1.5 mol) was gradually added to 4-fluorobenzoic acid (43 g, 0.307 mol) with stirring. The clear dark yellow mixture was heated to 150° C. for 24 hours. The yellow solution was cooled back to room temperature and poured onto ice with vigorous stirring. The white precipitate was filtered and pressed dry. The solid was dried overnight in a desiccator under vacuum and over activated silica (54.65 g, 75%). Mp: 116-117° C.; m/z (LC-MS, ESP), RT=4.03 min, (M$^-$−1)=237-239 (ratio 1:3).

4-Fluoro-3-sulfino-benzoic acid

Sodium sulphite (130 g, 1.034 mol) was added slowly to a solution of 3-chlorosulfonyl-4-fluoro-benzoic acid (49.39 g, 0.207 mol) in water (150 ml) at 0° C. with a vigorous stirring. After the addition was completed the reaction was warmed back to room temperature for 1 hour and the pH of the solution was kept around pH 6-7 with 2N sodium hydroxide solution. The white milky suspension was filtered and the solid washed with 2N sodium hydroxide solution (150 ml) and then water (100 ml). The filtrate was then cooled in an ice bath and concentrated HCl was added until no more precipitate was formed (pH<1). The white precipitate was then filtered, pressed dry and left in a dessicator overnight under vacuum and over activated silica (27.92 g, 66%). m/z (LC-MS, ESP), RT=0.98 min, (M$^-$−1)=203

4-(2-Bromo-phenylsulfanyl)-3-sulfino-benzoic acid

2-Bromobenzenethiol (25 g, 132 mmol) was added to a solution of 4-fluoro-3-sulfino-benzoic acid (13.5 g, 66 mmol) and NaOH pellets (11 g, 264 mmol) in water (30 ml). The yellow mixture was then degassed for 10 minutes and then heated to 140° C. for 48 hours. The reaction was then cooled to 0° C. and acidified to pH 4-5 (pH paper) with concentrated HCl. The precipitate formed was filtered, washed with hexane and was dried in a vacuum dessicator over activated silica overnight (20.69 g, 84%). m/z (LC-MS, ESP), RT=3.67 min, M$^-$−1=373.

6-Bromo-thianthrene-2-carboxylic acid 4-(2-bromo-phenylsulfanyl)-3-sulfino-benzoic acid (14 g, 38 mmol) was added slowly to a stirred solution of methane-sulphonic acid (160 ml). The purple solution was heated to 60° C. for 3 hours. The reaction was cooled down to room temperature and was poured into ice (300 ml) where an off-white precipitate appeared. The solid was filtered and washed with water (100 ml) and then dried in a vacuum dessicator over activated silica (9.48 g, 73%). $^1$HNMR (300MHz, CDCl$_3$): $\delta_H$=7.29 (1H, t), 7.59 (1H, dd), 7.70 (1H,dd) 7.74 (1H, d), 7.87 (1H, dd), 8.03 (1H, d).m/z (LC-MS, ESP), RT=4.99 min, M$^-$−1)=339

6-Bromo-thianthrene-2-carboxylic acid methyl ester

To 6-bromo-thianthrene-2-carboxylic acid (9 g, 28 mmol) in methanol (180 ml) was slowly added conc. H$_2$SO$_4$ (5 ml). The milky white suspension was heated to 80° C. until all the solid had gone into solution (2 hrs). The suspension was concentrated in vacuo. Water (100 ml) was added and the organics were then extracted with dichloromethane (3×70 ml), dried over MgSO4 and evaporated in vacuo, yielding to a yellow solid. (4.48 g, 45%). $^1$HNMR (300 MHz, CDCl$_3$): $\delta_H$=3.94 (3H, s); 7.13 (1H, t), 7.44 (1H, dd), 7.54 (1H, dd) 7.61 (1H, d), 7.93 (1H, dd), 8.13 (1H, d).

6-(4,4,5,5-Tetramethyl-[1,3,2]dioxaborolan-2-yl)-thianthrene-2-carboxylic acid methyl ester 6-Bromo-thianthrene-2-carboxylic acid methyl ester (1 g, 2.8 mmol), bis(pinacolato)diboron (0.86 g, 3.4 mmol) and potassium acetate (0.12 g, 0.14 mmol) in 1,4-dioxane (15 ml) was degassed for 15 minutes. To the yellow suspension was then added PdCl$_2$(dppf) (78 mg, 0.14 mmol) and dppf (0.83 g, 8.5 mmol). The dark red mixture was heated to 90° C. under a N$_2$ atmosphere for 48 hours. The crude mixture was purified by flash chromatography (dichloromethane) to give viscous brown oil (1.13 g), which was used without any further purification.

6-(6-Morpholin-4-yl-4-oxo-4H-pyran-2-yl)-thianthrene-2-carboxylic acid methyl ester (4)

6-(4,4,5,5-Tetramethyl-[1,3,2]dioxaborolan-2-yl)-thianthrene-2-carboxylic acid methyl ester (1.1 g, 2.83 mmol), 2-chloro-6-morpholin-4-yl-pyran-4-one (3) (0.73 g, 3.4 mmol) and K$_2$CO$_3$ (0.8 g, 5.66 mmol) were dissolved in dry 1,4-dioxane (7 ml). The mixture was degassed for 15 mins and Pd(PPh$_3$)$_4$ (0.16 g, 5 mol %) was then added The dark brown mixture was heated to 90° C. under an atmosphere of N$_2$ for 24 hour. The reaction mixture was concentrated in vacuo and water (100 ml) was added. The brown solid was filtered and washed with water (1.23 g, 96%). m/z (LC-MS, ESP), RT=4.49 min, (M$^+$+1)=454.

6-(6-Morpholin-4-yl-4-oxo-4H-pyran-2-yl)-thianthrene-2-carboxylate sodium salt (5)

6-(6-Morpholin-4-yl-4-oxo-4H-pyran-2-yl)-thianthrene-2-carboxylic acid methyl ester (1.1 g, 2.43 mmol) and NaOH Pellets (97 mg, 2.43 mmol) were dissolved in methanol (40 ml). The brown suspension was heated to 80° C. under N$_2$ for 24 hours. The solvent was removed in vacuo and the residue was triturated with diethyl ether. The product was collected by filtration as a fine dark brown powder (1.11 g, 99%). m/z (LC-MS, ESP), RT=3.90 min, (M$^+$+1)=438

6-(6-Morpholin-4-yl-4-oxo-4H-pyran-2-yl)-thianthrene-2-carboxylic acid amide Derivatives 6-(6-morpholin-4-yl-4-oxo-4H-pyran-2-yl)-thianthrene-2-carboxylate sodium salt (138)(20 mg, 0.04 mmol), HBTU (18 mg, 0.05 mmol), di-isopropylethylamine (9 µl, 0.05 mmol), the appropriate amine (0.04 mmol) and dry dimethylacetamide (0.5 ml). The dark brown mixture was stirred at room temp for 2 hours and then purified by preparative HPLC to give the desired products, which are shown below:

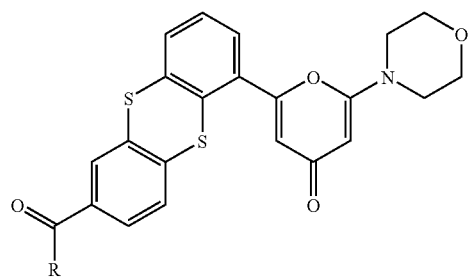

| Compound | R | Purity (%) | Retention Time (Mins) | M$^+$ + 1 |
|---|---|---|---|---|
| 6 | methylpiperazinyl | 95 | 3.14 | 522 |
| 7 | 2-methylphenylpiperazinyl | 90 | 4.92 | 598 |

-continued
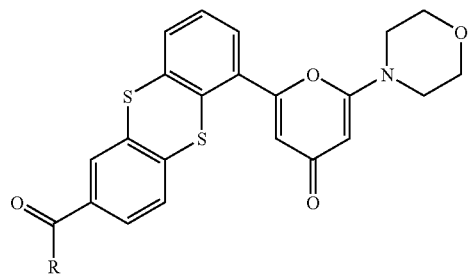
| Compound | R | Purity (%) | Retention Time (Mins) | M⁺ + 1 |
|---|---|---|---|---|
| 8 | 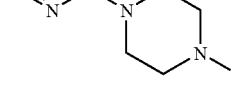 | 90 | 3.37 | 585 |
| 9 | 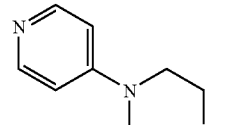 | 90 | 3.28 | 585 |
| 10 | 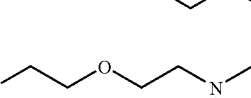 | 95 | 3.12 | 596 |
| 11 | 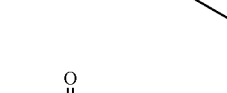 | 95 | 3.52 | 550 |
| 12 | 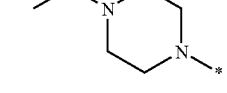 | 85 | 5.16 | 612 |
| 13 | 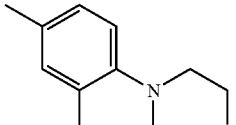 | 95 | 4.08 | 586 |
| 14 | 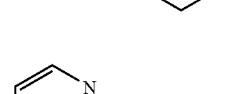 | 95 | 3.28 | 607 |

-continued
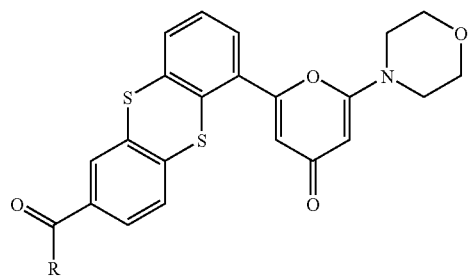
| Compound | R | Purity (%) | Retention Time (Mins) | M+ + 1 |
|---|---|---|---|---|
| 15 | 2-fluorophenyl-piperazinyl | 95 | 4.66 | 602 |
| 16 | Boc-piperazinyl | 95 | 4.36 | 608 |
| 17 | 2-methoxyethyl-piperazinyl | 90 | 3.18 | 566 |
| 18 | furan-2-carbonyl-piperazinyl | 95 | 3.81 | 602 |
| 19 | piperazinyl | 90 | 3.12 | 508 |
| 20 | morpholinoacetyl-piperazinyl | 90 | 3.16 | 635 |

Example 2

2-(7-Amino-thianthren-1-yl)-6-morpholin-4-yl-pyran-4-one amide derivatives

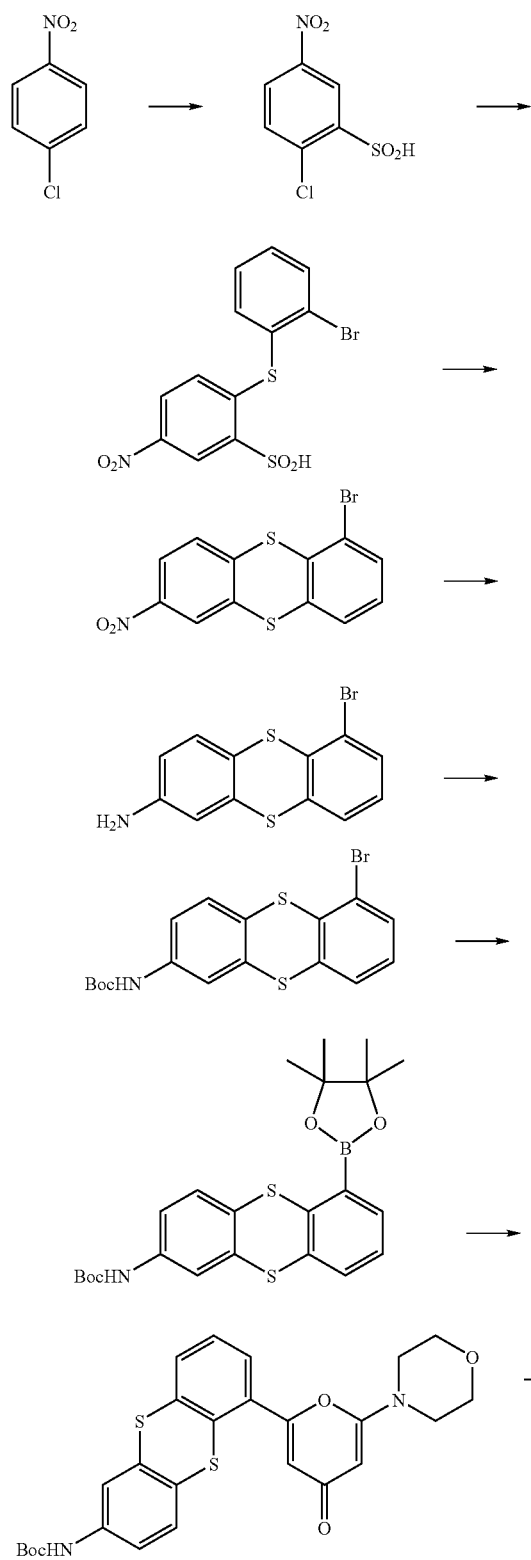

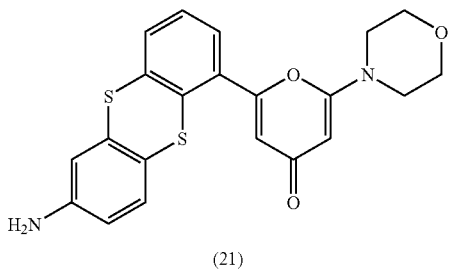

(21)

2-Chloro-5-nitro-benzenesulfinic acid

A solution of 1-chloro-4-nitrobenzene (476 g, 3.02 mol) in chlorosulfonic acid (1 litre) was stirred and heated at 120° C. for 22 hours. The reaction was cooled to room temperature and was poured slowly with stirring onto ice (10 litres). The resulting dark brown precipitate was filtered, pressed dry, dried in a vacuum desiccators over night and was used without any further purification (770 g). The resulting 2-chloro-5-nitro-benzenesulfonyl chloride was suspended in water and cooled to 0° C. (ice bath). Sodium sulphite (1.9 Kg, 15 mol) was added to the stirred solution by portion (100 g portion and in a manner that the temperature remains under 25° C.). After the addition the mixture was allowed to warm back to room temperature and left stirring for one hour. During that time the pH of the solution was kept at pH 7-8 (Whattman pH paper) by addition of 8 M solution of sodium hydroxide (400 ml). The solution was then diluted with water (6 L) and sodium hydroxide was added to it (8 M, 0.5 L). The resulting mixture was filtered through a sintered funnel (number 3). The filtrate was cooled to 0° C. (ice bath) and acidify with concentrated HCl to pH<1. The brown solution then turn green and a silvery green plates precipitate. The solid was filtered, pressed dry and dried in a vacuum desiccator to give the title compound (213 g, 32%).

2-(2-Bromo-phenylsulfanyl)-5-nitro-benzenesulfinic acid

To a solution of NaOH (80.18 g, 2.004 mol) in water (600 ml sonicated and degassed) was added 2-bromothiophenol (108.23 ml, 1.002 mol) and 2-chloro-5-nitro-benzenesulfinic acid (222.11 g, 1.002 mol). The mixture was stirred and heated at 125° C. for 19 hours. The reaction was cooled down at 0° C., and concentrated HCl added dropwise from a dropping funnel while stirring until pH<1. The precipitate formed was filtered, dried in a desiccators overnight and was used without any further purification (417.77 g). m/z (LC-MS, ESP), RT=3.51 min, (M$^-$−1)=372-374, (1:1, bromine isotope ratio present).

1-Bromo-7-nitro-thianthrene 2-(2-Bromo-phenylsulfanyl)-5-nitro-benzenesulfinic acid (208.5 g, 557 mmol) thinly ground was dissolved slowly in methanesulfonic acid (2 litre) with stirring. The mixture was stirred and heated at 50° C. for 17 hours. The solution was poured onto ice (5 L) with stirring, then filtered and the solid collected. The residue was suspended in water (500 ml) and then basified to pH 8 with concentrated ammonia. The solid was then filtered, suspended into methanol (1 L) and filtered again. The solid was then dried in a desiccator under vacuum to give the title compound (115 g, 61%). m/z (LC-MS, ESP), RT=5.53 min (no ionisation). ¹HNMR (300 MHz, CDCl₃): $\delta_H$=7.15 (1H, t), 7.45 (1H, dd), 7.58 (1H, dd), 7.67 (1H, d), 8.11 (1H, dd), 8.31 (1H, d).

6-Bromo-thianthren-2-ylamine

Zn dust (144.1 g, 2.2 mol) was added to a stirred solution of 1-bromo-7-nitro-thianthrene (125 g, 367.4 mmol) in glacial acetic acid (500 ml at 0° C. (ice bath). After one hour the ice bath was removed and the solution was left to react overnight at room temperature. The mixture was filtered through a pad of Celite and washed with copious amount of dichloromethane and the filtrate was evaporated in vacuo. Water was added (500 ml) to the residue and the pH was adjusted to pH 8 by addition of concentrated ammonia. The solid formed was filtered and dried in a vacuum desiccator to give the title compound (118.5 g) and was used without any further purification. m/z (LC-MS, ESP), RT=4.92, (M⁺+1)=310-312 (1:1, bromine isotope ratio present)

(6-Bromo-thianthren-2-yl)-carbamic acid tert-butyl ester

Di-tert-butyl dicarbonate (100 g, 0.458 mol) was added to a solution of 6-bromo-thianthren-2-ylamine (118.51 g, 0.382 mol) in dry THF (500 ml). The mixture was stirred and heated at 50° C. overnight. The solvent was removed in vacuo and the residue was triturated in methanol to give the title compound as a pale brown solid (40.87 g, 26%). ¹HNMR (300 MHz, CDCl₃): $\delta_H$=1.51 (9H, s); 6.50 (1H, bs); 7.08 (1H, t); 7.16 (1H, dd); 7.43 (2H, m); 7.51 (1H, dd); 7.71 (1H, d).

[6-(6-Morpholin-4-yl-4-oxo-4H-pyran-2-yl)-thianthren-2-yl]-carbamic acid tert-butyl ester (6-Bromo-thianthren-2-yl)-carbamic acid tert-butyl ester (7.48 g, 18.24 mmol), bis(pinacolato)diboron (6.48 g, 25.54 mmol) and potassium acetate (6.27 g, 63.84 mmol) in 1,4-dioxane (50 ml). To the yellow suspension was then added PdCl₂(dppf) (745 mg, 0.91 mmol) and dppf (506 mg, 0.91 mmol). The dark red mixture was heated to 110° C. under a N₂ atmosphere for 24 hours. The crude mixture was purified by flash chromatography (silica, dichloromethane) to give [6-(4,4,5,5-Tetramethyl-[1,3,2]dioxaborolan-2-yl)-thianthren-2-yl]-carbamic acid tert-butyl ester as a viscous brown oil which was used without any further purification.
[6-(4,4,5,5-Tetramethyl-[1,3,2]dioxaborolan-2-yl)-thianthren-2-yl]-carbamic acid tert-butyl ester (8.34 g, 18.24 mmol), 2-chloro-6-morpholin-4-yl-pyran-4-one (3)(4.72 g, 21.89 mmol) and grinded K₂CO₃ (5.04 g, 36.48 mmol) were dissolved in dry 1,4-dioxane (100 ml). The mixture was degassed for 15 minutess and Pd(PPh₃)₄ (1.02 g, 0.91 mmol) was then added The dark brown mixture was heated to 100° C. under an atmosphere of N₂ for 24 hour. The reaction mixture was concentrated in vacuo and water (100 ml) was added. The brown solid was filtered, washed with water, dried overnight in a vacuum desiccator and was used without any further purification to give the title compound (11.87 g). m/z (LC-MS, ESP), RT=4.61 min, (M⁺+1)=511.2

2-(7-Amino-thianthren-1-yl)-6-morpholin-4-yl-pyran-4-one (21)

To a solution of [6-(6-morpholin-4-yl-4-oxo-4H-pyran-2-yl)-thianthren-2-yl]-carbamic acid tert-butyl ester (11.95 g, 23.4 mmol) in dichloromethane (150 ml) was added trifluoroacetic acid (30 ml) and left under stirring at room temperature overnight. The solvent was dried in vacuo revealing a viscous dark brown liquid. Saturated sodium bicarbonate solution (400 ml) was added to the residue, which was left to stir for 20 minutes. The brown precipitate was filtered, washing with water and left to dry in a vacuum desiccator overnight. The solid was then purified by column chromatography (silica, MeOH/Dichloromethane, 3:97, Rf=0.28). ¹HNMR (300 MHz, CDCl₃): $\delta_H$=3.24 (2H, bs); 3.46 (4H, bs); 3.81 (4H, bs); 6.33 (1H, s); 6.58 (1H, m); 6.86 (1H, d); 7.21 (1H, d); 7.30 (1H, t); 7.38 (1H, d); 7.63 (1H, d); m/z (LC-MS, ESP), RT=3.8 min, (M⁺+1)=411

2-(7-Amino-thianthren-1-yl)-6-morpholin-4-yl-pyran-4-one amide derivatives

To a small test tube was added 2-(7-amino-thianthren-1-yl)-6-morpholin-4-yl-pyran-4-one (21)(20 mg, 0.05 mmol), dry dimethylacetamide (0.5 ml), triethylamine (0.01 ml, 0.08 mmol) and the desired acid chloride (0.08 mmol) with stirring overnight. The reaction was purified by preparative HPLC to give the desired products, which are shown below:

| Compound | R | Purity (%) | Retention Time (Mins) | M⁺ + 1 |
|---|---|---|---|---|
| 22 | —\* | 95 | 3.73 | 453 |
| 23 | methoxyacetyl | 95 | 3.91 | 483 |
| 24 | cyclopropyl | 95 | 4.08 | 479 |
| 25 | benzo[1,3]dioxol-5-yl | 95 | 4.45 | 559 |
| 26 | methyl butanoate | 95 | 4.03 | 539 |
| 27 | 4-cyanophenyl | 95 | 4.44 | 540 |

-continued

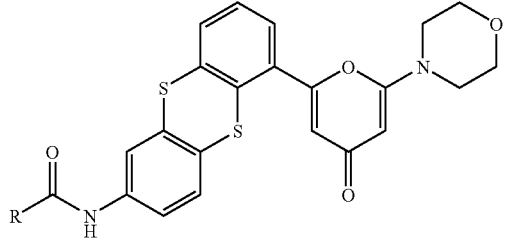

| Compound | R | Purity (%) | Retention Time (Mins) | M+ + 1 |
|---|---|---|---|---|
| 28 | 3-pyridyl | 95 | 3.82 | 516 |
| 29 | 2-furyl | 95 | 4.18 | 505 |
| 30 | 4-pyridyl | 95 | 3.77 | 516 |
| 31 | 2-methoxyphenyl | 95 | 4.73 | 545 |
| 32 | 2-thienyl | 95 | 4.42 | 521 |
| 33 | 2-thienylmethyl | 95 | 4.33 | 535 |
| 34 | cyclobutylmethyl | 95 | 4.31 | 493 |
| 35 | 3,5-dimethylisoxazol-4-yl | 95 | 4.19 | 534 |
| 36 | methoxycarbonyl | 95 | 3.93 | 497 |
| 37 | 3-hydroxy-1-methylpyrazol-5-yl | 95 | 4.18 | 535 |

-continued

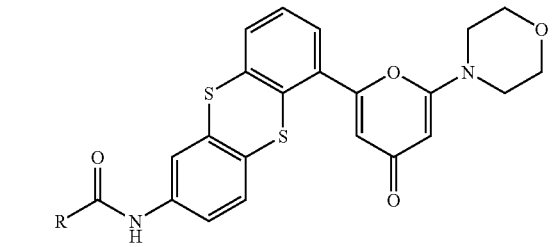

| Compound | R | Purity (%) | Retention Time (Mins) | M+ + 1 |
|---|---|---|---|---|
| 38 | 1-acetylpiperidin-4-yl | 90 | 3.68 | 564 |
| 39 | 2-acetoxyphenyl | 95 | 4.28 | 573 |
| 40 | 2,3,4-trimethoxyphenyl | 95 | 4.43 | 605 |
| 41 | methoxycarbonylethyl | 95 | 3.96 | 525 |
| 42 | acetoxymethyl | 95 | 3.88 | 511 |
| 43 | α-acetoxybenzyl | 95 | 4.42 | 587 |
| 44 | 2,5-dimethylfuran-3-yl | 95 | 4.67 | 533 |
| 45 | benzothiadiazol-5-yl | 910 | 4.62 | 573 |
| 46 | 2-(thien-2-yl)thiazol-4-yl | 95 | 5.16 | 604 |

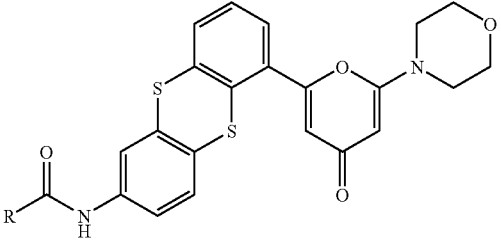

| Compound | R | Purity (%) | Retention Time (Mins) | M⁺ + 1 |
|---|---|---|---|---|
| 47 | 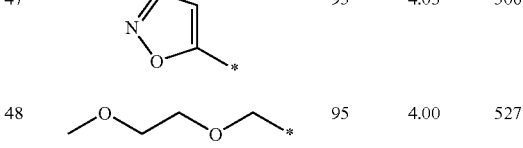 | 95 | 4.03 | 506 |
| 48 | 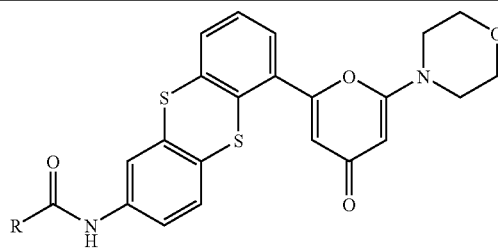 | 95 | 4.00 | 527 |

2-(7-Amino-thianthren-1-yl)-6-morpholin-4-yl-pyran-4-one Biotin Derivatives

To a small test tube was added 2-(7-amino-thianthren-1-yl)-6-morpholin-4-yl-pyran-4-one (21)(49 mg, 0.12 mmol), HBTU (51 mg, 0.13 mmol), di-isopropylethylamine (26µ, 0.15 mmol), the appropriate biotin derivative (0.122 mmol) and dry dimethylacetamide (0.5 ml) with stirring overnight. The reaction was purified by preparative HPLC to give the desired product, which is shown below:

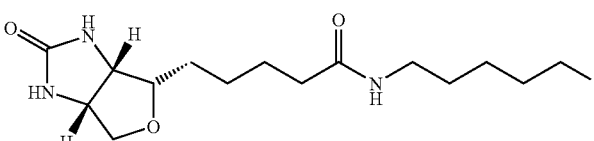

| Compound | R | Purity (%) | Retention Time (Mins) | M⁺ + 1 |
|---|---|---|---|---|
| 49 | | 85 | 3.73 | 637 |
| 50 | | 90 | 3.68 | 750 |

2-Amino-N-[6-(6-morpholin-4-yl-4-oxo-4H-pyran-2-yl)-thianthren-2-yl]-acetamide derivatives To a small test tube was added 2-(7-amino-thianthren-1-yl)-6-morpholin-4-yl-pyran-4-one (21)(20 mg, 0.05 mmol), dry dimethylacetamide (0.5 ml), triethylamine (8 μl, 0.06 mmol) and chloroacetyl chloride (4 μl, 0.06 mmol) with stirring overnight. The appropriate amine or thiol (20 mg or 20 μl) was then added and left to stir at room temperature overnight. The reaction was purified by preparative HPLC to give the desired products, which are shown below:

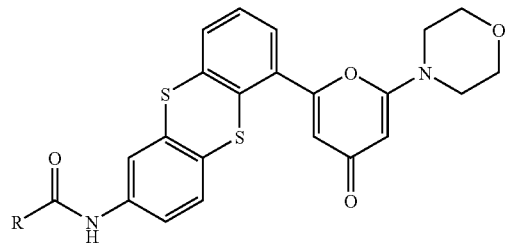

| Compound | R | Purity (%) | Retention Time (Mins) | M⁺ + 1 |
|---|---|---|---|---|
| 51 | morpholinomethyl | 95 | 3.23 | 538 |
| 52 | piperidinomethyl | 95 | 3.30 | 536 |
| 53 | piperazinylmethyl | 95 | 3.18 | 537 |
| 54 | 4-methylpiperazinylmethyl | 95 | 3.24 | 551 |
| 55 | bis(2-hydroxyethyl)aminomethyl | 95 | 3.15 | 556 |
| 56 | bis(2-methoxyethyl)aminomethyl | 95 | 3.46 | 584 |
| 57 | (2-hydroxyethyl)aminomethyl | 95 | 3.11 | 512 |
| 58 | (2-aminoethyl)aminomethyl | 95 | 2.91 | 511 |
| 59 | pyrrolidinylmethyl | 95 | 3.23 | 522 |

-continued
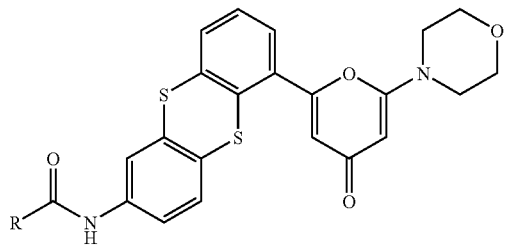
| Compound | R | Purity (%) | Retention Time (Mins) | M+ + 1 |
|---|---|---|---|---|
| 60 | | 90 | 3.17 | 565 |
| 61 | | 95 | 3.11 | 551 |
| 62 | | 85 | 3.43 | 550 |
| 63 | | 95 | 2.94 | 595 |
| 64 | | 90 | 3.49 | 588 |
| 65 | | 90 | 3.64 | 552 |
| 66 | | 95 | 3.30 | 524 |
| 67 | | 95 | 3.08 | 581 |
| 68 | | 95 | 3.32 | 552 |
| 69 | | 95 | 3.19 | 496 |
| 70 | | 95 | 3.40 | 566 |

-continued
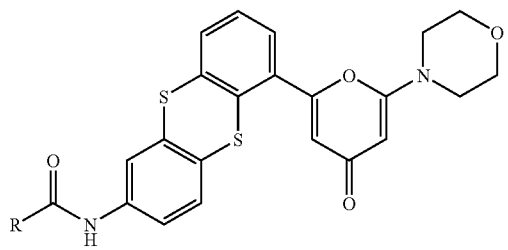
| Compound | R | Purity (%) | Retention Time (Mins) | M⁺ + 1 |
|---|---|---|---|---|
| 71 | pyridin-4-ylmethyl-NH-CH₂-* | 95 | 3.12 | 559 |
| 72 | pyridin-4-ylmethyl-N(Et)-CH₂-* | 95 | 3.40 | 587 |
| 73 | (CH₃)₂N-CH₂CH₂-N(CH₃)-* | 90 | 3.23 | 553 |
| 74 | 2-oxoimidazolidin-1-yl-CH₂CH₂-N(CH₃)-* | 85 | 3.13 | 580 |
| 75 | (1-methylpyrrolidin-2-yl)-CH₂-N(CH₃)-* | 85 | 2.93 | 579 |
| 76 | CH₃O-CH₂CH₂-N(CH₃)-* | 95 | 3.25 | 526 |
| 77 | 4-acetylpiperazin-1-yl-CH₂-* | 95 | 3.24 | 579 |
| 78 | 4-(2-methoxyethyl)piperazin-1-yl-CH₂-* | 95 | 3.28 | 595 |
| 79 | 4-(2-(2-hydroxyethoxy)ethyl)piperazin-1-yl-CH₂-* | 95 | 3.21 | 625 |
| 80 | 4-isopropylpiperazin-1-yl-CH₂-* | 95 | 3.28 | 579 |

-continued
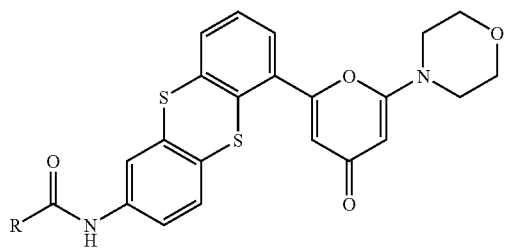
| Compound | R | Purity (%) | Retention Time (Mins) | M⁺ + 1 |
|---|---|---|---|---|
| 81 | ethyl-piperazine-CH₂-* | 95 | 3.25 | 565 |
| 82 | 2-pyridyl-piperazine-CH₂-* | 95 | 3.35 | 614 |
| 83 | 4-fluorophenyl-piperazine-CH₂-* | 95 | 3.72 | 631 |
| 84 | 2-pyrimidinyl-piperazine-CH₂-* | 95 | 3.46 | 615 |
| 85 | isopropyl-NHC(O)CH₂-piperazine-CH₂-* | 95 | 3.33 | 636 |
| 86 | (dimethylamino)ethyl-piperazine-CH₂-* | 95 | 2.96 | 608 |
| 87 | 1-ethyl-pyrrolidin-2-yl-CH₂-NH-CH₂-* | 95 | 3.13 | 579 |
| 88 | piperidinyl-ethyl-NH-CH₂-* | 90 | 3.04 | 579 |

-continued

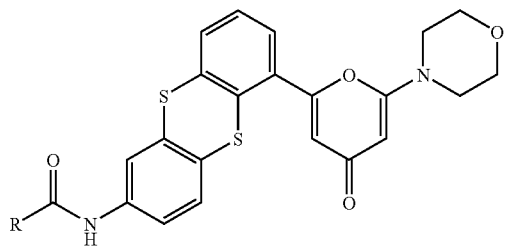

| Compound | R | Purity (%) | Retention Time (Mins) | M+ + 1 |
|---|---|---|---|---|
| 89 | HO~N(piperazine)~NH~* | 95 | 3.18 | 581 |
| 90 | HO~N(homopiperazine)~NH~* | 90 | 3.12 | 595 |

3-Amino-N-[6-(6-morpholin-4-yl-4-oxo-4H-pyran-2-yl)-thianthren-2-yl]-propionamide derivatives To a small test tube was added 2-(7-amino-thianthren-1-yl)-6-morpholin-4-yl-pyran-4-one (21) (20 mg, 0.05 mmol), dry dimethylacetamide (0.5 ml), triethylamine (8 μl, 0.06 mmol) and 3-bromopropionyl chloride (5 μl, 0.05 mmol) with stirring overnight. The appropriate amine or thiol (20 mg or 20 μl, hydrochloride salts were freed by addition of triethylamine) was then added and left to stir at room temperature overnight. The reaction was purified by preparative HPLC to give the desired products, which are shown below:

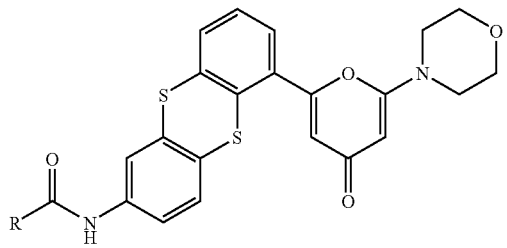

| Compound | R | Purity (%) | Retention Time (Mins) | M+ + 1 |
|---|---|---|---|---|
| 91 | morpholine-ethyl-* | 95 | 3.21 | 552 |
| 92 | piperidine-ethyl-* | 95 | 3.37 | 550 |
| 93 | HN-piperazine-ethyl-* | 90 | 3.11 | 551 |

-continued
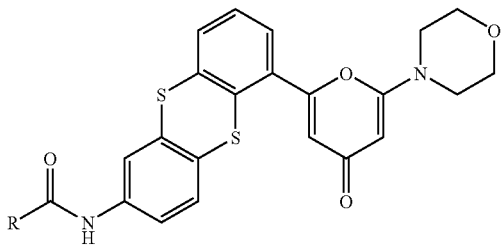
| Compound | R | Purity (%) | Retention Time (Mins) | M+ + 1 |
|---|---|---|---|---|
| 94 | (4-methylpiperazin-1-yl)ethyl | 95 | 3.16 | 565 |
| 95 | N-(2-methoxyethyl)-N-methylaminoethyl | 95 | 3.17 | 570 |
| 96 | 2-hydroxyethylaminoethyl | 95 | 3.18 | 526 |
| 97 | 2-aminoethylaminoethyl | 95 | 2.93 | 525 |
| 98 | pyrrolidin-1-ylethyl | 95 | 3.28 | 536 |
| 99 | (4-methyl-1,4-diazepan-1-yl)ethyl | 95 | 2.98 | 579 |
| 100 | (1,4-diazepan-1-yl)ethyl | 90 | 2.99 | 565 |
| 101 | azepan-1-ylethyl | 95 | 3.43 | 564 |
| 102 | (3-morpholinopropylamino)ethyl | 95 | 3.01 | 609 |
| 103 | (4-methoxybenzylamino)ethyl | 95 | 3.54 | 602 |
| 104 | (1H-1,2,4-triazol-3-ylthio)ethyl | 95 | 3.68 | 566 |

-continued
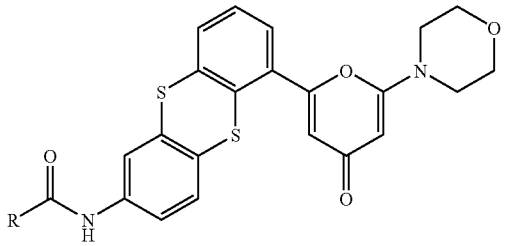
| Compound | R | Purity (%) | Retention Time (Mins) | M+ + 1 |
|---|---|---|---|---|
| 105 | | 95 | 3.33 | 538 |
| 106 | | 95 | 3.10 | 595 |
| 107 | | 95 | 3.37 | 566 |
| 108 | | 90 | 3.20 | 510 |
| 109 | | 95 | 3.38 | 580 |
| 110 | | 95 | 3.13 | 573 |
| 111 | | 95 | 3.23 | 601 |
| 112 | | 95 | 2.99 | 567 |
| 113 | | 95 | 3.20 | 594 |
| 114 | | 95 | 2.98 | 593 |
| 115 | | 90 | 3.25 | 540 |

-continued
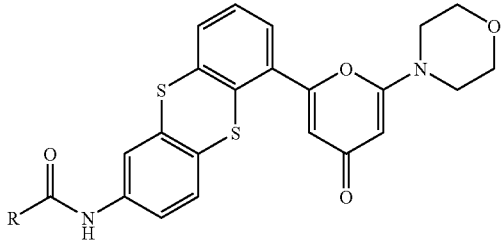
| Compound | R | Purity (%) | Retention Time (Mins) | M⁺ + 1 |
|---|---|---|---|---|
| 116 | acetyl-piperazinyl-ethyl-* | 95 | 3.20 | 593 |
| 117 | HO-ethoxy-ethyl-piperazinyl-ethyl-* | 95 | 3.18 | 639 |
| 118 | isopropyl-piperazinyl-ethyl-* | 85 | 3.20 | 593 |
| 119 | ethyl-piperazinyl-ethyl-* | 85 | 3.18 | 579 |
| 120 | 2-pyridyl-piperazinyl-ethyl-* | 95 | 3.28 | 628 |
| 121 | 4-fluorophenyl-piperazinyl-ethyl-* | 95 | 3.69 | 645 |
| 122 | 2-pyrimidinyl-piperazinyl-ethyl-* | 95 | 3.43 | 629 |
| 123 | isopropyl-NH-C(O)-CH₂-piperazinyl-ethyl-* | 95 | 3.33 | 650 |

-continued
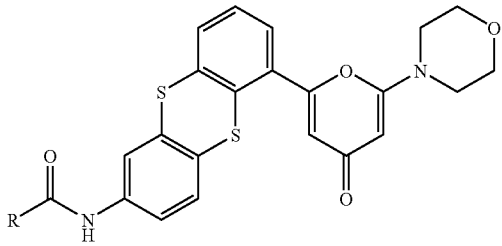
| Compound | R | Purity (%) | Retention Time (Mins) | M+ + 1 |
|---|---|---|---|---|
| 124 | (dimethylamino-ethyl-piperazinyl-ethyl) | 95 | 2.98 | 622 |
| 125 | (carbamoylmethyl-amino-ethyl) | 95 | 3.14 | 539 |
| 126 | (1-ethyl-pyrrolidin-2-ylmethyl-amino-ethyl) | 95 | 2.98 | 593 |
| 127 | (piperidinyl-ethyl-amino-ethyl) | 90 | 2.95 | 593 |
| 128 | (hydroxyethyl-piperazinyl-ethyl) | 95 | 3.13 | 595 |
| 129 | (hydroxyethyl-diazepanyl-ethyl) | 90 | 2.97 | 609 |
Example 3
2-(4-Hydroxy-thianthren-1-yl)-6-morpholin-4-yl-pyran-4-one derivatives
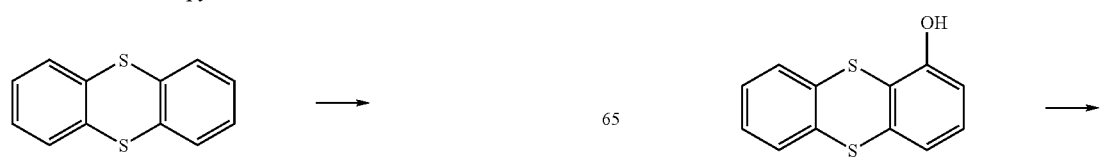

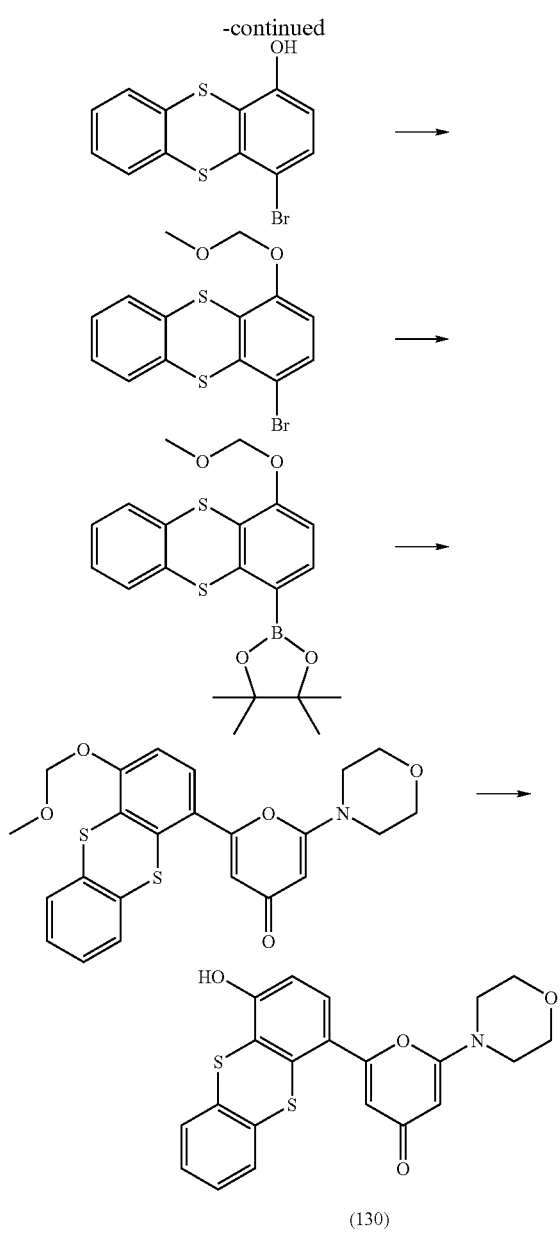

(130)

Thianthren-1-ol

To a cooled (−78° C.) solution of thianthrene (10 g, 46.23 mmol) in anhydrous THF (200 ml) was added t-BuLi (1.7M in pentane, 40.81 ml, 69.34 mmol), under a nitrogen atmosphere, over a period of 10 minutes and the resulting yellow solution was then allowed to warm to room temperature and stirred vigorously for a further 16 hours. EtMgBr (3M in THF, 23 ml, 69.34 mmol) was then added in a dropwise fashion to the cooled (0° C.) reaction mixture which was then stirred for a further 45 minutes before oxygen was bubbled through the solution. After two hours the reaction was quenched by dropwise addition of 1M NaOH (100 ml) and washed with EtOAc (1×300 ml) before being acidified to pH4 with aqueous 1M HCl. The mixture was then extracted with EtOAc (3×100 mL), dried (MgSO$_4$), filtered and concentrated in vacuo to give a mild amber slurry that was purified by flash chromatography (SiO$_2$) (10:1, Ethyl acetate/Hexanes), to give the title compound (3.82 g, 36%) as a yellow solid. m/z (LC-MS, ESP):, RT=4.62 min, (M$^+$+1)=231

4-Bromo-thianthren-1-ol

Thianthren-1-ol (6.5 g, 27.98 mmol) was dissolved in glacial acetic acid (100 ml) and to this solution was added bromine (17.1 μl, 13.99 mmol) in a dropwise fashion over 30 minutes. Water (200 ml) was added to the amber solution and the mixture extracted with EtOAc (3×100 ml). The combined organic extracts were then washed with saturated potassium bicarbonate solution (3×100 ml), dried using MgSO$_4$, filtered and concentrated in vacuo to give the title compound. (7.56 g, 87%). m/z (LC-MS, ESP):, RT=4.92 min, (M$^+$+1)=309.

1-Bromo-4-methoxymethoxy-thianthrene

To a cooled (0° C.) solution of 4-Bromo-thianthren-1-ol (1.0 g, 3.21 mmol) in DMF (12 ml) was added NaH (60% dispersed in mineral oil, 0.23 g, 9.63 mmol) portionwise over 30 minutes and stirred for a further 30 minutes at this temperature. Chloromethylmethylether (0.26 g, 3.241 mmol) was then added and the reaction allowed to stir at room temperature for 2 hours. Water was added to the mixture which was then extracted using EtOAc (3×50 ml). The combined organic extracts were then dried (MgSO$_4$), filtered and concentrated in vacuo to give a mild amber liquid. The crude residue was purified by flash chromatography (SiO$_2$) (10:1, Hexanes/EtOAc) to give the title compound as a mild amber oil that crystallised upon standing (1.11 g, 97%). m/z (LC-MS, ESP):, RT=5.55 min, (M$^+$+1)=355.

2-(4-Methoxymethoxy-thianthren-1-yl)-4,4,5,5-tetramethyl-[1,3,2]dioxaborolane

1-Bromo-4-methoxymethoxy-thianthrene (2.06 g, 5.80 mmol) was dissolved in anhydrous dioxane (10 ml) and to this solution was added bis(pinacolato)diboron (1.75 g, 6.96 mmol), 1,1-bis(diphenylphosphino)ferrocene (0.18 g, 0.05 mmol) and potassium acetate (1.7 g, 17.40 mmol) under a nitrogen atmosphere. The mixture was degassed for 10 minutes and (1,1'-bis(diphenylphosphino)ferrocene-dichloropalladium(II) dichloromethane adduct (0.24 g, 5% eq) was added. The reaction was heated at 90° C. under a nitrogen atmosphere for 24 hours. The dark brown reaction mixture was then allowed to cool to room temperature before it was applied to a thick silica pad prepared in hexanes and eluted with hexanes:CH$_2$Cl$_2$-(2:1). The eluent was concentrated in vacuo to give a dark brown oil (2.33 g, 100%) that was used for the next transformation with no further purification. RT=5.63 min.

2-(4-Methoxymethoxy-thianthren-1-yl)-6-morpholin-4-yl-pyran-4-one 2-(4-Methoxymethoxy-thianthren-1-yl)-4,4,5,5-tetramethyl-[1,3,2]dioxaborolane (6.23 g, 17.14 mmol), 2-chloro-6-morpholin-4-yl-pyran-4-one (3) (6.99 g, 17.40 mmol) and powdered potassium carbonate (7.20 g, 52.20 mmol) were suspended in anhydrous dioxane (60 ml) under a nitrogen atmosphere. The mixture was degassed for 15 minutes before the addition of tetrakis(triphenylphosphino)palladium (1.2 g, 5% eq) and then degassed for a further 15 minutes after addition. The reaction was then heated at 90° C. for 24 hours. Water (60 ml) was added and the mixture extracted with EtOAc (3×30 ml). The organic extracts were then dried using MgSO$_4$, filtered and concentrated in vacuo to yield a dark yellow oil. The crude residue was then purified by flash chromatography (SiO$_2$) (9:1—EtOAc/MeOH) to give the title compound (7.93 g, 79%) as a green powder. m/z (LC-MS, ESP): RT=4.39 min, (M$^+$+1)=456

2-(4-Hydroxy-thianthren-1-yl) -6-morpholin-4-yl-pyran-4-one (130)

To a solution of 2-(4-Methoxymethoxy-thianthren-1-yl)-6-morpholin-4-yl-pyran-4-one (1.1 g, 2.42 mmol) in acetone (50 ml) was added sodium iodide (0.40 g, 2.66 mmol) and concentrated HCl (3 ml). The dark suspension was stirred at room temperature for 72 hours before the careful addition of 1M sodium hydroxide solution until pH 12 was attained. The mixture was washed with EtOAc (2×50 ml) and then acidified with concentrated HCl until pH 1 whereupon a brown precipitate formed which was filtered off (0.90 g, 90%) and corresponded to the title compound. m/z (LC-MS, ESP): RT=4.39 min, (M$^+$+1)=456

2-(4-Hydroxy-thianthren-1-yl) -6-morpholin-4-yl-pyran-4-one derivatives

To a solution of 2-(4-Hydroxy-thianthren-1-yl)-6-morpholin-4-yl-pyran-4-one (130) (25 mg, 0.06 mmol) in anhydrous Dimethylformamide (0.66 ml) was added powdered potassium carbonate (33 mg, 0.24 mmol) and 1,2-dibromoethane (26 µl, 0.3 mmol). After stirring the reaction mixture for 24 hours the appropriate amine or thiol was added to the solution and stirred at room temperature for a further 24 hours. The crude mixture was then purified by preparative HPLC to give the desired compounds, which are shown below:

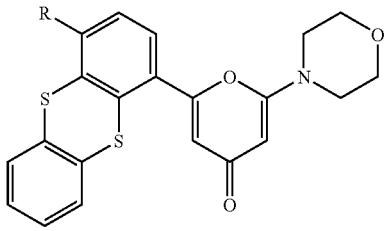

| Compound | R | Purity (%) | Retention Time (Mins) | M$^+$ + 1 |
|---|---|---|---|---|
| 131 | 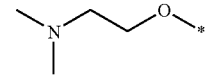 | 95 | 3.13 | 470 |
| 132 | 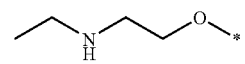 | 95 | 3.20 | 484 |
| 133 | 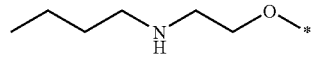 | 95 | 3.21 | 484 |
| 134 | 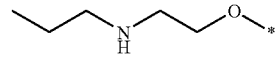 | 95 | 3.43 | 512 |
| 135 | 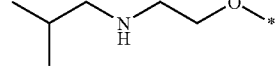 | 95 | 3.33 | 498 |
| 136 | 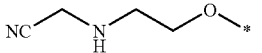 | 90 | 3.41 | 512 |
| 137 | 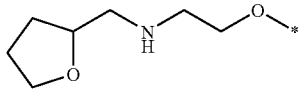 | 95 | 3.24 | 494 |
| 138 | 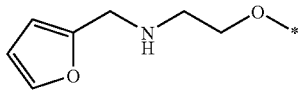 | 95 | 3.31 | 540 |
| 139 | 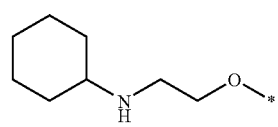 | 95 | 3.38 | 536 |
| 140 |  | 95 | 3.45 | 538 |

-continued
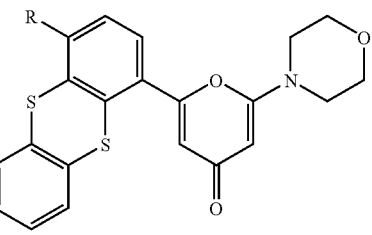
| Compound | R | Purity (%) | Retention Time (Mins) | M+ + 1 |
|---|---|---|---|---|
| 141 | 2,6-dimethylmorpholin-N-ylethoxy | 95 | 3.35 | 554 |
| 142 | cyclobutylaminoethoxy | 85 | 3.33 | 510 |
| 143 | cyclohexylmethylaminoethoxy | 95 | 3.61 | 552 |
| 144 | cyclopentylaminoethoxy | 95 | 3.38 | 524 |
| 145 | pyrrolidin-1-ylethoxy | 95 | 3.23 | 510 |
| 146 | piperidin-1-ylethoxy | 95 | 3.28 | 524 |
| 147 | morpholin-4-ylethoxy | 95 | 3.23 | 526 |
| 148 | azepan-1-ylethoxy | 90 | 3.41 | 538 |
| 149 | benzoylhydrazinoethoxy | 60 | 3.52 | 553 |
| 150 | azepan-1-ylaminoethoxy | 90 | 3.52 | 567 |

-continued

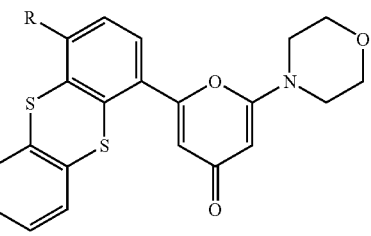

| Compound | R | Purity (%) | Retention Time (Mins) | M⁺ + 1 |
|---|---|---|---|---|
| 151 | 2,6-dimethylpiperidinyl-NH-CH₂CH₂-O-* | 95 | 3.66 | 567 |
| 152 | 4-methylpiperazinyl-N-NH-CH₂CH₂-O-* | 85 | 3.02 | 554 |
| 153 | morpholinyl-N-NH-CH₂CH₂-O-* | 85 | 3.31 | 541 |
| 154 | piperidinyl-CH₂CH₂-NH-CH₂CH₂-O-* | 90 | 2.99 | 567 |
| 155 | pyrrolidinyl-CH₂CH₂-NH-CH₂CH₂-O-* | 95 | 3.00 | 553 |
| 156 | (1-methylpyrrolidin-2-yl)-CH₂CH₂-NH-CH₂CH₂-O-* | 95 | 2.97 | 567 |
| 157 | 4-(dimethylamino)benzyl-NH-CH₂CH₂-O-* | 95 | 3.66 | 589 |
| 158 | (pyridin-2-yl)methyl-NH-CH₂CH₂-O-* | 95 | 3.40 | 547 |
| 159 | (pyridin-3-yl)methyl-NH-CH₂CH₂-O-* | 90 | 3.16 | 547 |
| 160 | 2-(pyridin-2-yl)ethyl-NH-CH₂CH₂-O-* | 95 | 3.43 | 561 |

-continued
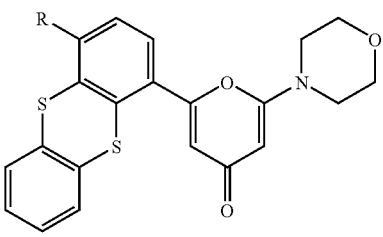
| Compound | R | Purity (%) | Retention Time (Mins) | M+ + 1 |
|---|---|---|---|---|
| 161 | | 95 | 3.47 | 575 |
| 162 | | 95 | 2.95 | 550 |
| 163 | | 95 | 3.17 | 569 |
| 164 | | 95 | 3.12 | 658 |
| 165 | | 90 | 2.97 | 555 |
| 166 | | 85 | 2.97 | 569 |
| 167 | | 95 | 3.06 | 583 |
| 168 | | 85 | 3.15 | 541 |
| 169 | | 95 | 3.07 | 527 |

-continued

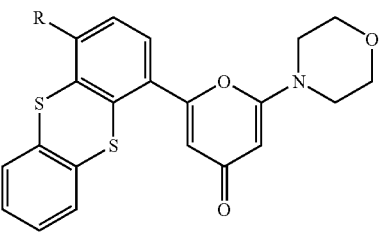

| Compound | R | Purity (%) | Retention Time (Mins) | M⁺ + 1 |
|---|---|---|---|---|
| 170 | (dimethylaminomethyl-furan-CH2-S-CH2CH2-NH-CH2CH2-O-*) | 85 | 3.03 | 653 |

To a solution of 2-(4-Hydroxy-thianthren-1-yl)-6-morpholin-4-yl-pyran-4-one (130) (25 mg, 0.06 mmol) in anhydrous dimethylformamide (0.66 ml) was added powdered potassium carbonate (33 mg, 0.24 mmol) and 1,3-dibromopropane (23 μl, 0.3 mmol). After stirring the reaction mixture for 24 hours the appropriate amine or thiol was added to the solution and stirred at room temperature for a further 24 hours. The crude mixture was then purified by preparative HPLC to give the desired compounds, which are shown below:

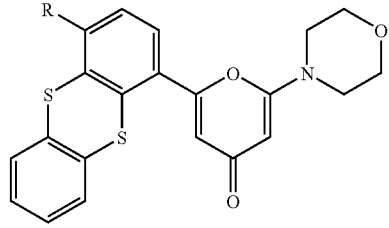

| Compound | R | Purity (%) | Retention Time (Mins) | M⁺ + 1 |
|---|---|---|---|---|
| 171 | Et2N-CH2CH2CH2-O-* | 95 | 3.33 | 526 |
| 172 | EtNH-CH2CH2CH2-O-* | 95 | 3.24 | 498 |
| 173 | iPr2N-CH2CH2CH2-O-* | 95 | 3.48 | 554 |
| 174 | nBuNH-CH2CH2CH2-O-* | 85 | 3.48 | 526 |
| 175 | iBuNH-CH2CH2CH2-O-* | 95 | 3.46 | 526 |
| 176 | iPrNH-CH2CH2CH2-O-* | 95 | 3.33 | 512 |

-continued
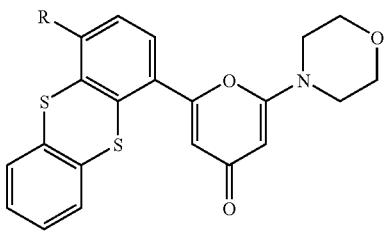
| Compound | R | Purity (%) | Retention Time (Mins) | M⁺ + 1 |
|---|---|---|---|---|
| 177 | F₃C―\―NH―\―O―* | 95 | 3.64 | 552 |
| 178 | (tetrahydrofuran-2-yl)CH₂―NH―\―O―* | 95 | 3.36 | 554 |
| 179 | (furan-2-yl)CH₂―NH―\―O―* | 85 | 3.39 | 550 |
| 180 | cyclohexyl―NH―\―O―* | 85 | 3.53 | 552 |
| 181 | (2,6-dimethylmorpholino)―\―O―* | 95 | 3.44 | 568 |
| 182 | cyclobutyl―NH―\―O―* | 85 | 3.40 | 524 |
| 183 | cyclohexyl―CH₂―NH―\―O―* | 85 | 3.70 | 566 |
| 184 | cyclopentyl―NH―\―O―* | 95 | 3.47 | 538 |
| 185 | pyrrolidino―\―O―* | 95 | 3.31 | 524 |
| 186 | piperidino―\―O―* | 95 | 3.42 | 538 |
| 187 | morpholino―\―O―* | 95 | 3.24 | 540 |

-continued
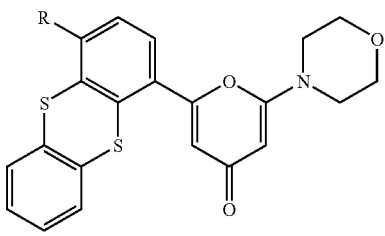
| Compound | R | Purity (%) | Retention Time (Mins) | M⁺ + 1 |
|---|---|---|---|---|
| 188 | azepan-1-yl-propoxy | 95 | 3.49 | 552 |
| 189 | benzoyl-hydrazido-propoxy | 95 | 4.08 | 589 |
| 190 | azepan-1-yl-amino-propoxy | 95 | 3.42 | 567 |
| 191 | 4-methylpiperazin-1-yl-amino-propoxy | 90 | 2.95 | 568 |
| 192 | morpholin-4-yl-amino-propoxy | 95 | 3.24 | 555 |
| 193 | piperidin-1-yl-amino-propoxy | 95 | 2.96 | 581 |
| 194 | (1-methylpyrrolidin-2-yl)ethylamino-propoxy | 85 | 2.94 | 581 |
| 195 | pyridin-2-ylamino-propoxy | 90 | 3.33 | 561 |
| 196 | pyridin-4-ylamino-propoxy | 90 | 3.13 | 561 |
| 197 | (pyridin-2-ylethyl)methylamino-propoxy | 95 | 3.36 | 589 |

-continued
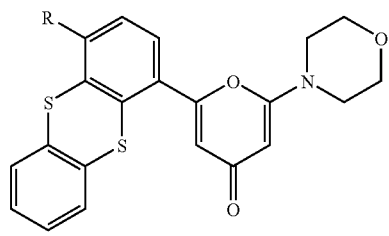
| Compound | R | Purity (%) | Retention Time (Mins) | M+ + 1 |
|---|---|---|---|---|
| 198 | imidazole-CH2CH2-NH-CH2CH2CH2-O-* | 85 | 2.89 | 564 |
| 199 | (Et)2N-CH2CH2-NH-CH2CH2CH2-O-* | 90 | 2.93 | 583 |
| 200 | (iPr)2N-CH2CH2-NH-CH2CH2CH2-O-* | 90 | 2.99 | 597 |
| 201 | (Me)2N-CH2CH2-N(Me)-CH2CH2CH2-O-* | 85 | 2.94 | 555 |
| 202 | (Me)2N-CH2CH2-N(Bn)-CH2CH2CH2-O-* | 90 | 3.10 | 631 |
| 203 | MeNH-CH2CH2-N(Me)-CH2CH2CH2-O-* | 90 | 2.91 | 541 |
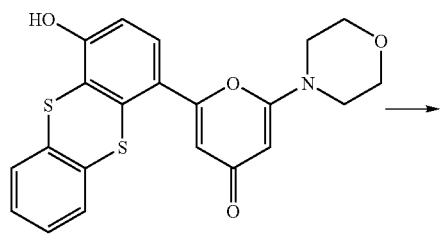

-continued

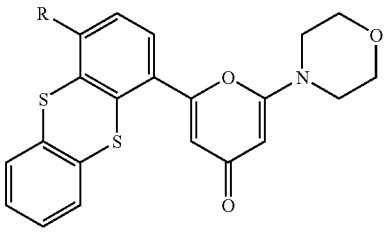

| Compound | R | Purity (%) | Retention Time (Mins) | M⁺ + 1 |

[4-(6-Morpholin-4-yl-4-oxo-4H-pyran-2-yl)-thianthren-1-yloxy]-acetic acid methyl ester To a solution of 2-(4-Hydroxy-thianthren-1-yl)-6-morpholin-4-yl-pyran-4-one (130) (1.20 g, 2.91 mmol) in dimethylformamide (10 ml), under and inert atmosphere, was added powdered potassium carbonate (1.21 g, 8.75 mmol) and methylbromoacetate (0.55 ml, 5.82 mmol). The temperature of the reaction was raised to 60° C. for 48 hours and then cooled to room temperature before the addition of water (20 mL). The mixture was then extracted using ethyl acetate (3×30 ml). The combined organics were dried (MgSO₄), filtered and concentrated in vacuo to give the title compound as an off white solid (1.40 g, 99%) that was suitably clan and required no further purification. m/z (LC-MS, ESP): RT=4.48 min, (M⁺+1)=484

[4-(6-Morpholin-4-yl-4-oxo-4H-pyran-2-yl)-thianthren-1-yloxy]-acetic acid sodium salt To a solution of [4-(6-Morpholin-4-yl-4-oxo-4H-pyran-2-yl)-thianthren-1-yloxy]-acetic acid methyl ester (1.41 g, 2.91 mmol) in anhydrous methanol (10 ml) was added sodium hydroxide (120 mg, 2.91 mmol) in a single portion. The solution was then stirred at room temperature for 24 hours whereupon the solvent was removed in vacuo to give the title compound as an off white paste (1.43 g, 98%) that required no further purification. m/z (LC-MS, ESP): RT=3.79 min, (M⁻−23)=468

[4-(6-Morpholin-4-yl-4-oxo-4H-pyran-2-yl)-thianthren-1-yloxy]-acetic acid derivatives To a solution of [4-(6-Morpholin-4-yl-4-oxo-4H-pyran-2-yl)-thianthren-1-yloxy]-acetic acid sodium salt (20 mg, 0.04 mmol) in dimethylacetamide (1 ml) was added O-(1H-benzotriazol-1-yl)-N,N,N',N'-tetramethyluronium hexafluorophosphate (25 mg, 0.07 mmol) followed by N,N-diisopropylethylamine (16 μl, 0.09 mmol). Finally, the appropriate amine or thiol was added to the solution which was stirred at room temperature for 24 hours. The crude mixture was then purified by preparative HPLC to give the desired compounds, which are shown below:

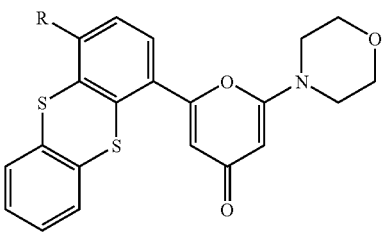
| Compound | R | Purity (%) | Retention Time (Mins) | M⁺ + 1 |
|---|---|---|---|---|
| 204 | diethylaminocarbonylmethoxy | 95 | 4.23 | 526 |
| 205 | diisopropylaminocarbonylmethoxy | 90 | 3.98 | 498 |
| 206 | n-butylaminocarbonylmethoxy | 90 | 4.33 | 554 |
| 207 | n-propylaminocarbonylmethoxy | 90 | 4.15 | 526 |
| 208 | isobutylaminocarbonylmethoxy | 90 | 4.32 | 526 |
| 209 | isopropylaminocarbonylmethoxy | 95 | 4.11 | 512 |
| 210 | cyanomethylaminocarbonylmethoxy | 85 | 3.98 | 552 |
| 211 | 2,2,2-trifluoroethylaminocarbonylmethoxy | 95 | 4.20 | 554 |
| 212 | furfurylaminocarbonylmethoxy | 95 | 4.17 | 550 |

-continued
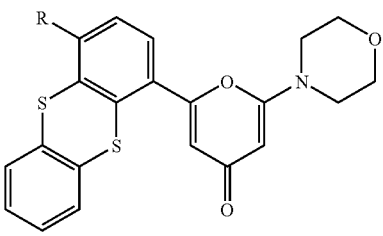
| Compound | R | Purity (%) | Retention Time (Mins) | M⁺ + 1 |
|---|---|---|---|---|
| 213 | (2,6-dimethylmorpholine acetamide-O-*) | 95 | 4.16 | 552 |
| 214 | (cyclohexylmethyl-NH-C(O)-CH₂-O-*) | 95 | 4.77 | 568 |
| 215 | (cyclopentyl-NH-C(O)-CH₂-O-*) | 90 | 4.43 | 524 |
| 216 | (pyrrolidine-C(O)-CH₂-O-*) | 95 | 4.02 | 566 |
| 217 | (piperidine-C(O)-CH₂-O-*) | 95 | 4.29 | 538 |
| 218 | (azepane-C(O)-CH₂-O-*) | 85 | 4.38 | 524 |
| 219 | (2,6-dimethylpiperidinyl-N-NH-C(O)-CH₂-O-*) | 85 | 4.23 | 538 |
| 220 | (morpholino-N-NH-C(O)-CH₂-O-*) | 85 | 3.83 | 540 |

-continued
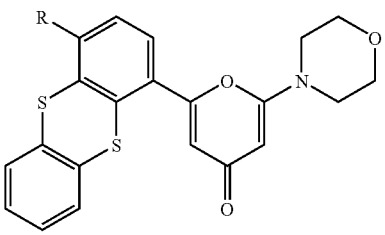
| Compound | R | Purity (%) | Retention Time (Mins) | M+ + 1 |
|---|---|---|---|---|
| 221 | piperidine-N-CH2CH2-NH-C(O)-CH2-O-* | 90 | 3.35 | 552 |
| 222 | pyrrolidine-N-CH2CH2-NH-C(O)-CH2-O-* | 95 | 3.30 | 569 |
| 223 | 1-methylpyrrolidin-2-yl-CH2CH2-NH-C(O)-CH2-O-* | 90 | 3.31 | 585 |
| 224 | pyridin-2-yl-CH2-NH-C(O)-CH2-O-* | 95 | 3.64 | 589 |
| 225 | pyridin-4-yl-CH2-NH-C(O)-CH2-O-* | 95 | 3.33 | 567 |
| 226 | pyridin-2-yl-CH2CH2-NH-C(O)-CH2-O-* | 95 | 3.41 | 568 |
| 227 | pyridin-4-yl-CH2-N(Et)-C(O)-CH2-O-* | 90 | 3.49 | 555 |
| 228 | pyridin-2-yl-CH2CH2-N(Me)-C(O)-CH2-O-* | 90 | 3.46 | 581 |
| 229 | 1H-imidazol-4-yl-CH2CH2-NH-C(O)-CH2-O-* | 95 | 3.27 | 581 |

-continued
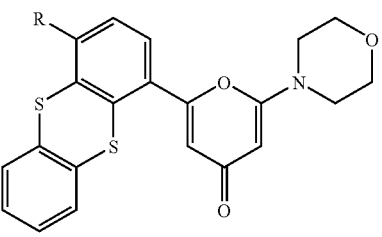
| Compound | R | Purity (%) | Retention Time (Mins) | M+ + 1 |
|---|---|---|---|---|
| 230 | morpholine-CH2CH2-NH-C(O)-CH2-O-* | 95 | 3.28 | 561 |
| 231 | benzyl-piperazine-CH2CH2-NH-C(O)-CH2-O-* | 95 | 3.51 | 561 |
| 232 | Et2N-CH2CH2-NH-C(O)-CH2-O-* | 95 | 3.33 | 589 |
| 233 | iPr2N-CH2CH2-NH-C(O)-CH2-O-* | 95 | 3.43 | 564 |
| 234 | Me2N-CH2CH2-N(Me)-C(O)-CH2-O-* | 95 | 3.34 | 583 |
| 235 | H2N-CH2CH2-NH-C(O)-CH2-O-* | 95 | 3.21 | 597 |
| 236 | benzyl,Me2N-CH2CH2-N-C(O)-CH2-O-* | 990 | 3.63 | 555 |
| 237 | Me2N-CH2CH2-NH-C(O)-CH2-O-* | 95 | 3.25 | 631 |
| 238 | Me2N-CH2-furan-CH2-S-CH2CH2-NH-C(O)-CH2-O-* | 95 | 3.57 | 541 |

Example 4

2-Morpholin-4-yl-6-(10H-phenothiazin-4-yl)-pyran-4-one alkyl derivatives

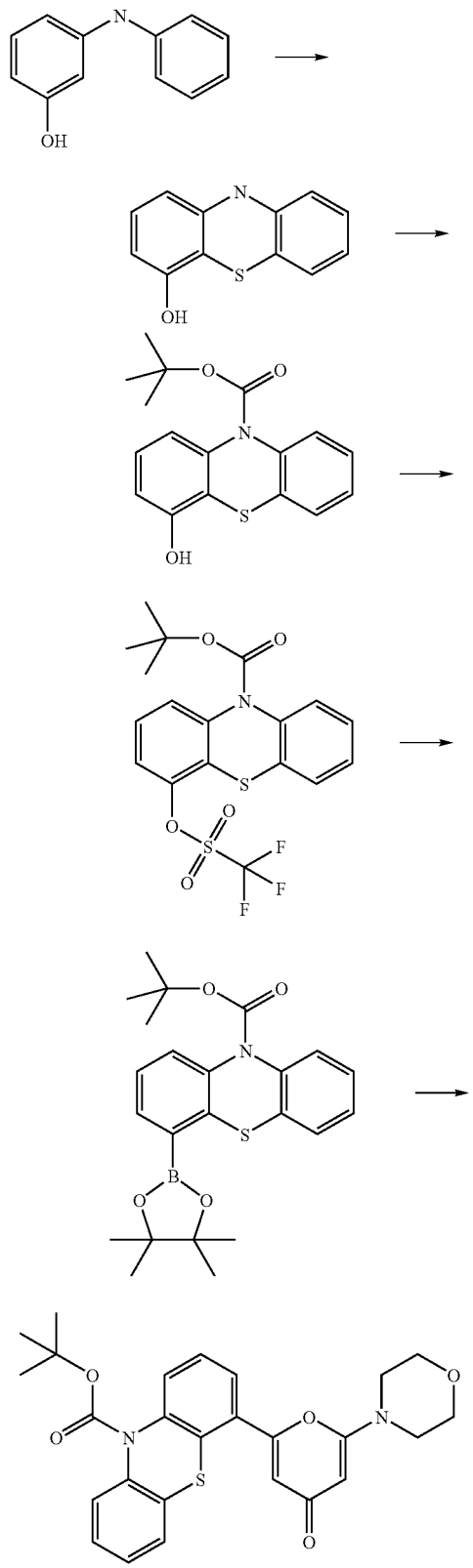

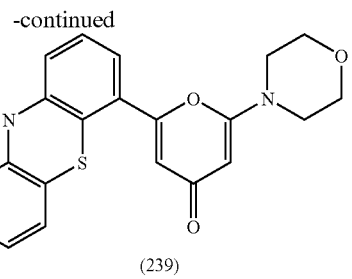

(239)

10H-Phenothiazin-4-ol

To a solution of 3-phenylamino-phenol (5 g, 26.99 mmol) in 1,2-dichlorobenzene (50 ml) was added $S_8$ sulfur (1.82 g, 56.76 mmol) in a single portion and iodine (0.1 g, 0.39 mmol) which was added in three portions over 10 minutes. A reflux condenser was attached to the reaction vessel which was heated to 185° C. under a nitrogen atmosphere. The mixture was stirred at this temperature for 4 hours and then allowed to cool to room temperature. The reaction mixture was filtered to remove a black precipitate and the filtrate diluted with $Et_2O$ (100 ml) and washed with water (2×100 ml). The organic layer was separated and the volatile solvents removed to give a deep green oil that was purified by flash column chromatography ($SiO_2$) (Hexanes then 8:1-Hexanes:EtOAc) to give a pale yellow solid (2.38 g, 40.96%) m/z (LC-MS, ESP) 216 $[M+H]^+$, RT=4.12 mins.

4-Hydroxy-phenothiazine-10-carboxylic acid tert-butyl ester

To a solution of 10H-phenothiazin-4-ol (0.77 g, 3.58 mmol) in anhydrous pyridine (10 ml) was added di-tertiary butyl dicarbonate (3.12 g, 14.31 mmol) in a single portion. The solution was heated to 80° C. and stirred under a nitrogen atmosphere for 60 minutes before being allowed to cool to room temperature and treated with water (20 ml) and extracted with EtOAc (2×30 ml). The organic layers were then washed with water (20 ml), dried using $MgSO_4$, filtered and concentrated in vacuo to give an amber oil. The crude residue was treated with MeOH (15 ml) and solid NaOH (0.65 g, 16.25 mmol). The mixture was heated to 80° C. for 60 minutes then cooled to room temperature and neutralised to pH7 with 1M HCl solution. The resulting suspension was then filtered and dried to give the title compound as a beige solid (1.13 g, 100%) that was used without further purification. m/z (LC-MS, ESP): 315 $[M-H]^-$, RT=4.72 mins.

4-Trifluoromethanesulfonyloxy-phenothiazine-10-carboxylic acid tert-butyl ester Trifluoromethanesulfonic anhydride (2.95 ml, 17.09 mmol) was added in a dropwise fashion over 10 minutes to a cooled (0° C.) stirred solution of 4-hydroxy-phenothiazine-10-carboxylic acid tert-butyl ester (3.60 g, 11.41 mmol) in pyridine (40 ml). The reaction mixture was stirred at 0° C. for 1 hour before the addition of water (80 ml). The mixture was extracted using EtOAc (2×60 ml). The organic extracts were then dried using $MgSO_4$, filtered and concentrated in vacuo to give a dark brown oil. The crude residue was then purified by flash chromatography (SiO$_2$) (4:1-Hexanes:EtOAc) to yield a yellow oil (5.02 g, 98.24%) m/z (LC-MS, ESP): 348 [M+H-BOC]$^+$, RT=5.61 mins.

4-(4,4,5,5-Tetramethyl-[1,3,2]dioxaborolan-2-yl)-phenothiazine-10-carboxylic acid tert-butyl ester To a stirred solution of 4-trifluoromethanesulfonyloxy-phenothiazine-10-carboxylic acid tert-butyl ester (3.0 g, 6.7 mmol) in anhydrous dioxane (10 ml) was added bis(pinacolato)diboron (2.05 g, 8.06 mmol) and potassium acetate (1.96 g, 20.01 mmol). The reaction was then degassed (sonication for 20 minutes then saturated with N$_2$) before the addition of dichloro[1,1'-bis(diphenylphosphino)ferrocene]palladium (II) dichloromethane adduct (0.27 g, 0.33 mmol). The reaction mixture was degassed for a further 20 minutes before a reflux condenser was attached to the reaction vessel which was then heated to 90° C. and stirred vigorously for 72 hours. The dark brown reaction mixture was then allowed to cool to room temperature before it was applied to a thick silica pad prepared in hexanes and eluted with hexanes:CH$_2$Cl$_2$-(2:1). The eluent was concentrated in vacuo to give a dark brown oil (2.85 g, 100%) that was used for the next transformation with no further purification. m/z (LC-MS, ESP): 326 [M+H-BOC]$^+$, RT=5.86 mins.

4-(6-Morpholin-4-yl-4-oxo-4H-pyran-2-yl)-phenothiazine-10-carboxylic acid tert-butyl ester Powdered potassium carbonate (2.03 g, 14.68 mmol) and 2-chloro-6-morpholin-4-yl-pyran-4-one (3) (1.44 g, 6.70 mmol) were added to a stirred solution of 4-(4,4,5,5-tetramethyl-[1,3,2]dioxaborolan-2-yl)-phenothiazine-10-carboxylic acid tert-butyl ester (2.85 g, 6.70 mmol) in anhydrous dioxane (20 ml) and the mixture degassed (sonication for 20 minutes then saturated with N$_2$) thoroughly. Tetrakis (triphenylphosphine) palladium was then added in a single portion and the mixture degassed (sonication for 20 minutes then saturated with N$_2$) once again before a reflux condenser was attached and the mixture heated to 100° C. under a nitrogen atmosphere for 20 hours. Water (30 ml) was added and the mixture extracted with EtOAc (3×30 ml). The organic extracts were then dried using MgSO$_4$, filtered and concentrated in vacuo to yield a dark brown, crystalline solid (3.21 g, 100%) that was taken forward with no further purification. m/z (LC-MS, ESP): 479 [M+H]$^+$, RT=4.55 mins.

2-Morpholin-4-yl-6-(10H-phenothiazin-4-yl)-pyran-4-one (239)

To a stirred solution of 4-(6-morpholin-4-yl-4-oxo-4H-pyran-2-yl)-phenothiazine-10-carboxylic acid tert-butyl ester (3.65 g, 7.63 mmol), in CH$_2$Cl$_2$ (30 ml) was added trifluoroacetic acid in a single portion. The mixture was stirred at room temperature for 20 hours whereupon the reaction was concentrated in vacuo to give a thick syrup that was basified in a dropwise fashion with saturated NaHCO$_3$ (40 ml). The dark green mixture was then stirred at room temperature for 18 hours. The mixture was filtered and the filtrant retained, washed with water and dried to give the title compound as a dark green solid (2.89 g, 83.74% over 3 steps) m/z (LC-MS, ESP): 479 [M+H]$^+$, RT=4.05 mins.

2-Morpholin-4-yl-6-(10H-phenothiazin-4-yl)-pyran-4-one alkyl derivatives

To a cooled (0° C.) solution of 2-morpholin-4-yl-6-(10H-phenothiazin-4-yl)-pyran-4-one (239) (20 mg, 0.05 mmol) in dimethylformamide (0.5 ml), was added sodium hydride (60% in min oil, 6 mg, 0.15 mmol). The resulting brown solution was stirred for 1 hour whereupon 1-bromo-3-chloropropane (6.6 µl, 0.06 mmol) was added in a single portion and stirred at room temperature for 1 hour. The appropriate amine was then added and the reaction mixture heated to 60° C. for 48 hours and then purified by preparative HPLC to give the desired products, which are shown below:

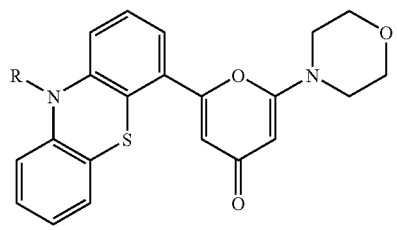

| Compound | R | Purity (%) | Retention Time (Mins) | M$^+$ + 1 |
|---|---|---|---|---|
| 240 | (tetrahydrofuran-2-ylmethyl)(propyl)amine | 85 | 3.29 | 521 |
| 241 | ethyl(propyl)amine | 95 | 3.18 | 465 |
| 242 | isobutyl(propyl)amine | 90 | 3.32 | 493 |
| 243 | propyl(propyl)amine | 85 | 3.27 | 479 |

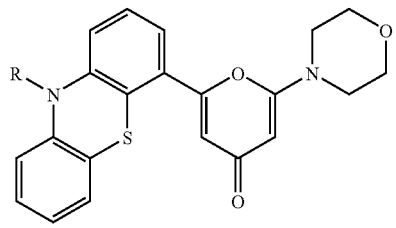
| Compound | R | Purity (%) | Retention Time (Mins) | M+ + 1 |
|---|---|---|---|---|
| 244 | Et₂N-CH₂CH₂CH₂-* | 95 | 3.26 | 493 |
| 245 | nBu-NH-CH₂CH₂CH₂-* | 85 | 3.38 | 493 |
| 246 | iPr-NH-CH₂CH₂CH₂-* | 95 | 3.23 | 479 |
| 247 | F₃C-CH₂-NH-CH₂CH₂CH₂-* | 85 | 3.53 | 519 |
| 248 | MeNH-CH₂CH₂CH₂-* | 85 | 3.14 | 451 |
| 249 | Me₂N-CH₂CH₂CH₂-* | 95 | 3.18 | 465 |
| 250 | (2-furyl)CH₂-NH-CH₂CH₂CH₂-* | 90 | 3.31 | 517 |
| 251 | cyclohexyl-NH-CH₂CH₂CH₂-* | 95 | 3.45 | 519 |
| 252 | cyclobutyl-NH-CH₂CH₂CH₂-* | 90 | 3.29 | 491 |
| 253 | cyclohexyl-CH₂-NH-CH₂CH₂CH₂-* | 95 | 3.56 | 533 |
| 254 | cyclopentyl-NH-CH₂CH₂CH₂-* | 95 | 3.37 | 505 |
| 255 | pyrrolidinyl-CH₂CH₂CH₂-* | 95 | 3.23 | 491 |
| 256 | piperidinyl-CH₂CH₂CH₂-* | 95 | 3.28 | 505 |

-continued

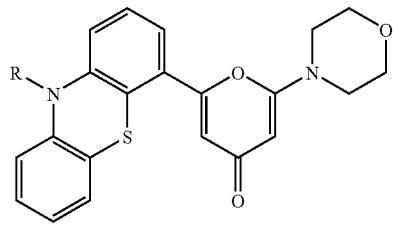

| Compound | R | Purity (%) | Retention Time (Mins) | M⁺ + 1 |
|---|---|---|---|---|
| 257 | ![structure] 2,6-dimethylmorpholine-N-propyl* | 95 | 3.3 | 535 |
| 258 | ![structure] (2R,6S)-dimethylmorpholine-N-propyl* | 95 | 3.33 | 535 |
| 259 | ![structure] morpholine-N-propyl* | 95 | 3.2 | 507 |
| 260 | ![structure] azepane-N-propyl* | 95 | 3.38 | 519 |
| 261 | ![structure] azepane-N-NH-propyl* | 85 | 3.34 | 534 |
| 262 | ![structure] morpholine-N-NH-propyl* | 95 | 3.17 | 552 |
| 263 | ![structure] piperidine-N-CH2CH2-NH-propyl* | 85 | 2.95 | 548 |
| 264 | ![structure] pyrrolidine-N-CH2CH2-NH-propyl* | 95 | 2.98 | 534 |
| 265 | ![structure] 1-methylpyrrolidine-2-CH2CH2-NH-propyl* | 95 | 2.95 | 548 |
| 266 | ![structure] pyridine-2-CH2-NH-propyl* | 85 | 3.33 | 528 |

-continued
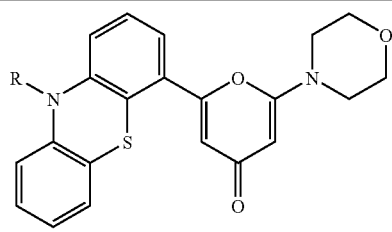
| Compound | R | Purity (%) | Retention Time (Mins) | M⁺ + 1 |
|---|---|---|---|---|
| 267 | pyridin-3-yl-CH₂-NH-(CH₂)₃-* | 90 | 3.13 | 528 |
| 268 | pyridin-4-yl-CH₂-N(Et)-(CH₂)₃-* | 90 | 3.18 | 556 |
| 269 | pyridin-2-yl-CH₂CH₂-N(Me)-(CH₂)₃-* | 85 | 3.33 | 556 |
| 270 | 4-methylpiperazin-1-yl-(CH₂)₃-NH-(CH₂)₃-* | 95 | 2.93 | 577 |
| 271 | 1H-imidazol-4-yl-CH₂CH₂-NH-(CH₂)₃-* | 95 | 2.93 | 531 |
| 272 | morpholin-4-yl-CH₂CH₂-NH-(CH₂)₃-* | 95 | 3.07 | 550 |
| 273 | morpholin-4-yl-(CH₂)₃-NH-(CH₂)₃-* | 95 | 2.93 | 569 |
| 274 | 4-benzylpiperazin-1-yl-CH₂CH₂-NH-(CH₂)₃-* | 90 | 3.08 | 639 |
| 275 | 4-Boc-piperazin-1-yl-CH₂CH₂-NH-(CH₂)₃-* | 85 | 3.47 | 649 |
| 276 | Et₂N-CH₂CH₂-NH-(CH₂)₃-* | 90 | 2.93 | 536 |

-continued

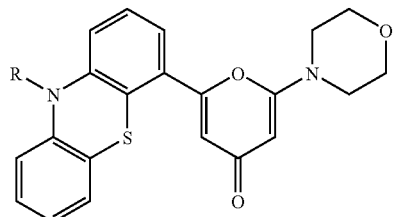

| Compound | R | Purity (%) | Retention Time (Mins) | M+ + 1 |
|---|---|---|---|---|
| 277 | Et₂N-CH₂CH₂CH₂-NH-CH₂CH₂CH₂-* | 95 | 2.94 | 550 |
| 278 | (iPr)₂N-CH₂CH₂-NH-CH₂CH₂CH₂-* | 95 | 2.98 | 564 |
| 279 | Me₂N-CH₂CH₂-N(Me)-CH₂CH₂CH₂-* | 95 | 2.95 | 522 |
| 280 | H₂N-CH₂CH₂-NH-CH₂CH₂CH₂-* | 95 | 2.91 | 480 |
| 281 | Bn(NMe₂CH₂CH₂)N-CH₂CH₂CH₂-* | 85 | 3.76 | 598 |
| 282 | Me₂N-CH₂CH₂-NH-CH₂CH₂CH₂-* | 95 | 2.93 | 508 |
| 283 | MeHN-CH₂CH₂-NH-CH₂CH₂CH₂-* | 95 | 2.93 | 508 |
| 284 | Me₂N-CH₂CH₂CH₂-NH-CH₂CH₂CH₂-* | 90 | 2.92 | 522 |
| 285 | MeO-CH₂CH₂CH₂-NH-CH₂CH₂CH₂-* | 95 | 3.28 | 509 |
| 286 | EtO-CH₂CH₂CH₂-NH-CH₂CH₂CH₂-* | 95 | 3.38 | 523 |
| 287 | (2-oxoimidazolidin-1-yl)-CH₂CH₂-NH-CH₂CH₂CH₂-* | 90 | 3.16 | 549 |
| 288 | (4-methylpiperazin-1-yl)-CH₂CH₂CH₂-* | 95 | 3.1 | 520 |

-continued

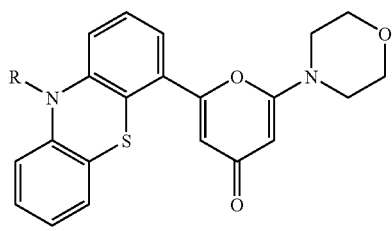

| Compound | R | Purity (%) | Retention Time (Mins) | M⁺ + 1 |
|---|---|---|---|---|
| 289 | piperazine-N-(2-methylphenyl), propyl linker | 50 | 3.71 | 596 |
| 290 | piperazine-N-(pyridin-2-yl), propyl linker | 95 | 3.24 | 583 |
| 291 | piperazine-N-(pyridin-3-yl), propyl linker | 85 | 2.95 | 583 |
| 292 | piperazine-N-CH₂CH₂-O-CH₂CH₂-OH, propyl linker | 85 | 3.07 | 594 |
| 293 | N-acetyl piperazine, propyl linker | 85 | 3.15 | 548 |
| 294 | piperazine-N-(2,4-dimethylphenyl), propyl linker | 85 | 3.8 | 610 |
| 295 | piperazine-N-(pyrimidin-2-yl), propyl linker | 95 | 3.36 | 584 |
| 296 | iPrNH-C(O)-CH₂-piperazine, propyl linker | 95 | 3.31 | 605 |

-continued

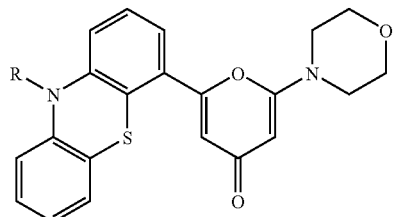

| Compound | R | Purity (%) | Retention Time (Mins) | M⁺ + 1 |
|---|---|---|---|---|
| 297 | piperazine-N-(2-fluorophenyl), propyl linker | 95 | 3.61 | 600 |
| 298 | Boc-piperazine, propyl linker | 95 | 3.53 | 606 |
| 299 | 1-(ethoxycarbonylmethyl)-3-oxopiperazine, propyl linker | 95 | 3.66 | 606 |
| 300 | 4-(2-hydroxyethyl)piperazine, propyl linker | 95 | 3.14 | 550 |
| 301 | 4-(furan-2-carbonyl)piperazine, propyl linker | 95 | 3.22 | 564 |
| 302 | morpholine, propyl linker | 95 | 3.32 | 600 |
| 303 | piperazine, propyl linker | 95 | 3.06 | 506 |
| 304 | 4-(2-dimethylaminoethyl)piperazine, propyl linker | 95 | 2.98 | 577 |
| 305 | 1-(morpholinocarbonylmethyl)-3-oxopiperazine, propyl linker | 95 | 3.19 | 633 |

-continued
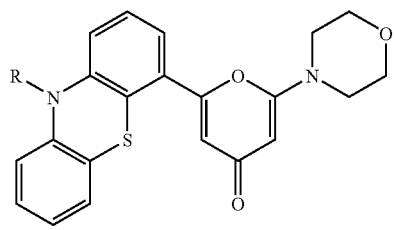
| Compound | R | Purity (%) | Retention Time (Mins) | M⁺ + 1 |
|---|---|---|---|---|
| 306 | HO-cyclohexyl-NH-(CH₂)₃-* | 95 | 3.18 | 535 |
| 307 | N-methyl-piperidin-4-yl-NH-(CH₂)₃-* | 95 | 2.93 | 534 |
| 308 | 2-(hydroxymethyl)cyclohexyl-NH-(CH₂)₃-* | 90 | 3.41 | 549 |
| 309 | 1-benzylpiperidin-4-yl-NH-(CH₂)₃-* | 90 | 3.23 | 510 |
| 310 | 2-(ethoxycarbonyl)cyclohexyl-NH-(CH₂)₃-* | 95 | 3.55 | 591 |
| 311 | 1-Boc-piperidin-4-yl-NH-(CH₂)₃-* | 95 | 3.63 | 620 |
| 312 | 4-(ethoxycarbonyl)piperidin-1-yl-(CH₂)₃-* | 95 | 3.46 | 577 |
| 313 | 4-(hydroxymethyl)piperidin-1-yl-(CH₂)₃-* | 95 | 3.21 | 535 |

-continued
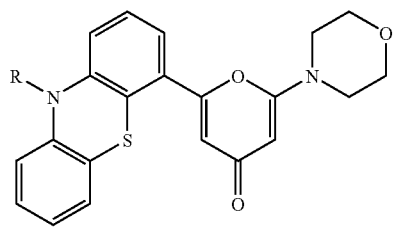
| Compound | R | Purity (%) | Retention Time (Mins) | M⁺ + 1 |
| --- | --- | --- | --- | --- |
| 314 | (1-(3-hydroxymethyl)piperidinyl)propyl | 95 | 3.22 | 535 |
| 315 | (1-(3-ethoxycarbonyl)piperidinyl)propyl | 85 | 3.43 | 577 |
| 316 | (1-(4-hydroxy)piperidinyl)propyl | 85 | 3.14 | 521 |
| 317 | (1-(4-carboxamido)piperidinyl)propyl | 85 | 3.14 | 548 |
| 318 | Boc-NH-(CH₂)₄-NH-(CH₂)₃-* | 85 | 3.63 | 622 |
| 319 | (2S,4R)-methyl 4-hydroxy-1-propylpyrrolidine-2-carboxylate | 85 | 3.26 | 565 |
| 320 | bis(2-methoxyethyl)aminopropyl | 90 | 3.36 | 553 |
| 321 | ((2,2-dimethyl-1,3-dioxolan-4-yl)methyl)aminopropyl | 85 | 3.11 | 551 |

-continued
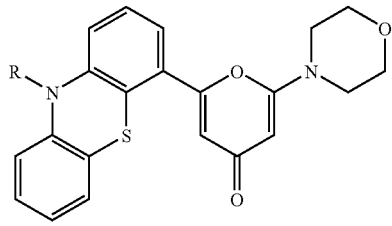
| Compound | R | Purity (%) | Retention Time (Mins) | M⁺ + 1 |
|---|---|---|---|---|
| 322 | HO-, HO-, OH, tris(hydroxymethyl) group -NH- | 95 | 3.1 | 541 |
| 323 | HO-, HO- bis(hydroxymethyl) -NH- | 95 | 3.12 | 511 |
| 324 | methyl ester with HO- serine derivative -NH- | 95 | 3.2 | 539 |
| 325 | benzyl HO- derivative -NH- | 95 | 3.46 | 571 |
| 326 | cycloheptyl OH -NH- | 95 | 3.45 | 563 |
| 327 | HO-, HO- N(CH₂CH₂OH)₂ | 95 | 3.13 | 525 |
| 328 | cyclohexyl OH -NH- | 95 | 3.38 | 549 |
| 329 | HO- CH(CH₃) -NH- | 95 | 3.18 | 495 |
| 330 | phenyl thiadiazole -NH- | 90 | 4.74 | 597 |

-continued
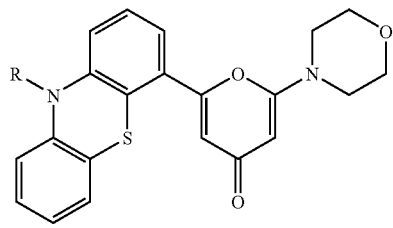
| Compound | R | Purity (%) | Retention Time (Mins) | M+ + 1 |
|---|---|---|---|---|
| 331 | 1-methyl-1,4-diazepane-propyl | 95 | 2.93 | 534 |
| 332 | 1,4-diazepane-propyl | 95 | 2.93 | 520 |
| 333 | 4-Boc-1,4-diazepane-propyl | 95 | 3.56 | 620 |
| 334 | 4-(hydroxymethyl)-1,4-diazepane-propyl | 95 | 2.91 | 564 |
| 335 | 4-(tetrahydrofuran-2-carbonyl)-1,4-diazepane-propyl | 95 | 3.23 (recorded on Waters Micromass) | 604 |
| 336 | biotinyl-aminohexanoyl-aminoethylamino-propyl | 99 | — | 819 |

Example 5

2-(7-Amino-9H-thioxanthen-4-yl)-6-morpholin-4-yl-pyran-4-one N-amide derivatives

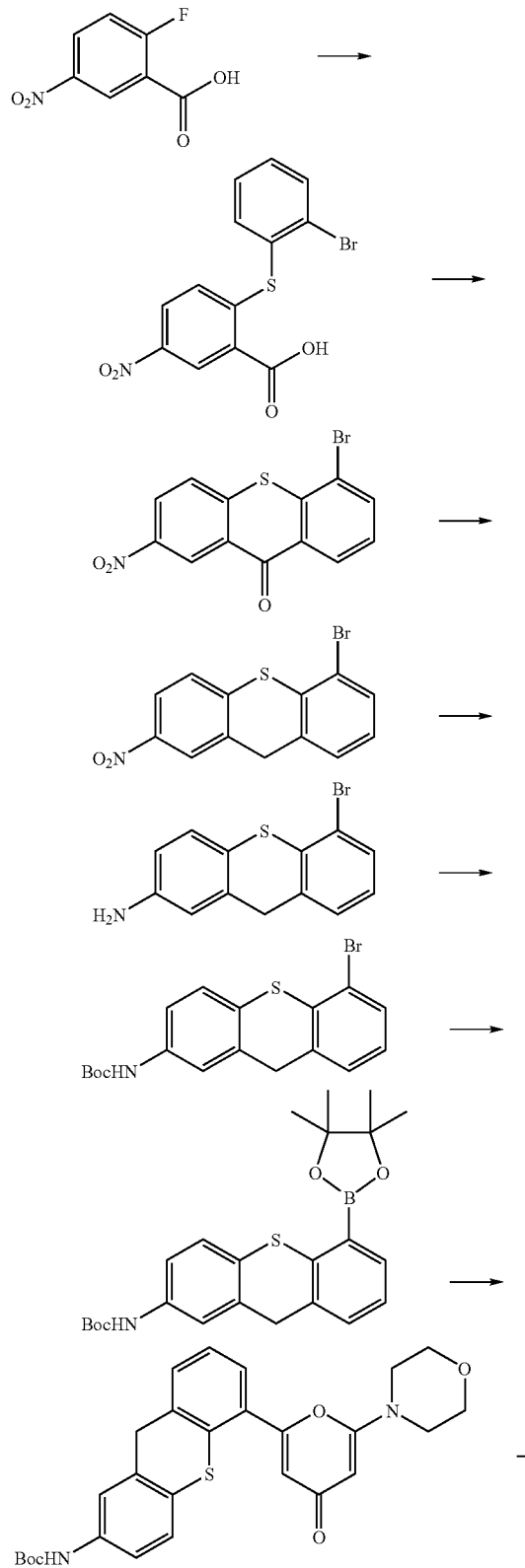

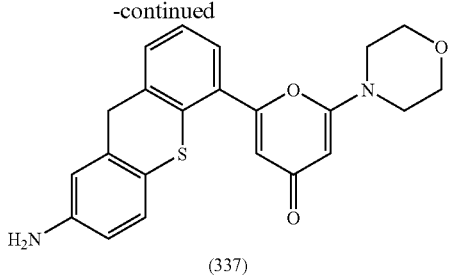

(337)

2-(2-Bromo-phenylsulfanyl)-5-nitro-benzoic acid

2-Bromobenzenethiol (7.2 ml, 85.9 mmol) was added to a solution of KOH (9.6 g, 172 mmol) in water (50 ml) degassed for 15 minutes. 2-Fluoro-5-nitrobenzoic acid (15.9 g, 85.9 mmol) was added to the reaction mixture, which was refluxed under a nitrogen atmosphere overnight. The reaction was cooled to room temperature and was acidified (pH 1) with conc. HCl. The precipitate formed was filtered and dried overnight in a vacuum oven (50° C.) to give the crude title compound as a pale yellow solid (30 g, 99%). The product was used without further purification. m/z (LC-MS, ESP), RT=4.51min, (M$^-$–1)=352-354, (1:1, bromine isotope ratio present).

5-Bromo-2-nitro-thioxanthen-9-one 2-(2-Bromo-phenylsulfanyl)-5-nitro-benzoic acid (34 g, 96 mmol) was suspended in methanesulphonic acid (400 ml) and heated at 150° C. The crude mixture was slowly poured onto ice with vigorous stirring and the precipitate formed was filtered. The solid was suspended into water (50 ml) quenched to pH 7-8 with conc. ammonia solution and filtered. The yellow/lime colored solid was dried under vacuum at 50° C. to give the crude title compound, which was used without any further purification (23.09 g, 72%).

5-Bromo-2-nitro-9H-thioxanthene

To a cooled (0° C.) suspension of 5-bromo-2-nitro-thioxanthen-9-one (23.03 g, 68.5 mmol) in anhydrous tetrahydrofuran (100 ml) under nitrogen atmosphere, was added drop wise borane-THF complex (151 ml, 1.0M in THF). The mixture was allowed to warm to room temperature with stirring overnight. The reaction mixture was cooled (0° C.) and the excess borane was quenched with acetone. The solvent was evaporated in vacuo and the residue was triturated in saturated sodium bicarbonate (100 ml). The solid was filtered, washed with water and dried overnight in a vacuum dissicator to give the title compound (22.07 g, 100%). $^1$HNMR (300 MHz, CDCl$_3$): $\delta_H$=4.02 (2H, s), 7.17 (1H, m), 7.27 (1H, m), 7.51 (1H, m), 7.62 (1H, m), 8.09 (1H, m), 8.20 (1H, d).

5-Bromo-9H-thioxanthen-2-ylamine

Zn dust (34.87 g, 533 mmol) was added to a stirred solution of 5-bromo-2-nitro-9H-thioxanthene (28.64 g, 88.9 mmol) in glacial acetic acid (300 ml) at 0° C. (ice bath). After one hour the ice bath was removed and the solution was left to react overnight at room temperature. The mixture was filtered through a pad of Celite and washed with copious amount of dichloromethane and the filtrate was evaporated in vacuo. Water was added (800 ml) to the residue and the pH was adjusted to pH 8 by addition of concentrated ammonia (100 ml). The solid formed was filtered and dried in a vacuum desiccator to give the title compound (26.64 g) and was used without any further purification. m/z (LC-MS, ESP), RT=4.53 min, (M⁺+1)=294-292, (1:1, bromine isotope ratio present)

(5-Bromo-9H-thioxanthen-2-yl)-carbamic acid tert-butyl ester

Di-tert-butyl dicarbonate (22 g, 99 mmol) was added to a solution of 5-bromo-9H-thioxanthen-2-ylamine (19.28 g, 66 mmol) in dry THF (150 ml). The mixture was stirred and heated at 50° C. overnight. The solvent was removed in vacuo and the residue was triturated in water to give a brown solid, which was purified by column chromatography (silica, dichloromethane) to give the title compound as a fluffy white solid (18.28 g, 71%). %). ¹HNMR (300 MHz, CDCl₃): $\delta_H$=1.55 (9H, s), 3.88 (2H, s), 6.45 (1H, bs), 7.06 (2H, m), 7.23 (1H, d), 7.39 (1H, d), 7.45 (1H, d), 7.58 (1H, bs).

[5-(6-Morpholin-4-yl-4-oxo-4H-pyran-2-yl)-9H-thioxanthen-2-yl]-carbamic acid tert-butyl ester (5-Bromo-9H-thioxanthen-2-yl)-carbamic acid tert-butyl ester (1 g, 2.55 mmol), bis(pinacolato)diboron (0.78 g, 3.06 mmol) and potassium acetate (0.75 g, 7.65 mmol) in dry 1,4-dioxane (6 ml). To the yellow suspension was then added PdCl₂(dppf) (0.10 g, 0.13 mmol) and dppf (7 mg, 0.13 mmol). The dark red mixture was heated to 110° C. under a N₂ atmosphere for 24 hours. The crude mixture was purified by flash chromatography (silica, dichloromethane) to give [5-(4,4,5,5-Tetramethyl-[1,3,2]dioxaborolan-2-yl)-9H-thioxanthen-2-yl]-carbamic acid tert-butyl ester as a viscous brown oil which was used without any further purification (1.12 g). [5-(4,4,5,5-Tetramethyl-[1,3,2]dioxaborolan-2-yl)-9H-thioxanthen-2-yl]-carbamic acid tert-butyl ester (1.12 g), 2-chloro-6-morpholin-4-yl-pyran-4-one (0.66 g, 3.06 mmol) and grinded K₂CO₃ (0.71 g, 5.10 mmol) were dissolved in dry 1,4-dioxane (5 ml). The mixture was degassed for 15 mins and Pd(PPh₃)₄ (0.15 g, 0.13 mmol) was then added The dark brown mixture was heated to 100° C. under an atmosphere of N₂ for 24 hour. The reaction mixture was concentrated in vacuo and water (50 ml) was added. The brown solid was filtered, washed with water, dried overnight in a vacuum desiccator and was used without any further purification (1.51 g). m/z (LC-MS, ESP), RT=4.47 min, (M⁺+1)=493

2-(7-Amino-9H-thioxanthen-4-yl)-6-morpholin-4-yl-pyran-4-one (337)

To a solution of [5-(6-Morpholin-4-yl-4-oxo-4H-pyran-2-yl)-9H-thioxanthen-2-yl]-carbamic acid tert-butyl ester (19) (1.08 g, 2.19 mmol) in dichloromethane (10 ml) was added trifluoroacetic acid (2 ml) and left under stirring at room temperature overnight. The solvent was dried in vacuo revealing a viscous dark brown liquid. Saturated sodium bicarbonate solution (20 ml) was added to the residue, which was left to stir for 20 mins. The brown precipitate was filtered, washing with water and left to dry in the vacuum oven overnight (0.77 g, 90%). ¹HNMR (300 MHz, DMSO-d₆): $\delta_H$=3.40 (4H, t), 3.70 (4H, t), 3.77 (2H, s), 5.23 (2H, bs), 5.50 (1H, d), 6.17 (1H, d), 6.44 (1H, dd), 6.65 (1H, d), 7.09 (1H, d), 7.35 (1H, t), 7.47-7.59 (2H, m); m/z (LC-MS, ESP), RT=3.51 minutes, (M⁺+1)=392.

2-(7-Amino-9H-thioxanthen-4-yl)-6-morpholin-4-yl-pyran-4-one N-amide derivatives To a small test tube was added 2-(7-amino-9H-thioxanthen-4-yl)-6-morpholin-4-yl-pyran-4-one (337) (20 mg, 0.05 mmol), dry dimethylacetamide (0.5 ml), triethylamine (8 μl, 0.06 mmol) and chloroacetyl chloride (4 μl, 0.06 mmol) with stirring overnight. The appropriate amine or thiol (20 mg or 20 μl) was then added and left to stir at room temperature overnight. The reaction was purified by preparative HPLC to give the desired products, which are shown below:

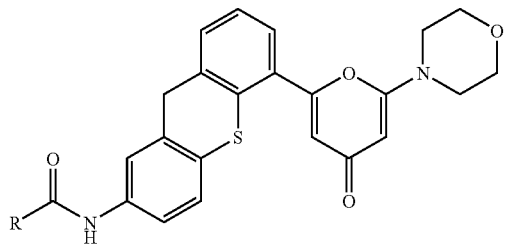

| Compound | R | Purity (%) | Retention Time (Mins) | M⁺+1 |
|---|---|---|---|---|
| 338 | ![structure] | 95 | 3.15 | 561 |
| 339 | ![structure] | 95 | 3.20 | 577 |

-continued
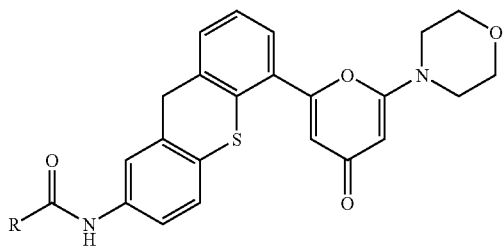
| Compound | R | Purity (%) | Retention Time (Mins) | M⁺+ 1 |
|---|---|---|---|---|
| 340 | HO-CH₂CH₂-O-CH₂CH₂-piperazine-CH₂-* | 90 | 3.40 | 607 |
| 341 | isopropyl-piperazine-CH₂-* | 90 | 3.23 | 561 |
| 342 | ethyl-piperazine-CH₂-* | 95 | 3.18 | 547 |
| 343 | 2-pyridyl-piperazine-CH₂-* | 95 | 3.23 | 596 |
| 344 | 4-fluorophenyl-piperazine-CH₂-* | 95 | 3.69 | 613 |
| 345 | 2-pyrimidinyl-piperazine-CH₂-* | 90 | 3.37 | 597 |
| 346 | isopropyl-NH-C(O)-CH₂-piperazine-CH₂-* | 85 | 3.24 | 618 |
| 347 | (CH₃)₂N-CH₂CH₂-piperazine-CH₂-* | 90 | 2.91 | 590 |

-continued
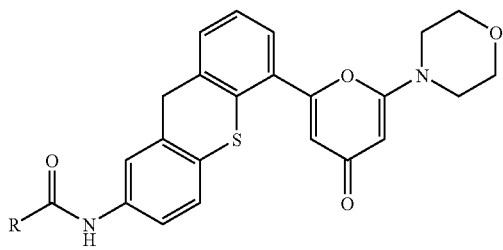
| Compound | R | Purity (%) | Retention Time (Mins) | M⁺+ 1 |
|---|---|---|---|---|
| 348 | *piperazine with hydroxyethyl* | 90 | 3.13 | 563 |
| 349 | *acetyl piperazine ethyl* | 85 | 3.12 | 575 |
| 350 | *HO-ethoxy-ethyl piperazine ethyl* | 85 | 3.03 | 577 |
| 351 | *isopropyl piperazine ethyl* | 90 | 3.17 | 575 |
| 352 | *ethyl piperazine ethyl* | 90 | 3.58 | 561 |
| 353 | *2-pyridyl piperazine ethyl* | 90 | 3.29 | 610 |
| 354 | *4-fluorophenyl piperazine ethyl* | 85 | 3.23 | 627 |

-continued

| Compound | R | Purity (%) | Retention Time (Mins) | M⁺+ 1 |
|---|---|---|---|---|
| 355 | (pyrimidin-2-yl-piperazinyl-ethyl) | 90 | 2.94 | 611 |
| 356 | (dimethylamino-ethyl-piperazinyl-ethyl) | 90 | 2.94 | 604 |

Example 6

Synthesis of 2(-(7-hydroxy-thianthren-1-yl)-6-morpholin-4-yl pyran-4-one ether and acetamide derivatives)

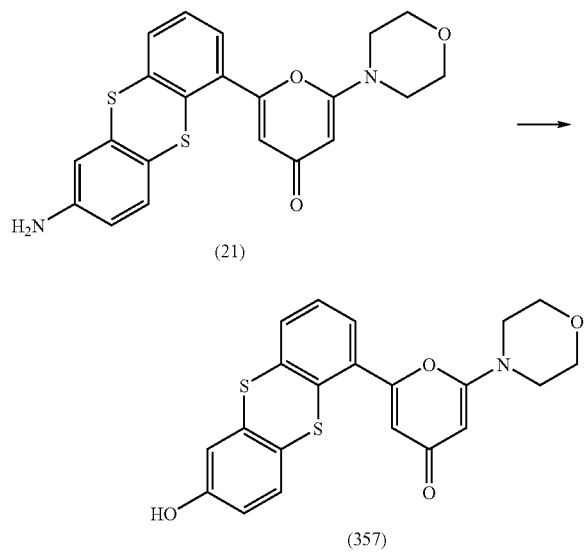

2-(7-Hydroxy-thianthren-1-yl)-6-morpholin-4-yl-pyran-4-one (357)

To a solution of 2-(7-Amino-thianthren-1-yl)-6-morpholin-4-yl-pyran-4-one (21) (575 mg, 1.4 mmol) was suspended in ethanol (5 mL) was added tetrafluoroboric acid (54 wt % in ether, 3 ml, 1.68 mmol). The mixture was stirred at room temperature for 10 minutes before being cooled to 0° C. Butyl nitrite (220 µl, 2.8 mmol) was then added dropwise and the mixture stirred for 30 minutes before the addition of diethyl ether (40 ml) which caused a precipitate to form. The solid was collected by filtration and washed with cold diethylether (30 ml) then added to a solution of cupric nitrate trihidrate (210 g, 870 mmol) and cuprous oxide (190 mg, 1.31 mmol) in water (300 ml). The reaction was stirred for 12 hours and then filtered. The filtrant was washed with water, dried in a desiccator and used without further purification give the title compound (0.58 g, 100%). NMR (300 MHz, CDCl$_3$): $\delta_H$=10.08 (1H, bs); 7.76 (1H, dd); 7.60 (1H, dd); 7.46 (1H, dd); 7.35 (1H, dd); 7.02 (1H, d); 6.74 (1H, dd); 6.24 (1H, d); 5.55 (1H, d); 3.69 (H, m), 3.36 (4H, m); m/z (LC-MS, ESP), RT=3.83 min, (M⁺+1)=412

2-[7-(2-Bromo-ethoxy)-thianthren-1-yl]-6-morpholin-4-yl-pyran-4-one ether derivatives To a solution of 2-(7-Hydroxy-thianthren-1-yl)-6-morpholin-4-yl-pyran-4-one (357) (20 mg, 0.049 mmol) in anhydrous DMF (1 ml) was added powdered potassium carbonate (20 mg, 0.147 mmol) and dibromoethane (0.019 ml, 0.23 mmol). The mixture was stirred for 16 hours at 60° C. before diisopropylethylamine (0.29 mmol) the appropriate amine (0.29 mmol) were added. The reaction was maintained, with stirring, at 60° C. for 24 hrs after which time the crude mixture was purified by preparative HPLC to give the desired compounds, which are shown below:

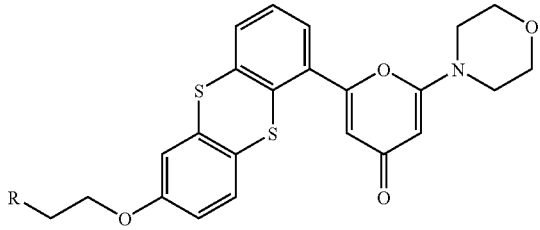
| Compound | R | Purity (%) | Retention Time (Mins) | M⁺+1 |
|---|---|---|---|---|
| 358 | piperidine-CH2CH2-NH-* | 85 | 3.19 | 566 |
| 359 | (2R,6S)-2,6-dimethylmorpholine-N-* | 90 | 3.61 | 553 |
| 360 | MeO-CH2CH2-piperazine-N-* | 90 | 3.55 | 582 |
| 361 | N-methylpiperazine-N-* | 90 | 3.36 | 538 |
| 362 | 2-pyrimidinyl-piperazine-N-* | 85 | 3.61 | 602 |
| 363 | HO-CH2CH2-piperazine-N-* | 90 | 3.36 | 568 |
| 364 | isopropyl-piperazine-N-* | 90 | 3.45 | 566 |
| 365 | ethyl-piperazine-N-* | 90 | 3.42 | 552 |
| 366 | 4-pyridyl-CH2-NH-* | 90 | 3.31 | 546 |
| 367 | HO-CH2CH2-NH-* | 95 | 3.31 | 499 |

-continued
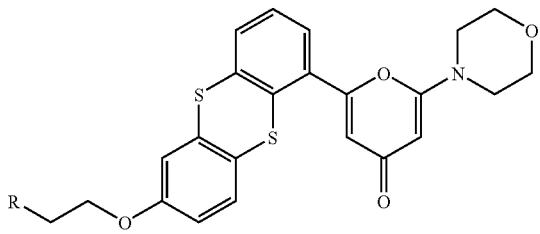
| Compound | R | Purity (%) | Retention Time (Mins) | M+ + 1 |
|---|---|---|---|---|
| 368 | piperidinyl | 95 | 3.55 | 523 |
| 369 | imidazolidinone-ethylamino | 95 | 3.38 | 567 |
| 370 | piperazinyl | 85 | 3.31 | 524 |
| 371 | 4-methyl-1,4-diazepan-1-yl | 85 | 3.16 | 552 |
| 372 | 1,4-diazepan-1-yl | 90 | 3.08 | 538 |
| 373 | N,N-bis(2-hydroxyethyl)amino | 95 | 3.36 | 543 |
| 374 | N,N-bis(2-methoxyethyl)amino | 95 | 3.62 | 571 |
| 375 | azepan-1-yl | 90 | 3.64 | 537 |
| 376 | N,N-diethylamino | 95 | 3.56 | 511 |
| 377 | 1-benzylpiperidin-4-ylamino | 95 | 3.14 | 628 |

-continued
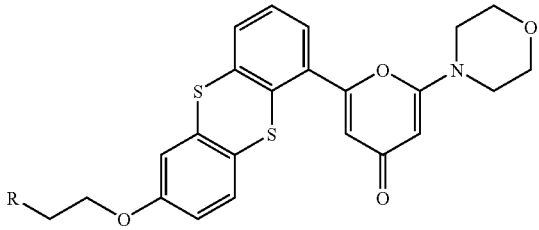
| Compound | R | Purity (%) | Retention Time (Mins) | M⁺+1 |
|---|---|---|---|---|
| 378 | 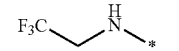 | 95 | 3.29 | 566 |
| 379 | 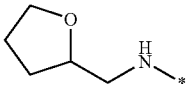 | 85 | 4.36 | 537 |
| 380 | 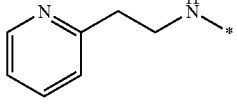 | 85 | 3.47 | 539 |
| 381 | 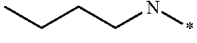 | 95 | 3.48 | 560 |
| 382 | 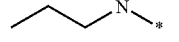 | 90 | 3.60 | 511 |
| 383 | 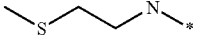 | 90 | 3.46 | 497 |
| 384 | 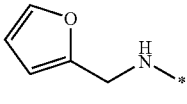 | 85 | 3.51 | 529 |
| 385 | 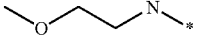 | 85 | 3.53 | 535 |
| 386 | 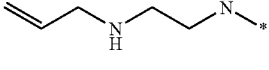 | 95 | 3.42 | 513 |
| 387 | 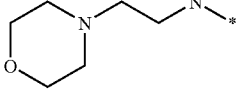 | 95 | 3.48 | 495 |
| 388 | 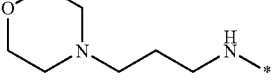 | 90 | 3.21 | 568 |
| 389 |  | 90 | 3.04 | 582 |

-continued

| Compound | R | Purity (%) | Retention Time (Mins) | M⁺+ 1 |
|---|---|---|---|---|
| 390 | HO, HO, HO–C–NH–* | 95 | 3.28 | 559 |
| 391 | imidazole-CH₂CH₂-NH–* | 90 | 3.03 | 549 |
| 392 | piperazinone with CH₂C(O)OEt substituent, N–* | 95 | 3.96 | 624 |
| 393 | pyrrolidine N–* | 90 | 3.44 | 509 |
| 394 | 3-(ethoxycarbonyl)piperidine N–* | 95 | 3.66 | 595 |
| 395 | 4-(furan-2-carbonyl)piperazine N–* | 95 | 3.51 | 618 |
| 396 | 4-(ethoxycarbonyl)piperidine N–* | 95 | 3.65 | 595 |
| 397 | HO-CH₂CH₂-S-CH₂CH₂-NH–* | 85 | 3.36 | 559 |

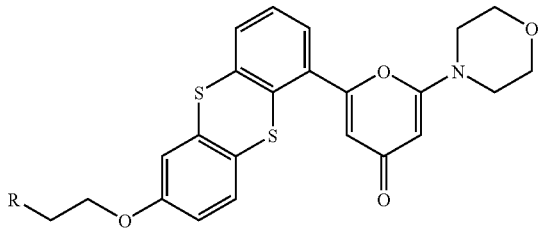

| Compound | R | Purity (%) | Retention Time (Mins) | M⁺+ 1 |
|---|---|---|---|---|
| 398 | (pyridin-2-ylethyl)(methyl)amino | 90 | 3.56 | 574 |
| 399 | 4-(pyridin-2-yl)piperazin-1-yl | 95 | 3.46 | 601 |
| 400 | (S)-(1-methoxy-3-hydroxy-1-oxopropan-2-yl)amino | 85 | 3.38 | 557 |
| 402 | 4-(2-(2-hydroxyethoxy)ethyl)piperazin-1-yl | 90 | 3.34 | 612 |
| 403 | morpholin-4-yl | 95 | | 525 |

[6-(6-Morphol in-4-yl -4-oxo-4H-pyran-2-yl) -thianthren-2-yloxy]-acetic acid methyl ester To a suspension of 2-(7-Hydroxy-thianthren-1-yl)-6-morpholin-4-yl-pyran-4-one (357) (20 mg, 0.049 mmol) in anhydrous DMF was added powdered potassium carbonate (20 mg, 0.145) followed by methyl bromoacetate (0.01 ml, 0.106 mmol). The mixture was warmed to 60° C. and maintained at this temperature with stirring for 2 hours. The reaction was cooled, poured into water (5 ml) and extracted using ethyl acetate (3*5 ml), then washed with water (2*5 ml). The combined organics were then dried (MgSO4), filtered and concentrated in vacuo to give a yellow solid (22 mg, 94%) which corresponded to the title compound and was used without any further purification. m/z (LC-MS, ESP), RT=4.13 min, (M⁺+1)=484

[6-(6-Morpholin-4-yl-4-oxo-4H-pyran-2-yl)-thianthren-2-yloxy]-acetic acid sodium salt To a solution of [6-(6-Morpholin-4-yl-4-oxo-4H-pyran-2-yl)-thianthren-2-yloxy]-acetic acid methyl ester (22 mg, 0.045 mmol in methanol (2 ml) was added solid sodium hydroxide (2 mg, 0.045 mmol). The mixture was stirred vigorously and heated to 60° C. for 1 hour. After this time, the mixture was concentrated in vacuo to dryness to give the title compound (22.4 mg, 100%) and used without any further purification.

2-[6-(6-Morpholin-4-yl-4-oxo-4H-pyran-2-yl)-thianthren-2-yloxy]-acetamide derivatives To a solution of [6-(6-Morpholin-4-yl-4-oxo-4H-pyran-2-yl)-thianthren-2-yloxy]-acetic acid sodium salt (22.4 mg, 0.045 mmol) in dry DMF (1 ml) was added HBTU (25.9 mg, 0.068 mmol), diisopropylethyl amine (0.1 ml) and the appropriate amine (0.137 mmol). The mixture was stirred at room temperature for 72 hours after which time the crude mixture was purified by preparative HPLC to give the desired compounds, which are shown below:

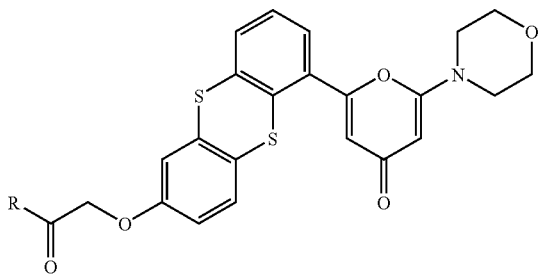
| Compound | R | Purity (%) | Retention Time (Mins) | M⁺+ 1 |
|---|---|---|---|---|
| 404 | 4-(dimethylamino)benzyl-NH-* | 85 | 3.75 | 602 |
| 405 | cyclobutyl-NH-* | 95 | 4.29 | 523 |
| 406 | tBuO-C(O)-CH₂-NH-* | 95 | 4.48 | 583 |
| 407 | n-butyl-NH-* | 95 | 4.41 | 525 |
| 408 | morpholino-(CH₂)₃-NH-* | 90 | 3.33 | 596 |
| 409 | NC-CH₂-NH-* | 95 | 3.88 | 508 |
| 410 | (HOCH₂)₃C-NH-* | 95 | 3.50 | 573 |
| 411 | (HOCH₂)₂CH-NH-* | 85 | 3.46 | 543 |
| 412 | 3-oxopiperazine-CH₂-C(O)OEt | 95 | 3.76 | 638 |

-continued
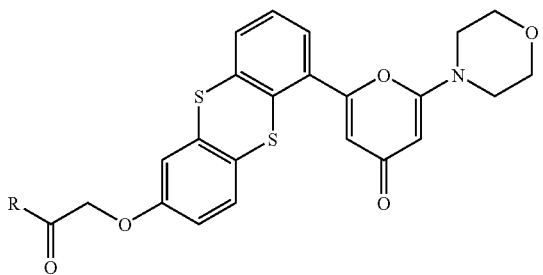
| Compound | R | Purity (%) | Retention Time (Mins) | M⁺+1 |
|---|---|---|---|---|
| 413 | EtO-C(O)-piperidin-3-yl-N-* | 95 | 4.39 | 609 |
| 414 | furan-2-yl-C(O)-piperazin-N-* | 95 | 3.97 | 632 |
| 415 | EtO-C(O)-piperidin-4-yl-N-* | 95 | 4.39 | 609 |
| 416 | H₂N-C(O)-piperidin-4-yl-N-* | 95 | 3.57 | 580 |
| 417 | thiomorpholin-N-* | 95 | 4.24 | 555 |
| 418 | HO-CH₂-piperidin-3-yl-N-* | 95 | 3.81 | 567 |
| 419 | pyridin-3-yl-NH-* | 85 | 3.63 | 546 |
| 420 | 2-hydroxycycloheptyl-CH₂-NH-* | 95 | 4.25 | 595 |

-continued
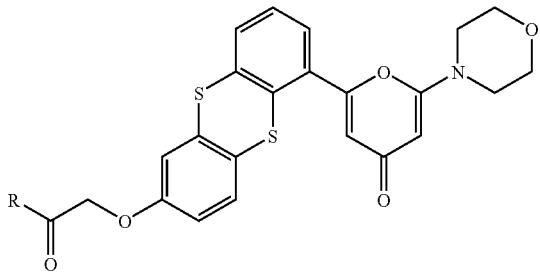
| Compound | R | Purity (%) | Retention Time (Mins) | M⁺+ 1 |
|---|---|---|---|---|
| 421 | (ethyl ester, phenyl, NH*) | 90 | 4.76 | 631 |
| 422 | (4-hydroxy proline methyl ester, N*) | 95 | 3.67 | 597 |
| 423 | (tryptophan methyl ester, NH*) | 95 | 4.54 | 670 |
| 424 | (serine benzyl ester, NH*) | 95 | 4.24 | 647 |
| 425 | (2-(pyridin-2-yl)ethyl-N-methyl, N*) | 95 | 3.45 | 588 |
| 426 | (4-(pyridin-2-yl)piperazin-1-yl, N*) | 90 | 3.52 | 615 |
| 427 | (3-morpholinopropyl, NH*) | 95 | 3.70 | 571 |

-continued

| Compound | R | Purity (%) | Retention Time (Mins) | M⁺+ 1 |
|---|---|---|---|---|
| 428 | HO-CH₂CH₂-O-CH₂CH₂-piperazinyl-* | 95 | 3.28 | 626 |
| 429 | acetyl-piperazinyl-* | 95 | 3.64 | 580 |
| 430 | 4-acetylphenyl-piperazinyl-* | 90 | 4.38 | 655 |
| 431 | 2-methylphenyl-piperazinyl-* | 95 | 5.05 | 628 |
| 432 | 4-fluorophenyl-piperazinyl-* | 90 | 4.71 | 632 |
| 433 | (2R,6S)-2,6-dimethylmorpholinyl-* | 95 | 4.24 | 567 |
| 434 | (CH₃)₂NCH₂CH₂N(CH₃)-* | 90 | 3.36 | 554 |
| 435 | CH₃O-CH₂CH₂-piperazinyl-piperazinyl-* | 90 | 3.41 | 596 |

-continued
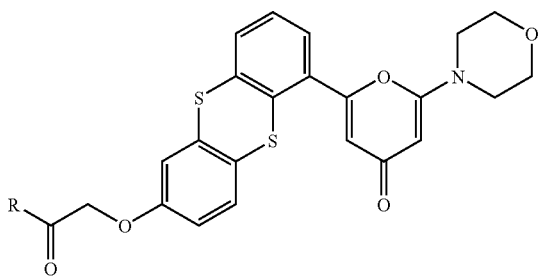
| Compound | R | Purity (%) | Retention Time (Mins) | M⁺+1 |
|---|---|---|---|---|
| 436 | HO-CH₂CH₂-N(piperazinyl)-* | 95 | 3.32 | 582 |
| 437 | isopropyl-piperazinyl-* | 95 | 3.41 | 580 |
| 438 | ethyl-piperazinyl-* | 95 | 3.35 | 566 |
| 439 | 4-pyridyl-CH₂-NH-* | 85 | 3.44 | 560 |
| 440 | piperidinyl-* | 95 | 4.46 | 537 |
| 441 | (2-oxoimidazolidin-1-yl)ethyl-NH-* | 90 | 3.61 | 581 |
| 442 | 4-methyl-[1,4]diazepan-1-yl-* | 95 | 3.35 | 566 |
| 443 | [1,4]diazepan-1-yl-* | 90 | 3.34 | 552 |
| 444 | bis(2-hydroxyethyl)amino-* | 90 | 3.52 | 557 |

-continued

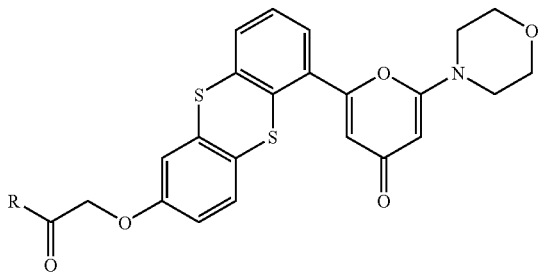

| Compound | R | Purity (%) | Retention Time (Mins) | M⁺+ 1 |
|---|---|---|---|---|
| 445 | MeO—CH₂CH₂—N(CH₂CH₂—OMe)—* | 90 | 4.17 | 585 |
| 446 | azepan-1-yl—* | 95 | 4.56 | 551 |
| 447 | Et₂N—* | 95 | 4.34 | 525 |
| 448 | Me₂N—* | 95 | 3.91 | 497 |
| 449 | 4-(pyrimidin-2-yl)piperazin-1-yl—* | 90 | 4.27 | 616 |
| 450 | 4-methylpiperazin-1-yl—* | 90 | 3.34 | 552 |

Example 7

5-(6-Morpholin-4-yl-4-oxo-4H-pyran-2-yl)-9H-thioxanthene-2-sulfonic acid amide derivatives, 2-[5-(6-Morpholin-4-yl-4-oxo-4H-pyran-2-yl)-9H-thioxanthen-2-yloxy]-acetamide derivatives and 2-[7-(2-Amino-ethoxy)-9H-thioxanthen-4-yl]-6-morpholin-4-yl-pyran-4-one derivatives

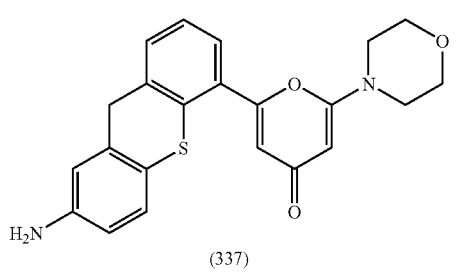

(337)

-continued

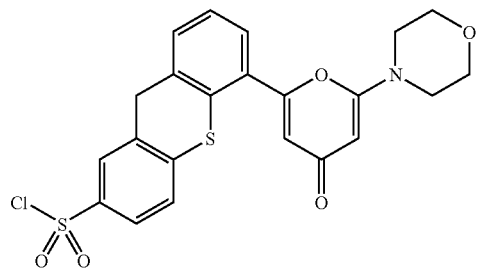

5-(6-Morpholin-4-yl-4-oxo-4H-pyran-2-yl)-9H-thioxanthene-2-sulfonyl chloride Tetrafluorboric acid (supplied as 54 wt % in diethylether, 5.5 ml, 39.92 mmol) was added to a mixture of 2-(7-Amino-9H-thioxanthen-4-yl)-6-morpholin-4-yl-pyran-4-one (337) (1.03 g, 2.61 mmol) suspended in ethanol (10 ml). The reaction was stirred for 10 minutes at room temperature before being cooled to 0° C. and butyl nitrite (600 μl, 5.1 mmol) added. The reaction was then stirred at room temperature for 1 hour before it was poured into diethyl ether (80 ml) and the precipitate collected by filtration. The collected solid was washed with cold ether (60 ml) and then added to a saturated solution of sulphur dioxide in acetic acid*. The mixture was stirred at room temperature for 2 hours whereupon it was extracted into $CH_2Cl_2$ (3×30 ml). The combined dichloromethane extracts were washed with water (1×20 m), dried using MgSO4, filtered and concentrated in vacuo to give the title compound which was used without further purification (1.19 g, 100%), m/z (LC-MS, ESP), RT=4.46 min, (M$^+$+1)= 478 *Acidic $SO_2$ solution prepared by bubbling $SO_2$ gas through a vigorously stirred solution of acetic acid (100 ml) until 10 g of gas had been dissolved. The solution was then treated with a suspension of copper (II) chloride (4 g) in water (10 ml). The mixture was then stirred and filtered to give an emerald green solution which was used without any further purification.

5-(6-Morpholin-4-yl-4-oxo-4H-pyran-2-yl)-9H-thioxanthene-2-sulfonic acid amide derivatives 5-(6-Morpholin-4-yl-4-oxo-4H-pyran-2-yl)-9H-thioxanthene-2-sulfonyl chloride (20 mg, 0.02 mmol) was diluted in DMF (1 ml) and to this solution was added the appropriate amine (0.04 mmol) and diisopropylethyl amine (80 μl, 0.46 mmol). After stirring the reaction mixture for 24 hours at room temperature the crude mixture was purified by preparative HPLC to give the desired compounds, which are shown below:

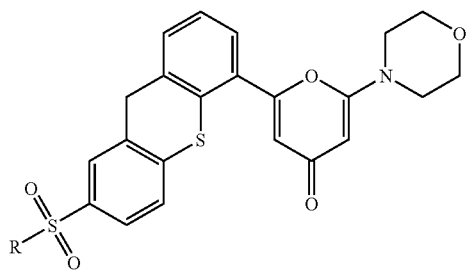

| Compound | R | Purity (%) | Retention Time (Mins) | M$^+$+1 |
|---|---|---|---|---|
| 452 | morpholine-N-* | 95 | 3.13 | 527 |
| 453 | 1-methylpyrrolidin-2-yl-CH₂CH₂-NH-* | 95 | 3.32 | 568 |
| 454 | F₃C-CH₂-NH-* | 90 | 4.17 | 539 |
| 455 | (tetrahydrofuran-2-yl)-CH₂-NH-* / (tetrahydrofuran-2-yl)-CH₂-NH-* | 95 | 3.95 | 541 |
| 456 | pyridin-2-yl-CH₂CH₂-NH-* | 95 | 3.35 | 561 |
| 457 | n-butyl-NH-* | 100 | 4.14 | 513 |
| 458 | n-propyl-NH-* | 95 | 4.20 | 499 |

-continued
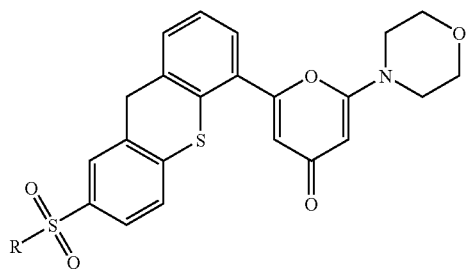
| Compound | R | Purity (%) | Retention Time (Mins) | M⁺+1 |
|---|---|---|---|---|
| 459 | methylthioethyl-NH* | 90 | 4.13 | 531 |
| 460 | furan-2-ylmethyl-NH* | 100 | 4.14 | 537 |
| 461 | methoxyethyl-NH* | 100 | 3.83 | 515 |
| 462 | allyl-NH* | 95 | 4.03 | 497 |
| 463 | morpholinopropyl-NH* | 95 | 3.29 | 584 |
| 464 | cyanomethyl-NH* | 95 | 3.86 | 496 |
| 465 | (1H-imidazol-4-yl)ethyl-NH* | 95 | 3.27 | 551 |
| 466 | 1,3-dihydroxypropan-2-yl-NH* | 90 | 3.38 | 531 |
| 467 | morpholin-4-yl-NH* | 90 | 3.78 | 542 |
| 468 | pyrrolidin-1-yl* | 95 | 4.30 | 511 |
| 469 | 4-carbamoylpiperidin-1-yl* | 95 | 3.69 | 568 |

-continued
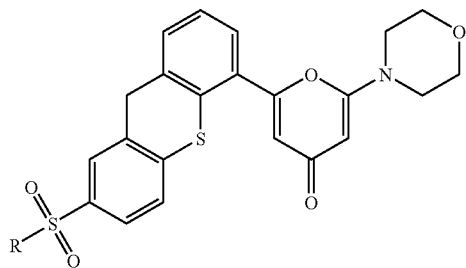
| Compound | R | Purity (%) | Retention Time (Mins) | M⁺+1 |
|---|---|---|---|---|
| 470 | thiomorpholine-N-* | 90 | 4.38 | 543 |
| 471 | HO-CH₂-(3-piperidinyl)-N-* | 100 | 3.98 | 555 |
| 472 | 3-pyridyl-NH-* | 95 | 3.68 | 534 |
| 473 | (2,6-dimethylmorpholino)-CH₂CH₂-O-* | 90 | 3.73 | 561 |
| 474 | cyclobutyl-NH-CH₂CH₂-O-* | 85 | 3.65 | 559 |
| 475 | cyclohexyl-CH₂-NH-CH₂CH₂-O-* | 85 | 3.81 | 541 |
| 476 | 4-acetylpiperazin-1-yl-* | 95 | 3.78 | 568 |
| 477 | piperidin-1-yl-CH₂CH₂-NH-* | 90 | 3.35 | 568 |
| 478 | (2,6-dimethylmorpholino)-* | 90 | 4.44 | 555 |

-continued
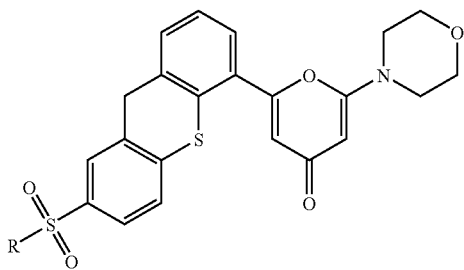
| Compound | R | Purity (%) | Retention Time (Mins) | M⁺+1 |
|---|---|---|---|---|
| 479 | (dimethylamino-ethyl)(methyl)amino | 90 | 3.33 | 542 |
| 480 | 4-methylpiperazin-1-yl | 90 | 3.32 | 540 |
| 481 | 4-(2-hydroxyethyl)piperazin-1-yl | 95 | 3.32 | 570 |
| 482 | 4-ethylpiperazin-1-yl | 90 | 3.38 | 554 |
| 483 | (pyridin-4-ylmethyl)amino | 90 | 3.33 | 548 |
| 484 | (2-hydroxyethyl)amino | 95 | 3.55 | 501 |
| 485 | piperidin-1-yl | 85 | 4.62 | 525 |
| 486 | [2-(2-oxoimidazolidin-1-yl)ethyl]amino | 95 | 3.50 | 569 |
| 487 | piperazin-1-yl | 85 | 3.33 | 526 |
| 488 | (tert-pentyl)amino | 85 | 4.49 | 527 |
| 489 | 1,4-diazepan-1-yl | 90 | 3.34 | 540 |

-continued

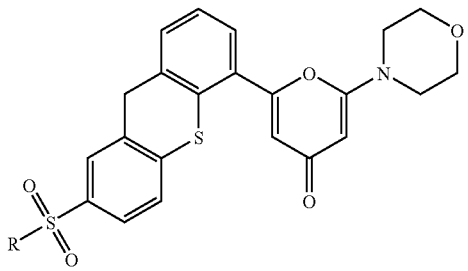

| Compound | R | Purity (%) | Retention Time (Mins) | M⁺+1 |
|---|---|---|---|---|
| 490 | HO-CH₂CH₂-N(CH₂CH₂-OH)-* | 85 | 3.56 | 545 |
| 491 | Et₂N-* | 90 | 4.53 | 513 |
| 492 | (iPr)N-piperazinyl-* | 90 | 3.34 | 568 |
| 493 | morpholin-N-* | 95 | 4.29 | 553 |

[5-(6-Morpholin-4-yl-4-oxo-4H-pyran-2-yl)-9H-thioxanthen-2-yloxy]-acetic acid methyl ester To a solution of 2-(7-Amino-9H-thioxanthen-4-yl)-6-morpholin-4-yl-pyran-4-one (1.01 g, 2.56 mmol) in anhydrous DMF (25 ml) was added powdered potassium carbonate (716 mg, 5.18 mmol) followed by methylbromoacetate (400 μl, 4.1 mmol). The reaction was stirred at room temperature for 100 hours whereupon it was quenched by dropwise addition of water (75 ml). The mixture was extracted using EtOAc (3×30 ml). The organic extracts were then combined, dried using MgSO₄, filtered and concentrated in vacuo to give the title compound as a brown oil that was used without further purification (1.02 g, 85.7%), m/z (LC-MS, ESP), RT=4.05 min, (M⁺+1)=466

[5-(6-Morpholin-4-yl-4-oxo-4H-pyran-2-yl)-9H-thioxanthen-2-yloxy]-acetic acid sodium salt To a solution of [5-(6-Morpholin-4-yl-4-oxo-4H-pyran-2-yl)-9H-thioxanthen-2-yloxy]-acetic acid methyl ester (1.02 g, 2.18 mmol) in THF (25 ml) was added aqueous NaOH (2.4 ml, 2.4 mmol, 1M solution). The mixture was stirred at 40° C. for 2 hours whereupon it was cooled to room temperature and concentrated in vacuo to give a brown oil. The residue was azeotroped with toluene (3×10 ml) to give the title compound as a fine, dark brown powder that was used without further purification (1.03 g, 100%), m/z (LC-MS, ESP), RT=3.72 min, (M⁺+1)-Na⁺=452

2-[5-(6-Morpholin-4-yl-4-oxo-4H-pyran-2-yl)-9H-thioxanthen-2-yloxy]-acetamide derivatives

[5-(6-Morpholin-4-yl-4-oxo-4H-pyran-2-yl)-9H-thioxanthen-2-yloxy]-acetic acid sodium salt (20 mg, 0.04 mmol) was diluted in anhydrous DMF (0.5 ml). To this solution was then added HBTU (33 mg, 0.09 mmol), diisopropylethylamine (74 μl, 0.2 mmol) and the appropriate amine (0.08 mmol). After stirring the reaction mixture for 24 hours at room temperature the crude mixture was purified by preparative HPLC to give the desired compounds, which are shown below:

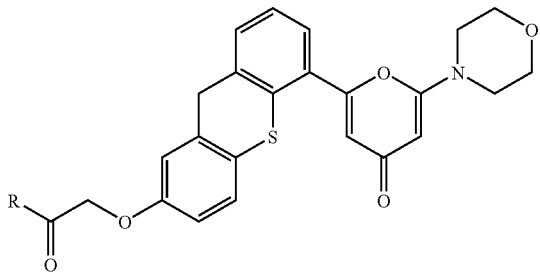
| Compound | R | Purity (%) | Retention Time (Mins) | M⁺+1 |
|---|---|---|---|---|
| 494 | morpholine | 95 | 3.72 | 521 |
| 495 | 1-methylpyrrolidin-2-yl-ethylamino | 85 | 3.28 | 562 |
| 496 | F₃C-CH₂-NH- | 85 | 4.17 | 533 |
| 497 | tetrahydrofuran-2-yl-methylamino | 85 | 3.83 | 535 |
| 498 | 2-(pyridin-2-yl)ethylamino | 90 | 3.33 | 556 |
| 499 | cyclobutylamino | 90 | 4.17 | 505 |
| 500 | methylthioethylamino | 95 | 4.05 | 525 |
| 501 | furan-2-ylmethylamino | 95 | 4.06 | 531 |
| 502 | 2-methoxyethylamino | 95 | 3.75 | 509 |
| 503 | 3-morpholinopropylamino | 90 | 3.28 | 578 |
| 504 | cyanomethylamino | 95 | 3.81 | 590 |
| 505 | tris(hydroxymethyl)methylamino | 85 | 3.42 | 555 |

-continued
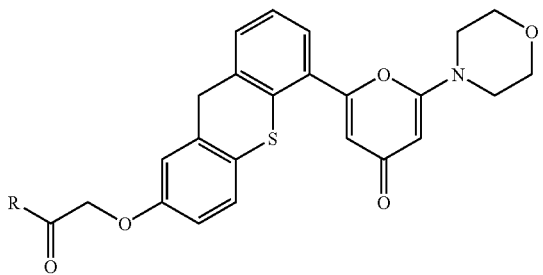
| Compound | R | Purity (%) | Retention Time (Mins) | M⁺+ 1 |
|---|---|---|---|---|
| 506 | imidazole-CH₂CH₂-NH-* | 85 | 3.27 | 545 |
| 507 | (HOCH₂)₂CH-NH-* | 85 | 3.38 | 525 |
| 508 | morpholino-NH-* | 85 | 3.58 | 536 |
| 509 | 4-carbamoyl-piperidin-1-yl-* | 90 | 3.50 | 562 |
| 510 | thiomorpholin-4-yl-* | 90 | 4.13 | 537 |
| 511 | 3-(hydroxymethyl)piperidin-1-yl-* | 85 | 3.68 | 549 |
| 512 | pyridin-3-yl-NH-* | 85 | 3.55 | 528 |
| 513 | (2-hydroxycycloheptyl)methyl-NH-* | 90 | 4.13 | 577 |

-continued

| Compound | R | Purity (%) | Retention Time (Mins) | M⁺+1 |
|---|---|---|---|---|
| 514 | (pyridin-2-yl)ethyl-N(Me)- | 95 | 3.38 | 570 |
| 515 | cyclopentyl-NH-CH₂CH₂CH₂-O- | 95 | 3.64 | 553 |
| 516 | pyrrolidinyl-CH₂CH₂CH₂-O- | 95 | 3.55 | 562 |
| 517 | piperidinyl-CH₂CH₂CH₂-O- | 90 | 3.35 | 562 |
| 518 | morpholinyl-CH₂CH₂CH₂-O- | 95 | 4.08 | 549 |
| 519 | azepanyl-CH₂CH₂CH₂-O- | 90 | 3.24 | 536 |
| 520 | PhC(O)NHNH-CH₂CH₂CH₂-O- | 90 | 3.29 | 578 |
| 521 | azepanyl-N-NH-CH₂CH₂CH₂-O- | 95 | 3.23 | 534 |
| 522 | (4-methylpiperazin-1-yl)-NH-CH₂CH₂CH₂-O- | 90 | 3.21 | 564 |
| 523 | morpholinyl-N-NH-CH₂CH₂CH₂-O- | 85 | 3.34 | 562 |

-continued
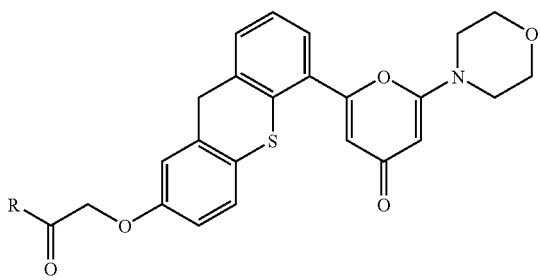
| Compound | R | Purity (%) | Retention Time (Mins) | M⁺+ 1 |
|---|---|---|---|---|
| 524 | 4-ethylpiperazin-1-yl* | 90 | 3.23 | 548 |
| 525 | (1-methylpyrrolidin-2-yl)ethyl-NH-propyl-O-* | 85 | 3.30 | 542 |
| 526 | pyridin-2-yl-NH-propyl-O-* | 90 | 4.22 | 519 |
| 527 | pyridin-4-yl-NH-propyl-O-* | 85 | 3.46 | 563 |
| 528 | piperazin-1-yl* | 95 | 3.23 | 520 |
| 529 | 4-methyl-1,4-diazepan-1-yl* | 95 | 3.26 | 548 |
| 530 | N,N-bis(2-hydroxyethyl)amino* | 85 | 3.39 | 539 |
| 531 | N,N-bis(2-methoxyethyl)amino* | 85 | 3.99 | 567 |
| 532 | azepan-1-yl* | 95 | 4.37 | 533 |
| 533 | diethylamino* | 95 | 4.13 | 507 |

2-[7-(2-Amino-ethoxy)-9H-thioxanthen-4-yl]-6-morpholin-4-yl-pyran-4-one derivatives To a solution of 2-(7-Hydroxy-9H-thioxanthen-4-yl)-6-morpholin-4-yl-pyran-4-one (20 mg, 0.05 mmol) in DMA (1 ml) was added NaH (60% dispersion in mineral oil, 6 mg 0.15 mmol) at 0° C. The mixture was stirred at 0° C. for 30 minutes before the addition of 1,2-dibromoethane (19 mg, 0.1 mmol) The mixture was then allowed to warm to room temperature and stirred like this for 12 hours before the addition of the appropriate amine. The reaction was stirred for a further 24 hours the crude mixture was purified by preparative HPLC to give the desire compounds, which are shown below:

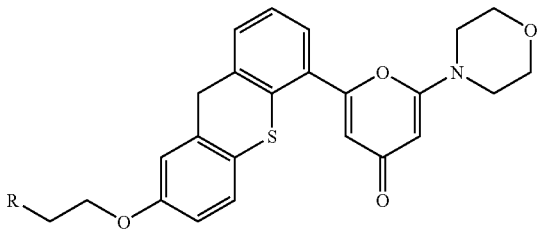

| Compound | R | Purity (%) | Retention Time (Mins) | M⁺+1 |
|---|---|---|---|---|
| 534 | | 90 | 3.38 | 521 |
| 535 | | 90 | 3.44 | 542 |
| 536 | | 95 | 3.45 | 491 |
| 537 | | 95 | 3.45 | 479 |
| 538 | | 90 | 3.04 | 564 |
| 539 | | 95 | 3.24 | 511 |
| 540 | | 95 | 3.49 | 523 |

-continued

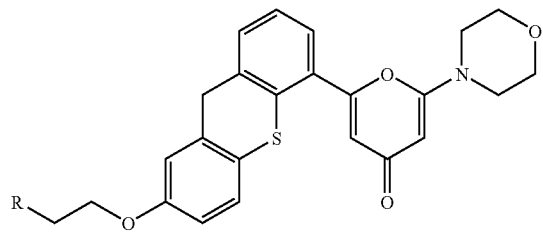

| Compound | R | Purity (%) | Retention Time (Mins) | M⁺+1 |
|---|---|---|---|---|
| 541 | 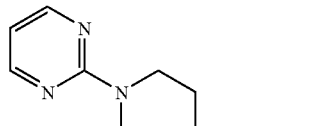 | 85 | 3.72 | 584 |
| 542 | 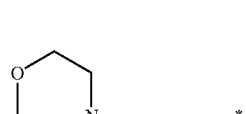 | 90 | 3.33 | 507 |

B) Biological Examples

Materials and Methods

In Vitro ATM Inhibition Assays

In order to assess the inhibitory action of the compounds against ATM in vitro, the following assay was used to determine $IC_{50}$ values. ATM protein was immunoprecipitated from HeLa cell nuclear extract using rabbit polyclonal anti-sera raised to the C-terminal ~500 amino-acid residues of the human ATM protein. The immunoprecipitation was performed according to the methodology described by Banin, S. et al. (1998). 10 μl of immunoprecipitated ATM in Buffer C (50 mM Hepes, pH 7.4, 6 mM $MgCl_2$, 150 mM NaCl, 0.1 mM sodium orthovanadate, 4 mM MnCl2, 0.1 mM dithiothreitol, 10% glycerol) was added to 32.5 μl of buffer C containing 1 μg of the ATM substrate GSTp53N66 in a V-bottomed 96 well polypropylene plate. The GSTp53N66 substrate is the amino terminal 66 amino acid residues of human wild type p53 fused to glutathione S-transferase. ATM phosphorylates p53 on the residue serine 15 (Banin, S. et al. (1998)). Varying concentrations of inhibitor were then added. All compounds were diluted in DMSO to give a final assay concentration of between 100 μM and 0.1 nM, with DMSO being at a final concentration of 1%. After 10 minutes of incubation at 37° C., the reactions were initiated by the addition of 5 μl of 500 μM Na-ATP. After 1 hour with shaking at 37° C., 150 μl of phosphate buffered saline (PBS) was added to the reaction and the plate centrifuged at 1500 rpm for 10 minutes. 5 μl of the reaction was then transferred to a 96 well opaque white plate containing 45 μl of PBS to allow the GSTp53N66 substrate to bind to the plate wells. The plate was covered and incubated at room temperature for 1 hour with shaking before discarding the contents. The plate wells were washed twice by the addition of PBS prior to the addition of 3% (w/v) bovine serum albumin (BSA) in PBS. The plate was incubated at room temperature for 1 hour with shaking before discarding the contents and washing twice with PBS. To the wells, 50 μl of a 1:10,000 dilution of primary phosphoserine-15 antibody (Cell Signaling Technology, #9284L) in 3% BSA/PBS was added to detect the phosphorylation event on the serine 15 residue of p53 elicited by the ATM kinase. After 1 hour of incubation at room temperature with shaking, the wells were washed four times with PBS prior to the addition of an anti-rabbit HRP conjugated secondary antibody (Pierce, 31462) with shaking for 1 hour at room temperature. The wells were then washed four times with PBS before the addition of chemiluminescence reagent (NEN Renaissance, NEL105). The plate was then shaken briefly, covered with a transparent plate seal and transferred to a TopCount NXT for chemiluminescent counting. Counts per second, following a one second counting time, were recorded for each reaction.

The enzyme activity for each compound is then calculated using the following equation:

$$\% \text{ Inhibition} = 100 - \left(\frac{(cpm \text{ of unknown} - \text{mean negative } cpm) \times 100}{(\text{mean positive } cpm - \text{mean negative } cpm)}\right)$$

Results

In vitro ATM assays

Compounds were assayed for ATM inhibition activity using the method described above. The results are detailed below as $IC_{50}$ values (the concentration at which 50% of the enzyme activity is inhibited). These are determined over a range of different concentrations, normally from 100 μM down to 0.1 nM. Such $IC_{50}$ values are used as comparative values to identify increased compound potencies.

The following compounds had $IC_{50}$ values of less than 200 nM: 6, 8, 9, 11, 13-19, 21-129, 148, 153, 164, 170, 172, 181, 182, 200, 240-257, 259-262, 264, 266, 267, 270-272, 274, 277, 280-292, 294-307, 311, 312, 315, 321, 322, 324, 326-331, 333, 336, 338-356, 359, 361, 366, 367, 378, 379, 381-

383, 395, 398, 399, 403, 405, 407, 409-411, 414, 416-419, 424, 426, 427, 430, 433-442, 444-446, 450, 454, 455, 457-459, 462, 465-466, 468-469, 471-476, 478, 480, 482, 484, 485, 488-490, 493, 494, 496-497, 499-501, 504-507, 509-513, 515, 516, 518, 520-526, 528, 532-533, 537, 540-542.

The following compounds had $IC_{50}$ values of less than 10 μM, in addition to those listed above: 7, 10, 12, 20, 131-147, 149-152, 154-163, 165-169, 171, 173-180, 183-199, 201-238, 256, 258, 263, 265, 268, 269, 273, 275, 276, 278, 279, 293, 308-310, 313, 314, 316-320, 322, 323, 325, 332, 334, 335, 358, 362, 363, 365, 368, 370-375, 377, 380, 384-392, 400-402, 406, 408, 412, 413, 415, 421-423, 425, 428, 429, 431-432, 443, 447-449, 452, 453, 456, 460, 461, 463, 464, 470, 477, 481, 483, 486, 487, 491, 492, 495, 498, 502, 503, 514, 517, 519, 527, 529-531, 534-536, 538.

The invention claimed is:

1. A compound of formula II:

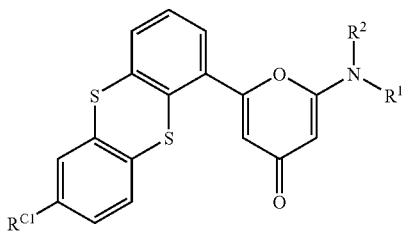

and isomers, salts, solvates, chemically protected forms, and prodrugs thereof, wherein:

$R^1$ and $R^2$ together form, along with the nitrogen atom to which they are attached, an optionally substituted heterocyclic ring having from 4 to 8 ring atoms;

$R^{C1}$ is —$NR^3R^4$, where $R^3$ and $R^4$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms, or $R^{C1}$ is of formula IIa:

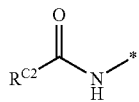

wherein $R^{C2}$ is selected from an optionally substituted $C_{1-7}$ alkyl group, an optionally substituted $C_{3-20}$ heterocyclyl group, an optionally substituted $C_{5-20}$ aryl group, an ester group, an ether group and an amino group.

2. A compound according to claim 1, wherein $R^{C1}$ is —$NR^3R^4$, and $R^3$ and $R^4$ are selected from H and optionally substituted $C_{1-7}$ alkyl groups.

3. A compound according to claim 1, wherein $R^{C1}$ is of formula IIa.

4. A compound according to claim 3, wherein $R^{C2}$ is selected from an optionally substituted $C_{1-7}$ alkyl group, an optionally substituted $C_{3-20}$ heterocyclyl group, an optionally substituted $C_{5-20}$ aryl group and an ester group.

5. A compound according to claim 4, wherein $R^{C2}$ is an ester group, and the ester substituent is a $C_{1-7}$ alkyl group.

6. A compound according to claim 4, wherein $R^{C2}$ is an optionally substituted $C_{5-7}$ heterocylyl group containing at least one nitrogen ring atom.

7. A compound according to claim 4, wherein $R^{C2}$ is an optionally substituted $C_{5-6}$ aryl group.

8. A compound according to claim 7, wherein $R^{C2}$ is selected from optionally substituted phenyl and a $C_{5-6}$ heteroaryl group containing one or two heteroatoms selected from nitrogen, oxygen and sulphur.

9. A compound according to claim 4, wherein $R^{C2}$ is an optionally substituted $C_{1-7}$ alkyl group, wherein optional substituents are selected from amino, thioether, ester, $C_{5-20}$ aryl, $C_{3-20}$ heterocyclyl, acyloxy, ether and alkoxy.

10. A compound according to claim 4, wherein $R^{C2}$ is of formula IIb:

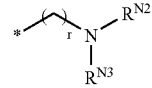

wherein r is from 1 to 3; and $R^{N2}$ and $R^{N3}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted heterocyclic ring having from 4 to 8 ring atoms.

11. A compound according to claim 10, wherein $R^{N2}$ and $R^{N3}$ are independently selected from hydrogen, optionally substituted $C_{1-7}$ alkyl groups or together form, along with the nitrogen atom to which they are attached, an optionally substituted heterocyclic ring having from 4 to 8 ring atoms.

12. A compound according to claim 1, wherein $R^1$ and $R^2$ form, along with the nitrogen atom to which they are attached, a ring selected from morpholino and thiomorpholino.

* * * * *